(12) United States Patent
Jostock et al.

(10) Patent No.: US 11,242,551 B2
(45) Date of Patent: Feb. 8, 2022

(54) EUKARYOTIC CELLS AND METHODS FOR RECOMBINANTLY EXPRESSING A PRODUCT OF INTEREST

(71) Applicant: Novartis AG, Basel (CH)

(72) Inventors: Thomas Jostock, Neuenburg am Rhein (DE); Holger Laux, Basel (CH); Anett Ritter, Weil am Rhein (DE)

(73) Assignee: Novartis AG, Basel (CH)

( * ) Notice: Subject to any disclaimer, the term of this patent is extended or adjusted under 35 U.S.C. 154(b) by 46 days.

(21) Appl. No.: 15/104,601

(22) PCT Filed: Dec. 18, 2014

(86) PCT No.: PCT/IB2014/067076
§ 371 (c)(1),
(2) Date: Jun. 15, 2016

(87) PCT Pub. No.: WO2015/092737
PCT Pub. Date: Jun. 25, 2015

(65) Prior Publication Data
US 2017/0058307 A1 Mar. 2, 2017

Related U.S. Application Data

(60) Provisional application No. 61/919,340, filed on Dec. 20, 2013.

(51) Int. Cl.
| | | |
|---|---|---|
| *C12N 15/85* | (2006.01) | |
| *C12N 15/00* | (2006.01) | |
| *C12P 21/00* | (2006.01) | |
| *C07K 14/47* | (2006.01) | |
| *C12N 15/113* | (2010.01) | |
| *C12N 5/00* | (2006.01) | |
| *C12Q 1/6888* | (2018.01) | |
| *C12N 15/90* | (2006.01) | |

(52) U.S. Cl.
CPC ............. *C12P 21/00* (2013.01); *C07K 14/47* (2013.01); *C07K 14/4703* (2013.01); *C12N 5/00* (2013.01); *C12N 15/113* (2013.01); *C12Q 1/6888* (2013.01); *C12N 15/907* (2013.01); *C12N 2310/14* (2013.01); *C12N 2510/02* (2013.01); *C12N 2511/00* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2005/0272061 A1 | 12/2005 | Petroziello et al. |
| 2017/0002059 A1 | 1/2017 | Jostock et al. |

FOREIGN PATENT DOCUMENTS

| | | |
|---|---|---|
| CN | 101765660 A | 6/2010 |
| CN | 101784666 A | 7/2010 |
| CN | 102414320 A | 4/2012 |
| EP | 0246049 A1 | 11/1987 |
| EP | 0724639 A1 | 8/1996 |
| EP | 3083676 A1 | 10/2016 |
| JP | 2001-037478 | 2/2001 |
| RU | 2487168 C2 | 7/2013 |
| WO | 9208796 A1 | 5/1992 |
| WO | 9217566 A2 | 10/1992 |
| WO | 9428143 A1 | 12/1994 |
| WO | 03014361 A1 | 2/2003 |
| WO | 03099996 A2 | 12/2003 |
| WO | 2004035732 A2 | 4/2004 |
| WO | 2004081167 A2 | 9/2004 |
| WO | 2005073375 A1 | 8/2005 |
| WO | 2006059323 A2 | 6/2006 |
| WO | 2007131774 A1 | 11/2007 |
| WO | 2008064095 A1 | 5/2008 |
| WO | 2008098933 A1 | 8/2008 |
| WO | 2008133711 A2 | 11/2008 |
| WO | 2009080759 A1 | 7/2009 |
| WO | 2010022961 A1 | 3/2010 |
| WO | 2010097240 A1 | 9/2010 |
| WO | 2010130800 A1 | 11/2010 |
| WO | 2015092735 A1 | 6/2015 |

OTHER PUBLICATIONS

Bork (Genome Research, 10:348-400, 2000).*
Smith et al. (Nature Biotechnology 15:1222-1223, 1997).*
Brenner (TIG 15:132-133, 1999).*
Broun et al. (Science 282:1315-1317, 1998).*
Van de Loo et al. (Proc. Natl. Acad. Sci. 92:6743-6747, 1995).*
Novel human diagnostic protein #23767, Acession No. ABG23776, Drmanac et al. 2002.*
Munoz, I.M. et al: "Family with Sequence Similarity 60A (FAM60A) Protein Is a Celll . . .", Journal of Biological Chemistry, Sep. 21, 2012, vol. 287, No. 39, pp. 32346-32353, XP055184093.
Smith, K.T. et al: "Human Family with Sequence Similarity 60 Memer A (FAM60A) Protein: A New Subunit of the Sin3 . . .", Molecular & Cellular Proteomics, Sep. 14, 2012, vol. 11, No. 12, pp. 1815-1828, XP055184106.

(Continued)

*Primary Examiner* — Celine X Qian
(74) *Attorney, Agent, or Firm* — Nelson Mullins Riley & Scarborough LLP; Jane E. Remillard, Esq.; Jill Gorny Sloper, Esq.

(57) ABSTRACT

The disclosure pertains to novel eukaryotic cell suitable for recombinant production of a product of interest, wherein the genome of the host cell is altered so that the effect of protein FAM60A is impaired in said cell, e.g. by reducing or eliminating functional expression of gene FAM60A thereby improving the stability characteristics. Furthermore, the present disclosure provides associated technologies wherein such host cells are used in recombinant production technologies.

22 Claims, 9 Drawing Sheets

Specification includes a Sequence Listing.

(56) References Cited

OTHER PUBLICATIONS

Smith, Karen T. et al: "Human Family with Sequence Similarity 60 Member A (FAM60A) Protein", Molecular & Cellular Proteomics, Sep. 14, 2012, pp. S1-S11, XP055184114.
Kobayashi H. et al: "Fluorescence in situ hybridization mapping of translocations & deletions . . .", Blood, Nov. 15, 1994, op.3473-3482, XP055173050.
"Eukaryote" by Scitable by Nature Education, accessed online at https://www.nature.com/scitable/definition/eukaryote-eucariote-294/ on Sep. 12, 2019, p. 1.
Chusainow, J. et al., "A Study of Monoclonal Antibody-Producing CHO Cell Lines: What Makes a Stable High Producer?," Biotechnology and Bioengineering, vol. 102 (4):1182-1196 (2009).
Notice of Opposition, European Application No. 14821859.7, dated Jun. 4, 2020,.
Oostvogels, R. et al; "Towards effective and safe immunotherapy after allogeneic stem cell transplantation: identification of hematopoietic-specific minor histocompatability antigen UTA2-1"; Leukemia, Oct. 1, 2012, vol. 27, No. 3, pp. 642-649.
Ritter, A et al., "Deletion of a Telomeric Region on Chromosome 8 Correlates With Higher Productivity and Stability of CHO Cell Lines," Biotechnology and Bioengineering, vol. 113(5):1084-1093 (2016).
Uncharacterized Protein KIAA1551, EBI Accession No. UNIPROT:Q9HCM1, Jul. 24, 2007.
Wurm, F. et al., "First CHO genome," Nature Biotechnology, vol. 29 (8):718-720 (2011).
Brinkrolf, K. et al., "Chinese hamster genome sequenced from sorted chromosomes." Nature Biotechnology, vol. 31:694-695 (2013).
Grillari, J. et al., "Analysis of alterations in gene expression after amplification of recombinant genes in CHO cells," J. Biotechnol., vol. 87: 59-65 (2001).
Reply to the Notice of Opposition, European Application No. 14821859.7, dated Oct. 29, 2020, 41 pages.
Summons to Attend Proceedings. European Application No. 14821859.7, dated Feb. 2, 2021, 30 pages.
Xu, X. et al., "The genomic sequence of the Chinese hamster ovary (CHO)-K1 cell line," Nature Biotechnology, vol. 29 (8): 735-741 (2011).

\* cited by examiner

SEQUENCE LISTING

```
<160> NUMBER OF SEQ ID NOS: 60

<210> SEQ ID NO 1
<211> LENGTH: 221
<212> TYPE: PRT
<213> ORGANISM: Homo sapiens

<400> SEQUENCE: 1

Met Phe Gly Phe His Lys Pro Lys Met Tyr Arg Ser Ile Glu Gly Cys
1               5                   10                  15

Cys Ile Cys Arg Ala Lys Ser Ser Ser Arg Phe Thr Asp Ser Lys
            20                  25                  30

Arg Tyr Glu Lys Asp Phe Gln Ser Cys Phe Gly Leu His Glu Thr Arg
        35                  40                  45

Ser Gly Asp Ile Cys Asn Ala Cys Val Leu Leu Val Lys Arg Trp Lys
    50                  55                  60

Lys Leu Pro Ala Gly Ser Lys Lys Asn Trp Asn His Val Val Asp Ala
65                  70                  75                  80

Arg Ala Gly Pro Ser Leu Lys Thr Thr Leu Lys Pro Lys Lys Val Lys
                85                  90                  95

Thr Leu Ser Gly Asn Arg Ile Lys Ser Asn Gln Ile Ser Lys Leu Gln
            100                 105                 110

Lys Glu Phe Lys Arg His Asn Ser Asp Ala His Ser Thr Thr Ser Ser
        115                 120                 125
```

```
Ala Ser Pro Ala Gln Ser Pro Cys Tyr Ser Asn Gln Ser Asp Asp Gly
        130                 135                 140

Ser Asp Thr Glu Met Ala Ser Gly Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Asn Lys Lys Ala Ala Glu Lys Pro Glu Glu
        195                 200                 205

Gln Gly Pro Glu Pro Leu Pro Ile Ser Thr Gln Glu Trp
    210                 215                 220
```

<210> SEQ ID NO 2
<211> LENGTH: 221
<212> TYPE: PRT
<213> ORGANISM: Rattus norvegicus

<400> SEQUENCE: 2

```
Met Phe Gly Phe His Lys Pro Lys Met Tyr Arg Ser Ile Glu Gly Cys
1               5                   10                  15

Cys Ile Cys Arg Ala Lys Ser Ser Ser Arg Phe Thr Asp Ser Lys
            20                  25                  30

Arg Tyr Glu Lys Asp Phe Gln Ser Cys Phe Gly Leu His Glu Thr Arg
            35                  40                  45

Ser Gly Asp Ile Cys Asn Ala Cys Val Leu Leu Val Lys Arg Trp Lys
    50                  55                  60

Lys Leu Pro Ala Gly Ser Lys Lys Asn Trp Asn His Val Val Asp Ala
65                  70                  75                  80

Arg Ala Gly Pro Ser Leu Lys Thr Thr Leu Lys Pro Lys Lys Val Lys
                85                  90                  95

Thr Leu Ser Gly Asn Arg Met Lys Ser Ser Gln Ile Ser Lys Leu Gln
            100                 105                 110

Lys Glu Phe Lys Arg His Asn Ser Asp Ala His Ser Thr Thr Ser Ser
        115                 120                 125

Ala Ser Pro Ala Gln Ser Pro Cys Tyr Ser Asn Gln Ser Asp Glu Gly
    130                 135                 140

Ser Asp Thr Glu Met Ala Ser Ser Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Ser Lys Lys Ala Ala Glu Lys Pro Glu Glu
        195                 200                 205

Gln Ala Pro Ala Pro Leu Pro Ile Ser Thr Gln Glu Trp
    210                 215                 220
```

<210> SEQ ID NO 3
<211> LENGTH: 221
<212> TYPE: PRT
<213> ORGANISM: Mus musculus

<400> SEQUENCE: 3

```
Met Phe Gly Phe His Lys Pro Lys Met Tyr Arg Ser Ile Glu Gly Cys
1               5                   10                  15
```

```
Cys Ile Cys Arg Ala Lys Ser Ser Ser Arg Phe Thr Asp Ser Lys
            20                  25                  30

Arg Tyr Glu Lys Asp Phe Gln Ser Cys Phe Gly Leu His Glu Thr Arg
        35                  40                  45

Ser Gly Asp Ile Cys Asn Ala Cys Val Leu Leu Val Lys Arg Trp Lys
    50                  55                  60

Lys Leu Pro Ala Gly Ser Lys Lys Asn Trp Asn His Val Val Asp Ala
65                  70                  75                  80

Arg Ala Gly Pro Ser Leu Lys Thr Thr Leu Lys Pro Lys Lys Val Lys
                85                  90                  95

Thr Leu Ser Gly Asn Arg Met Lys Ser Asn Gln Ile Ser Lys Leu Gln
            100                 105                 110

Lys Glu Phe Lys Arg His Asn Ser Asp Ala His Ser Thr Thr Ser Ser
        115                 120                 125

Ala Ser Pro Ala Gln Ser Pro Cys Tyr Ser Asn Gln Ser Asp Glu Gly
    130                 135                 140

Ser Asp Thr Glu Met Ala Ser Ser Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Ser Lys Lys Ala Ala Glu Lys Pro Glu Glu
        195                 200                 205

Gln Gly Pro Ala Pro Leu Pro Ile Ser Thr Gln Glu Trp
    210                 215                 220

<210> SEQ ID NO 4
<211> LENGTH: 221
<212> TYPE: PRT
<213> ORGANISM: Cricetulus griseus

<400> SEQUENCE: 4

Met Phe Gly Phe His Lys Pro Lys Met Tyr Arg Ser Ile Glu Gly Cys
1               5                   10                  15

Cys Ile Cys Arg Ala Lys Ser Ser Ser Arg Phe Thr Asp Ser Lys
            20                  25                  30

Arg Tyr Glu Lys Asp Phe Gln Ser Cys Phe Gly Leu His Glu Thr Arg
        35                  40                  45

Ser Gly Asp Ile Cys Asn Ala Cys Val Leu Leu Val Lys Arg Trp Lys
    50                  55                  60

Lys Leu Pro Ala Gly Ser Lys Lys Asn Trp Asn His Val Ser His Ser
65                  70                  75                  80

Arg Ala Gly Pro Ser Leu Lys Thr Thr Leu Lys Pro Lys Lys Val Lys
                85                  90                  95

Thr Leu Ser Gly Asn Arg Met Lys Ser Asn Gln Ile Ser Lys Leu Gln
            100                 105                 110

Lys Glu Phe Lys Arg His Asn Ser Asp Ala His Ser Thr Thr Ser Ser
        115                 120                 125

Ala Ser Pro Ala Gln Ser Pro Cys Tyr Ser Asn Gln Ser Asp Asp Gly
    130                 135                 140

Ser Asp Thr Glu Met Ala Ser Ser Ser Asn Arg Thr Pro Val Phe Ser
145                 150                 155                 160

Phe Leu Asp Leu Thr Tyr Trp Lys Arg Gln Lys Ile Cys Cys Gly Ile
```

```
            165                 170                 175
Ile Tyr Lys Gly Arg Phe Gly Glu Val Leu Ile Asp Thr His Leu Phe
            180                 185                 190

Lys Pro Cys Cys Ser Ser Lys Lys Ala Ala Pro Glu Lys Pro Glu Glu
            195                 200                 205

Gln Gly Pro Ala Pro Leu Pro Ile Ser Thr Gln Glu Trp
            210                 215                 220
```

<210> SEQ ID NO 5
<211> LENGTH: 222
<212> TYPE: PRT
<213> ORGANISM: Gallus gallus

<400> SEQUENCE: 5

```
Met Phe Gly Phe Arg Lys Pro Lys Met Tyr Arg Ser Ile Glu Gly Cys
1               5                   10                  15

Cys Ile Cys Arg Ala Lys Ser Ser Ser Arg Phe Thr Asp Ser Lys
            20                  25                  30

Arg Tyr Glu Lys Asp Phe Gln Asn Cys Phe Gly Leu His Glu Ala Arg
            35                  40                  45

Ser Gly Asp Ile Cys Asn Ala Cys Val Leu Leu Val Lys Arg Trp Lys
        50                  55                  60

Lys Leu Pro Ala Gly Ser Lys Lys Asn Trp Asn His Val Val Asp Ala
65                  70                  75                  80

Arg Ala Gly Pro Ser Leu Lys Thr Thr Leu Lys Pro Lys Lys Met Lys
                85                  90                  95

Thr Leu Ser Gly Ser Arg Ile Lys Ser Asn Gln Ile Ser Lys Leu Gln
            100                 105                 110

Lys Glu Phe Lys Arg His Asn Ser Asp Ala His Ser Thr Thr Ser Ser
            115                 120                 125

Ala Ser Pro Ala Gln Ser Pro Cys Tyr Ser Asn Gln Ser Asp Glu Gly
        130                 135                 140

Ser Asp Thr Glu Met Ser Ala Gly Ser Ser Arg Thr Pro Val Phe Ser
145                 150                 155                 160

Phe Leu Asp Leu Thr Tyr Trp Lys Arg Gln Lys Val Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Asn Lys Lys Ser Ala Thr Glu Lys Pro Glu Gln
            195                 200                 205

Glu Gly Pro Gln Ser Pro Ala Ile Ser Thr Gln Glu Trp
        210                 215                 220
```

<210> SEQ ID NO 6
<211> LENGTH: 221
<212> TYPE: PRT
<213> ORGANISM: Pan troglodytes

<400> SEQUENCE: 6

```
Met Phe Gly Phe His Lys Pro Lys Met Tyr Arg Ser Ile Glu Gly Cys
1               5                   10                  15

Cys Ile Cys Arg Ala Lys Ser Ser Ser Ser Arg Phe Thr Asp Ser Lys
            20                  25                  30

Arg Tyr Glu Lys Asp Phe Gln Ser Cys Phe Gly Leu His Glu Thr Arg
            35                  40                  45

Ser Gly Asp Ile Cys Asn Ala Cys Val Leu Leu Val Lys Arg Trp Lys
```

```
            50                  55                  60
Lys Leu Pro Ala Gly Ser Lys Lys Asn Trp Asn His Val Val Asp Ala
 65                  70                  75                  80

Arg Ala Gly Pro Ser Leu Lys Thr Thr Leu Lys Pro Lys Lys Val Lys
                 85                  90                  95

Thr Leu Ser Gly Asn Arg Ile Lys Ser Asn Gln Ile Ser Lys Leu Gln
            100                 105                 110

Lys Glu Phe Lys Arg His Asn Ser Asp Ala His Ser Thr Thr Ser Ser
        115                 120                 125

Ala Ser Pro Ala Gln Ser Pro Cys Tyr Ser Asn Gln Ser Asp Asp Gly
    130                 135                 140

Ser Asp Thr Glu Met Ala Ser Gly Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Asn Lys Lys Ala Ala Ala Glu Lys Pro Glu Glu
        195                 200                 205

Gln Gly Pro Glu Pro Leu Pro Ile Ser Thr Gln Glu Trp
    210                 215                 220

<210> SEQ ID NO 7
<211> LENGTH: 221
<212> TYPE: PRT
<213> ORGANISM: Pongo abelii

<400> SEQUENCE: 7

Met Phe Gly Phe His Lys Pro Lys Met Tyr Arg Ser Ile Glu Gly Cys
  1               5                  10                  15

Cys Ile Cys Arg Ala Lys Ser Ser Ser Arg Phe Thr Asp Ser Lys
             20                  25                  30

Arg Tyr Glu Lys Asp Phe Gln Ser Cys Phe Gly Leu His Glu Thr Arg
         35                  40                  45

Ser Gly Asp Ile Cys Asn Ala Cys Val Leu Leu Val Lys Arg Trp Lys
     50                  55                  60

Lys Leu Pro Ala Gly Ser Lys Lys Asn Trp Asn His Val Val Asp Ala
 65                  70                  75                  80

Arg Ala Gly Pro Ser Leu Lys Thr Thr Leu Lys Pro Lys Lys Val Lys
                 85                  90                  95

Thr Leu Ser Gly Asn Arg Ile Lys Ser Asn Gln Ile Ser Lys Leu Gln
            100                 105                 110

Lys Glu Phe Arg Arg His Asn Ser Asp Ala His Ser Thr Thr Ser Ser
        115                 120                 125

Ala Ser Pro Ala Gln Ser Pro Cys Tyr Ser Asn Gln Ser Asp Asp Gly
    130                 135                 140

Ser Asp Thr Glu Met Ala Ser Gly Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Asn Lys Lys Ala Ala Ala Glu Lys Pro Glu Glu
        195                 200                 205
```

```
        Gln Gly Pro Glu Pro Leu Pro Ile Ser Thr Gln Glu Trp
            210                 215                 220

<210> SEQ ID NO 8
<211> LENGTH: 221
<212> TYPE: PRT
<213> ORGANISM: Bos taurus

<400> SEQUENCE: 8

Met Phe Gly Phe His Lys Pro Lys Met Tyr Arg Ser Ile Glu Gly Cys
1               5                   10                  15

Cys Ile Cys Arg Ala Lys Ser Ser Ser Arg Phe Thr Asp Ser Lys
            20                  25                  30

Arg Tyr Glu Lys Asp Phe Gln Ser Cys Phe Gly Leu His Glu Thr Arg
        35                  40                  45

Ser Gly Asp Ile Cys Asn Ala Cys Val Leu Leu Val Lys Arg Trp Lys
    50                  55                  60

Lys Leu Pro Ala Gly Ser Lys Lys Asn Trp Asn His Val Val Asp Ala
65                  70                  75                  80

Arg Ala Gly Pro Ser Leu Lys Thr Thr Leu Lys Pro Lys Lys Val Lys
                85                  90                  95

Thr Leu Ser Gly Asn Arg Ile Lys Ser Asn Gln Ile Ser Lys Leu Gln
            100                 105                 110

Lys Glu Phe Lys Arg His Asn Ser Asp Ala His Ser Thr Thr Ser Ser
        115                 120                 125

Ala Ser Pro Ala Gln Ser Pro Cys Tyr Ser Asn Gln Ser Asp Asp Gly
    130                 135                 140

Ser Asp Thr Glu Met Ala Ser Gly Ser Asn Arg Thr Pro Val Phe Ser
145                 150                 155                 160

Phe Leu Asp Leu Thr Tyr Trp Lys Arg Gln Lys Ile Cys Cys Gly Ile
                165                 170                 175

Ile Tyr Lys Gly Arg Phe Gly Glu Val Leu Ile Asp Thr His Leu Phe
            180                 185                 190

Lys Pro Cys Cys Ser Asn Lys Lys Ala Ala Ala Glu Lys Pro Glu Glu
        195                 200                 205

Gln Gly Pro Glu Pro Leu Pro Ile Ser Thr Gln Glu Trp
    210                 215                 220

<210> SEQ ID NO 9
<211> LENGTH: 1236
<212> TYPE: DNA
<213> ORGANISM: Cricetulus griseus

<400> SEQUENCE: 9
ctcagaagaa aagatgtttg gttttcacaa gccaaagatg taccgaagta tagagggctg    60
ctgtatctgc agagccaagt cctccagctc tcggttcacg acagtaaac gttatgaaaa    120 ggacttccag agctgttttg ggttgcacga gactcgctca ggagatatct gcaatgcctg    180
tgtgctgctt gtgaaaagat ggaagaagtt gccagcagga tcaaaaaaaa actggaatca    240
tgtgtcacac tcaagggcag gacccagtct aaagacaaca ttgaaaccaa agaaagtgaa    300
aactctatct ggaaacagga tgaaaagcaa ccagatcagt aaactgcaga aggagtttaa    360
acgccacaac tctgatgctc acagtaccac ctcaagtgcc tcgccagccc agtctccctg    420
ctacagtaac cagtcagatg atggctcaga cacagagatg gcttccagct ctaacagaac    480
tccagttttt tccttcttag atcttaccta ctggaaaaga cagaaaatat gttgtgggat    540
```

-continued

```
catctataag ggccgttttg gggaagtcct catcgacacg catctcttca agccttgctg    600
cagcagtaag aaggcagctc ctgagaagcc tgaggaacag ggaccagcgc ctctgcccat    660
ctctactcag gagtggtgac tgaggttcat gcagaaggga acaaagagca atttaaactt    720
tgaaaagacc acaaagcaac agactgaccc tcctattttt aacttggata cctgctattc    780
tgccaaaaga cattttctag aatagttttt aatgggttac ccatcccccc atccaacaaa    840
ctcggaagcc agttctagct tactgcaaga agagagtgta cataatattt aatatgctga    900
gtatttcata ggaaggctga atgctgctgt aaagtgctct ttaagtcttt ttttttttt     960 aatcccctct aatgaatgag attagggggg tttcagggga cagagatggg atttgttgtg   1020
tgataaacca tatgtagttt agtctttctg tggagaggca gtggttgggg cattttaaat   1080
ggctggctac acttgttttc ccctcatggt aatttgtcat aactcagtag cacgacctgc   1140
ccctagaagt agttaaagat ttttaaatgc taaggcgttg ccaaggttct gatgattcag   1200
acctgtacta ctgattatta agcaggacag actgag                             1236
```

<210> SEQ ID NO 10
<211> LENGTH: 1547
<212> TYPE: PRT
<213> ORGANISM: Cricetulus griseus

<400> SEQUENCE: 10

```
Met Asn Trp Asn Ala Lys Pro Glu Asn Ala Ala Pro Asn Pro Pro Tyr
1               5                   10                  15

Ser Lys Ser Gln Ser Ser Leu Leu Gln Gln Phe Leu Met Pro Ser Thr
            20                  25                  30

Thr Ser Gln Ser Ser Phe Ser Cys Leu Pro His Asn Gln Glu Ala Cys
        35                  40                  45

Ile Tyr Pro Thr Asn Ser Asn Ser Val Ser Gln Pro Leu Leu Asn Val
    50                  55                  60

Arg Ser Phe Ile Asn Pro Pro Ile Ser Val Ser Asn Val His Asn Arg
65                  70                  75                  80

Thr Val Val Ala Ser Gln Thr Ser Val Glu Arg Val Thr Tyr Thr Asn
                85                  90                  95

Val Lys Gly Ala Gln Gln Pro Asn His Asn Leu Gln Thr Val Ser Ser
            100                 105                 110

Gly Val Val Gln Asn Ala Trp Met Asn Ser Thr Met Arg Asn Phe Met
        115                 120                 125

Pro Ser Leu Thr Glu Ala Thr Ile Ser His Lys Pro Asp Gly Gly Pro
    130                 135                 140

Ser Met Pro Tyr Met His Ala Pro Gln Ser His Leu Val Thr Ser Asp
145                 150                 155                 160

Thr Tyr Ser Val Gln Leu Gln Met Thr Pro Ser Asn Ser Val Arg Gly
                165                 170                 175

Pro Val Thr Tyr Gln Gly Asn Tyr Gln Gly Asn Pro Gly Leu Asn His
            180                 185                 190

Ser Met Ala Gly Glu Leu Gly Trp Val Gln Cys Ala Ser Ser Glu Leu
        195                 200                 205

Thr Tyr Pro Asp Tyr Arg Pro Pro Lys Gln Tyr Pro Tyr Leu Pro
    210                 215                 220

Gln Ser Phe Val Gln Asp Thr Ser Val Gln Lys Gln Asn Phe Val Ser
225                 230                 235                 240

Ser Thr Ser Leu Gln Val Lys Asn Asn Gln Leu Pro Pro Ser Thr Gln
                245                 250                 255
```

```
Thr Leu Pro Ser Lys Arg Pro Val Pro Val Ser Ser Tyr Gln Tyr Ala
            260                 265                 270

Ala Glu Thr Ser Lys Arg Leu Pro Pro Pro Tyr Ser Cys Arg Tyr
        275                 280                 285

Gly Ser Gln His Val Gln Asn Ser Gln Ser Val Ser Arg His Leu Pro
290                 295                 300

Val Glu Val Pro Gln Ser Ser Glu Met His Ser Ser Glu Lys Lys Lys
305                 310                 315                 320

Asp Ala Tyr Lys Val Phe Gln Gln Gln Trp Gln Ser Thr Ser Lys Asn
                325                 330                 335

Val Ser Thr Ile Gly Lys Phe Cys Glu Leu Lys Ile Asn Thr Lys Gln
            340                 345                 350

Ser Tyr Asn Asp Ser Ala Gly Ser Ser Asp Gly Val His Thr Leu
        355                 360                 365

Val Gln Asn Asn Gln Glu Glu Arg Lys Tyr Ser Tyr Asn Pro Ser Thr
370                 375                 380

Asn Gln Ile Leu Asp Thr Asn Val Thr Lys Glu Lys Leu Val Arg Asp
385                 390                 395                 400

Ile Lys Ser Leu Val Glu Ile Lys Lys Lys Phe Ser Glu Leu Ala Arg
                405                 410                 415

Lys Ile Lys Ile Asn Lys Lys Leu Leu Met Ala Ala Gly Cys Ser Lys
            420                 425                 430

Thr Ala Asn Thr Ser Tyr Thr Glu Pro Thr Arg His Ser Glu Phe Ser
        435                 440                 445

Ala Lys Glu Met Ser Ala Lys Arg Asp Asn Gln Cys Ser Met Glu Leu
        450                 455                 460

Leu Ala Thr Cys Leu Ser Leu Trp Lys Asn Gln Pro Pro Lys Thr Thr
465                 470                 475                 480

Glu Glu Asn Val Ser Lys Pro Leu Glu Glu Lys Gln Tyr Asn Ala Ser
                485                 490                 495

Arg Thr Ser Thr Thr Ala Val Gly Pro Ser Asn Pro Met Asn Glu Val
        500                 505                 510

His Val Lys Asn Phe Cys Ser Gly Val Arg Asn Ser Gln Lys Ile Thr
        515                 520                 525

Thr Ser Ser Gln Thr Val Leu Ser Val Leu Thr Pro Val Tyr Asp Ser
530                 535                 540

Ser Asp Val Ala Val Gly Lys Gly Thr Glu Leu Gln Ile Ala Val Val
545                 550                 555                 560

Ser Pro Leu Ile Leu Ser Asp Val Ser Thr Val Pro Gly Lys Glu Leu
                565                 570                 575

Ala Pro Glu Val Val Ser Glu Thr Val Tyr Pro Val Lys Glu Gly
        580                 585                 590

Ser Val Cys Ser Leu Gln Asn Gln Gln Ala Glu Asn Ala Thr Val Thr
        595                 600                 605

Ala Gly Leu Pro Phe Asp Val Ile Arg Ala Val Ala Ser Ala Thr Val
        610                 615                 620

Ser Ala Glu Leu Ser Leu Pro Gly His Lys Glu Lys Gln His Lys Pro
625                 630                 635                 640

Thr Gln Ser Asp Leu Asp Ile Ala Asp Gly Ser Leu Gly Lys His Ser
                645                 650                 655

Pro Gln Gly Ala Glu Ala Leu Pro Asn Pro Arg Asp Ser Thr Ile Val
            660                 665                 670
```

```
Ser Gly Pro Ile Leu Gln Ile Glu Ser Ile Cys Ser Leu Ala Glu Gly
            675                 680                 685

Asp Val Ser Tyr Asn Ser Gln Ile Ala Glu Ile Phe Asn Ser Val Gln
    690                 695                 700

Asn Glu Pro Gln Lys Pro Ser Pro Asp Gln Gln Val Ile Asn Ser Gln
705                 710                 715                 720

Gln Glu Glu Gln Val Asp Lys Val Ala Glu Asn Lys Asp Leu Ser Phe
                725                 730                 735

Leu Lys Asp Lys Cys Met Gln Cys Thr Asp Val Pro His Glu Val Thr
            740                 745                 750

Glu Gln Pro Glu Pro Leu Gln Pro Leu Glu Thr Thr Ser Asp Glu Tyr
        755                 760                 765

Val Glu Ala Asn Gly Glu Ile Leu Glu Glu Ser Ser Lys Glu Asn Pro
    770                 775                 780

Gly Glu Lys Glu Met Thr Lys Asp Ile Leu Cys Ser Pro Ala Ala Val
785                 790                 795                 800

Gln Gln Asp Pro Gln Pro Gln Glu Ile Asp Thr Ala Ser Ser Lys Ser
                805                 810                 815

Gly His Ser Phe Ser Thr Val Asn Glu Ile Asn Asp Glu Asn Glu Pro
            820                 825                 830

Val Ser Tyr Leu His Asp Gln Leu Leu Glu Leu Leu Lys Glu Phe Pro
        835                 840                 845

Tyr Gly Ile Glu Thr Ile Ala Arg Pro Glu Val Tyr Val Gly Gln Gln
    850                 855                 860

Lys Thr His Glu Ile Leu Glu Asn Gln Thr Gly Ser Lys Thr Gly Asn
865                 870                 875                 880

Val Ser Gly Asp Asn Thr Asp Gln Ile Lys Ile Thr Val Leu Asn Ser
                885                 890                 895

Glu Gln Ile Lys Glu Leu Phe Pro Glu Asp Gln Pro Cys Asp Val
            900                 905                 910

Asp Lys Leu Ala Glu Pro Glu Asn Thr Lys Ile Ile Ala Glu Val Lys
        915                 920                 925

Ser Leu Cys Asp Ser Gln Val Pro Arg Glu Glu Ser His Asn Pro Gly
    930                 935                 940

Met Leu Asp Leu Glu Lys Asp Lys Ile His Cys Cys Ala Leu Gly Trp
945                 950                 955                 960

Leu Ser Met Val Tyr Glu Gly Val Pro Gln Cys Cys Ser Ser Met
                965                 970                 975

Glu Glu Lys Glu Lys Asp Gln Cys Ser Leu Glu Ile Ser Asn Cys Lys
            980                 985                 990

Gln Gly Glu Gln Ala Cys Asn Ser  Gly Ile Thr Ile Phe  Glu Ile Asn
        995                 1000                1005

Pro Ile  Ser Asn Asn Ser Lys  Ser Pro Leu Ile Gln  Glu Ser Glu
    1010                1015                1020

Lys Gly  His Phe Ser Asp Ile  His Gly Glu Lys Ile  Lys Thr Ser
    1025                1030                1035

Glu Thr  Lys Asn Ser Ser Ser  Pro Arg Val Glu Gln  Glu Leu Thr
    1040                1045                1050

Gly His  Phe Ser Met Lys Cys  Tyr Gln Lys Asp Lys  Ser Thr Thr
    1055                1060                1065

Lys Gln  Asp Ser Ser Leu Lys  Thr Glu Gln Lys Ile  Lys Asn Leu
    1070                1075                1080

Ser Ser  Lys Cys Asp Lys Pro  Asn Pro Leu Lys Ser  Ser Lys Ile
```

```
              1085                1090               1095

Pro Thr Pro Glu Thr Phe Asn Val Val Thr Ser Asn Ser Asp Lys
         1100                1105            1110

Asn Met Pro Ala Phe Ser Lys Gln Asp Ser Gln Gly Ser Leu Gln
         1115                1120            1125

Lys Lys His Leu Phe Gln Asp Ser Asp Pro Val Lys Gly His Val
         1130                1135            1140

Trp Leu Leu Pro Asn Lys Asp Pro Arg Arg Arg Asn Thr Phe Leu
         1145                1150            1155

Val Gln Ser Val Ser Pro Glu Lys Lys Lys Leu Lys Phe Lys Ser
         1160                1165            1170

Gly Ser Ser Lys Leu Lys Tyr Phe Glu Lys Arg Lys Met Asp His
         1175                1180            1185

Leu Leu Ile Ser Asp Val Glu Ile Lys Lys Lys Lys Tyr Glu Lys
         1190                1195            1200

Gln Glu Gln Asn Lys Asn Ala Gly Gly Thr Leu Lys Leu Cys Ser
         1205                1210            1215

Thr Leu Thr Glu Pro Asn Glu Arg Ala Cys Ala Lys Glu Lys Ile
         1220                1225            1230

Val Thr Asn Ser Glu Pro Ser Asp Ser Lys Gly Ser Ser Ser Lys
         1235                1240            1245

Ser Thr Arg Val Ile Thr Val Gln Glu Tyr Leu Gln Arg Lys Lys
         1250                1255            1260

Asp Lys His Val Ile Gly Asn Asn Ala Ser Lys Asn Ile Cys Val
         1265                1270            1275

Glu Asn Val Pro Cys Asp Ser Glu Pro Met Lys Ser Ser Lys His
         1280                1285            1290

Ser Ala Ser Pro Ser Leu Gly Lys Leu Ile Glu Gly Gln Gly Val
         1295                1300            1305

Ser Ala Glu Thr Leu Lys Glu Val Glu His Asn Ser Thr Ser His
         1310                1315            1320

Gly Lys Asn Leu Lys Thr His Arg Ser Glu Glu Thr Arg Pro Tyr
         1325                1330            1335

Ser Val Ser Asn Ser Lys Glu Lys Phe Tyr Arg Thr His Pro Asp
         1340                1345            1350

Lys Ser Tyr Ile Asp Lys Ala Lys Leu Glu Arg Leu Thr Ser Met
         1355                1360            1365

Ser Ser Lys Ser Ser Gln Leu Gln Val Lys Glu Lys Arg Lys Gln
         1370                1375            1380

Tyr Leu Asn Arg Val Ala Phe Lys Cys Thr Glu Gln Glu Ser Ile
         1385                1390            1395

Cys Leu Thr Lys Leu Asp Ser Ala Ser Lys Lys Leu Ser Lys Glu
         1400                1405            1410

Lys Glu Lys Ser Thr Ala Cys Ala Pro Met Thr Lys Asp Tyr Thr
         1415                1420            1425

His Lys Pro Met Leu Glu Phe Lys Leu Cys Pro Asp Val Leu Leu
         1430                1435            1440

Lys Asn Thr Ser Ser Ile Asp Lys Gly Asp Asp Pro Arg Pro Gly
         1445                1450            1455

Pro Glu Lys Glu Arg Ala Pro Val Gln Val Ser Gly Ile Lys Thr
         1460                1465            1470

Thr Lys Glu Asp Trp Leu Lys Cys Ile Pro Thr Arg Thr Lys Met
         1475                1480            1485
```

```
Pro Glu Ser Ser Glu Gln Thr Asp Arg Ala Asp Ser Arg Leu Ser
    1490            1495                1500

Lys Arg Ser Phe Ser Ala Asp Glu Phe Glu Thr Leu Gln Asn Pro
1505            1510                1515

Val Lys Asp Ser Asn Val Met Phe Arg Thr Phe Lys Lys Met Tyr
    1520            1525                1530

Leu Glu Lys Arg Ser Arg Ser Leu Gly Ser Ser Pro Val Lys
    1535            1540                1545

<210> SEQ ID NO 11
<211> LENGTH: 1515
<212> TYPE: PRT
<213> ORGANISM: Unknown
<220> FEATURE:
<223> OTHER INFORMATION: Cricetinae gen. sp.
<220> FEATURE:
<221> NAME/KEY: UNSURE
<222> LOCATION: (879)..(879)
<223> OTHER INFORMATION: Xaa may be any amino acid

<400> SEQUENCE: 11

Met Asn Trp Asn Ala Lys Pro Glu Asn Ala Ala Pro Asn Pro Tyr
1               5                   10                  15

Ser Lys Ser Gln Ser Ser Leu Leu Gln Gln Phe Leu Met Pro Ser Thr
                20                  25                  30

Thr Ser Gln Ser Ser Phe Ser Cys Leu Pro His Asn Gln Glu Ala Cys
            35                  40                  45

Ile Tyr Pro Thr Asn Ser Asn Ser Val Ser Gln Pro Leu Leu Asn Val
50                  55                  60

Arg Ser Phe Ile Asn Pro Pro Ile Ser Val Ser Asn Val His Asn Arg
65                  70                  75                  80

Thr Val Val Ala Ser Gln Thr Ser Val Glu Arg Val Thr Tyr Thr Asn
                85                  90                  95

Val Lys Gly Ala Gln Gln Pro Asn His Asn Leu Gln Thr Val Ser Ser
            100                 105                 110

Gly Val Val Gln Asn Ala Trp Met Asn Ser Thr Met Arg Asn Phe Met
        115                 120                 125

Pro Ser Leu Thr Glu Ala Thr Ile Ser His Lys Pro Asp Gly Gly Pro
130                 135                 140

Ser Met Pro Tyr Met His Ala Pro Gln Ser His Leu Val Thr Ser Asp
145                 150                 155                 160

Thr Tyr Ser Val Gln Leu Gln Met Thr Pro Ser Asn Ser Val Arg Gly
                165                 170                 175

Pro Val Thr Tyr Gln Gly Asn Tyr Gln Gly Asn Pro Gly Leu Asn His
            180                 185                 190

Ser Met Ala Gly Glu Leu Gly Trp Val Gln Cys Ala Ser Ser Glu Leu
        195                 200                 205

Thr Tyr Pro Asp Tyr Arg Pro Pro Lys Gln Tyr Pro Tyr Leu Pro
210                 215                 220

Gln Ser Phe Val Gln Asp Thr Ser Val Gln Lys Gln Asn Phe Val Ser
225                 230                 235                 240

Ser Thr Ser Leu Gln Val Lys Asn Asn Gln Leu Pro Pro Ser Thr Gln
                245                 250                 255

Thr Leu Pro Ser Lys Arg Pro Val Pro Val Ser Ser Tyr Gln Tyr Ala
            260                 265                 270

Ala Glu Thr Ser Lys Arg Leu Pro Pro Pro Pro Tyr Ser Cys Arg Tyr
```

```
            275                 280                 285
Gly Ser Gln His Val Gln Asn Ser Gln Ser Val Ser Arg His Leu Pro
290                 295                 300

Val Glu Val Pro Gln Ser Ser Glu Met His Ser Ser Glu Lys Lys Lys
305                 310                 315                 320

Asp Ala Tyr Lys Val Phe Gln Gln Gln Trp Gln Ser Thr Ser Lys Asn
                    325                 330                 335

Val Ser Thr Ile Gly Lys Phe Cys Glu Leu Lys Ile Asn Thr Lys Gln
                340                 345                 350

Ser Tyr Asn Asp Ser Ala Gly Ser Ser Asp Gly Val His Thr Leu
                    355                 360                 365

Val Gln Asn Asn Gln Glu Glu Arg Lys Tyr Ser Tyr Asn Pro Ser Thr
370                 375                 380

Asn Gln Ile Leu Asp Thr Asn Val Thr Lys Glu Lys Leu Val Arg Asp
385                 390                 395                 400

Ile Lys Ser Leu Val Glu Ile Ser Trp Ala Met Val Ala His Ser Glu
                    405                 410                 415

Phe Ser Ala Lys Glu Met Ser Ala Lys Arg Asp Asn Gln Cys Ser Met
                420                 425                 430

Glu Leu Leu Ala Thr Cys Leu Ser Leu Trp Lys Asn Gln Pro Pro Lys
                435                 440                 445

Thr Thr Glu Glu Asn Val Ser Lys Pro Leu Glu Lys Gln Tyr Asn
450                 455                 460

Ala Ser Arg Thr Ser Thr Thr Ala Val Gly Pro Ser Asn Pro Met Asn
465                 470                 475                 480

Glu Val His Val Lys Asn Phe Cys Ser Gly Val Arg Asn Ser Gln Lys
                    485                 490                 495

Ile Thr Thr Ser Ser Gln Thr Val Leu Ser Val Leu Thr Pro Val Tyr
                500                 505                 510

Asp Ser Ser Asp Val Ala Val Gly Lys Gly Thr Glu Leu Gln Ile Ala
                515                 520                 525

Val Val Ser Pro Leu Ile Leu Ser Asp Val Ser Thr Val Pro Gly Lys
                530                 535                 540

Glu Leu Ala Pro Glu Val Val Ser Glu Thr Val Tyr Pro Val Val Lys
545                 550                 555                 560

Glu Gly Ser Val Cys Ser Leu Gln Asn Gln Gln Ala Glu Asn Ala Thr
                565                 570                 575

Val Thr Ala Gly Leu Pro Phe Asp Val Ile Arg Ala Val Ala Ser Ala
                580                 585                 590

Thr Val Ser Ala Glu Leu Ser Leu Pro Gly His Lys Glu Lys Gln His
                595                 600                 605

Lys Pro Thr Gln Thr Asp Leu Asp Thr Ala Asp Gly Ser Leu Gly Lys
                610                 615                 620

His Ser Pro Gln Gly Ala Glu Ala Leu Pro Asn Pro Arg Asp Ser Thr
625                 630                 635                 640

Ile Val Ser Gly Pro Ile Leu Gln Ile Glu Ser Ile Cys Ser Leu Ala
                    645                 650                 655

Glu Gly Asp Val Ser Tyr Asn Ser Gln Ile Ala Glu Ile Phe Asn Ser
                660                 665                 670

Val Gln Asn Glu Pro Gln Lys Pro Ser Pro Asp Gln Gln Val Ile Asn
                675                 680                 685

Ser Gln Gln Glu Glu Gln Val Asp Lys Val Ala Glu Asn Lys Asp Leu
690                 695                 700
```

```
Ser Phe Leu Lys Asp Lys Cys Met Gln Cys Thr Asp Val Pro His Glu
705                 710                 715                 720

Val Thr Glu Gln Pro Glu Pro Leu Gln Pro Leu Glu Thr Thr Ser Asp
                725                 730                 735

Glu Tyr Val Glu Ala Asn Gly Glu Ile Leu Glu Glu Ser Ser Lys Glu
            740                 745                 750

Asn Pro Gly Glu Lys Glu Met Thr Lys Asp Ile Leu Cys Ser Pro Ala
        755                 760                 765

Ala Val Gln Gln Asp Pro Gln Pro Gln Glu Ile Asp Thr Ala Ser Ser
770                 775                 780

Lys Ser Gly His Ser Phe Ser Thr Val Asn Glu Ile Asn Asp Glu Asn
785                 790                 795                 800

Glu Pro Val Ser Tyr Leu His Asp Gln Leu Leu Glu Leu Leu Lys Glu
                805                 810                 815

Phe Pro Tyr Gly Ile Glu Thr Ile Ala Arg Pro Glu Val Tyr Val Gly
            820                 825                 830

Gln Gln Lys Thr His Glu Ile Leu Glu Asn Gln Thr Gly Ser Lys Thr
        835                 840                 845

Gly Asn Val Ser Gly Asp Asn Thr Asp Gln Ile Lys Ile Thr Val Leu
850                 855                 860

Asn Ser Glu Gln Ile Lys Glu Leu Phe Pro Glu Asp Gln Xaa Val
865                 870                 875                 880

Asp Lys Leu Ala Glu Pro Glu Asn Thr Lys Ile Ile Ala Glu Val Lys
                885                 890                 895

Ser Leu Cys Asp Ser Gln Val Pro Arg Glu Glu Ser His Asn Pro Gly
            900                 905                 910

Met Leu Asp Leu Glu Lys Asp Lys Ile His Cys Cys Ala Leu Gly Trp
        915                 920                 925

Leu Ser Met Val Tyr Glu Gly Val Pro Gln Cys Gln Cys Ser Ser Met
930                 935                 940

Glu Glu Lys Glu Lys Asp Gln Cys Ser Leu Glu Ile Ser Asn Cys Lys
945                 950                 955                 960

Gln Gly Glu Gln Ala Cys Asn Ser Gly Ile Thr Ile Phe Glu Ile Asn
                965                 970                 975

Pro Ile Ser Asn Asn Ser Lys Ser Pro Leu Ile Gln Glu Ser Glu Lys
            980                 985                 990

Gly His Phe Ser Asp Ile His Gly Glu Lys Ile Lys Thr Ser Glu Thr
        995                 1000                1005

Lys Asn Ser Ser Ser Pro Arg Val Glu Gln Glu Leu Thr Gly His
1010                1015                1020

Phe Ser Met Lys Cys Tyr Gln Lys Asp Lys Ser Thr Thr Lys Gln
    1025                1030                1035

Asp Ser Ser Leu Lys Thr Glu Gln Lys Ile Lys Asn Leu Ser Ser
    1040                1045                1050

Lys Cys Asp Lys Pro Asn Pro Leu Lys Ser Ser Lys Ile Pro Thr
    1055                1060                1065

Pro Glu Thr Phe Asn Val Val Thr Ser Asn Ser Asp Lys Asn Met
    1070                1075                1080

Pro Ala Phe Ser Lys Gln Asp Ser Gln Gly Ser Leu Gln Lys Lys
    1085                1090                1095

His Leu Phe Gln Asp Ser Asp Pro Val Lys Gly His Val Trp Leu
    1100                1105                1110
```

```
Leu Pro Asn Lys Asp Pro Arg Arg Asn Thr Phe Leu Val Gln
1115                1120                1125

Ser Val Ser Pro Glu Lys Lys Leu Lys Phe Lys Ser Gly Ser
1130                1135                1140

Ser Lys Leu Lys Tyr Phe Glu Lys Arg Lys Met Asp His Leu Leu
1145                1150                1155

Ile Ser Asp Val Glu Ile Lys Lys Lys Lys Tyr Glu Lys Gln Glu
1160                1165                1170

Gln Asn Lys Asn Ala Gly Gly Thr Leu Lys Leu Cys Ser Thr Leu
1175                1180                1185

Thr Glu Pro Asn Glu Arg Ala Cys Ala Lys Glu Lys Ile Val Thr
1190                1195                1200

Asn Ser Glu Pro Ser Asp Ser Lys Gly Ser Ser Lys Ser Thr
1205                1210                1215

Arg Val Ile Thr Val Gln Glu Tyr Leu Gln Arg Lys Lys Asp Lys
1220                1225                1230

His Val Ile Gly Asn Asn Ala Ser Lys Asn Ile Cys Val Glu Asn
1235                1240                1245

Val Pro Cys Asp Ser Glu Pro Met Lys Ser Ser Lys His Ser Ala
1250                1255                1260

Ser Pro Ser Leu Gly Lys Leu Ile Glu Gly Gln Gly Val Ser Ala
1265                1270                1275

Glu Thr Leu Lys Glu Val Glu His Asn Ser Ser Ser His Gly Lys
1280                1285                1290

Asn Leu Lys Thr His Arg Ser Glu Glu Thr Arg Pro Tyr Ser Val
1295                1300                1305

Ser Asn Ser Lys Glu Lys Phe Tyr Arg Thr His Pro Asp Lys Ser
1310                1315                1320

Tyr Ile Asp Lys Ala Lys Leu Glu Arg Leu Thr Ser Met Ser Ser
1325                1330                1335

Lys Ser Ser Gln Leu Gln Val Lys Glu Lys Arg Lys Gln Tyr Leu
1340                1345                1350

Asn Arg Val Ala Phe Lys Cys Thr Glu Gln Glu Ser Ile Cys Leu
1355                1360                1365

Thr Lys Leu Asp Ser Ala Ser Lys Lys Leu Ser Lys Glu Lys Glu
1370                1375                1380

Lys Ser Thr Ala Cys Ala Pro Met Thr Lys Asp Tyr Thr His Lys
1385                1390                1395

Pro Met Leu Glu Phe Lys Leu Cys Pro Asp Val Leu Leu Lys Asn
1400                1405                1410

Thr Ser Ser Ile Asp Lys Gly Asp Asp Pro Arg Pro Gly Pro Glu
1415                1420                1425

Lys Glu Arg Ala Pro Val Gln Val Ser Gly Ile Lys Thr Thr Lys
1430                1435                1440

Glu Asp Trp Leu Lys Cys Ile Pro Thr Arg Thr Lys Met Pro Glu
1445                1450                1455

Ser Ser Glu Gln Thr Asp Arg Ala Asp Ser Arg Leu Ser Lys Arg
1460                1465                1470

Ser Phe Ser Ala Asp Glu Phe Glu Thr Leu Gln Asn Pro Val Lys
1475                1480                1485

Asp Ser Asn Val Met Phe Arg Thr Phe Lys Lys Met Tyr Leu Glu
1490                1495                1500

Lys Arg Ser Arg Ser Leu Gly Ser Ser Pro Val Lys
```

```
              1505                1510                1515

<210> SEQ ID NO 12
<211> LENGTH: 1747
<212> TYPE: PRT
<213> ORGANISM: Homo sapiens

<400> SEQUENCE: 12

Met Asn Trp Asn Glu Lys Pro Lys Ser Ala Thr Leu Pro Pro Leu Tyr
1               5                   10                  15

Pro Lys Ser Gln Pro Pro Phe Leu His Gln Ser Leu Ile Asn Gln Ile
            20                  25                  30

Thr Thr Thr Ser Gln Ser Ser Phe Ser Tyr Pro Gly Ser Asn Gln Glu
        35                  40                  45

Ala Cys Met Tyr Pro Gly Asn Ser Asn Pro Ile Ser Gln Pro Leu Leu
50                  55                  60

Asn Ile Gln Asn Tyr Pro Gln Gln Ile Ser Val Ser Asp Met His Asn
65                  70                  75                  80

Gly Thr Val Val Ala Ser His Thr Ser Val Glu Arg Ile Thr Tyr Ala
                85                  90                  95

Asn Val Asn Gly Pro Lys Gln Leu Thr His Asn Leu Gln Met Ser Ser
            100                 105                 110

Gly Val Thr Gln Asn Val Trp Leu Asn Ser Pro Met Arg Asn Pro Val
        115                 120                 125

His Ser His Ile Gly Ala Thr Val Ser His Gln Thr Asp Phe Gly Ala
130                 135                 140

Asn Val Pro Asn Met Pro Ala Leu Gln Ser Gln Leu Ile Thr Ser Asp
145                 150                 155                 160

Thr Tyr Ser Met Gln Met Gln Met Ile Pro Ser Asn Ser Thr Arg Leu
                165                 170                 175

Pro Val Ala Tyr Gln Gly Asn Gln Gly Leu Asn Gln Ser Phe Ser Glu
            180                 185                 190

Gln Gln Val Asp Trp Thr Gln Gln Cys Ile Ser Lys Gly Leu Thr Tyr
        195                 200                 205

Pro Asp Tyr Arg Pro Pro Lys Leu Tyr Arg Tyr Ser Pro Gln Ser
210                 215                 220

Phe Leu Pro Asp Ser Thr Ile Gln Lys Gln Asn Phe Ile Pro His Thr
225                 230                 235                 240

Ser Leu Gln Val Lys Asn Ser Gln Leu Leu Asn Ser Val Leu Thr Leu
                245                 250                 255

Pro Ser Arg Gln Thr Ser Ala Val Pro Ser Gln Gln Tyr Ala Thr Gln
            260                 265                 270

Thr Asp Lys Arg Pro Pro Pro Pro Tyr Asn Cys Arg Tyr Gly Ser
        275                 280                 285

Gln Pro Leu Gln Ser Thr Gln His Ile Thr Lys His Leu Ser Met Glu
290                 295                 300

Val Pro Gln Ser Arg Glu Met Leu Ser Ser Glu Ile Arg Thr Ser Phe
305                 310                 315                 320

Gln Gln Gln Trp Gln Asn Pro Asn Glu Asn Val Ser Thr Ile Gly Asn
                325                 330                 335

Phe Thr Asn Leu Lys Val Asn Thr Asn Ser Lys Gln Pro Phe Asn Ser
            340                 345                 350

Pro Ile Arg Ser Ser Val Asp Gly Val Gln Thr Leu Ala Gln Thr Asn
        355                 360                 365
```

-continued

Glu Glu Lys Ile Met Asp Ser Cys Asn Pro Thr Ser Asn Gln Val Leu
370                 375                 380

Asp Thr Ser Val Ala Lys Glu Lys Leu Val Arg Asp Ile Lys Thr Leu
385                 390                 395                 400

Val Glu Ile Lys Gln Lys Phe Ser Glu Leu Ala Arg Lys Ile Lys Ile
        405                 410                 415

Asn Lys Asp Leu Leu Met Ala Ala Gly Cys Ile Lys Met Thr Asn Thr
            420                 425                 430

Ser Tyr Ser Glu Pro Ala Gln Asn Ser Lys Leu Ser Leu Lys Gln Thr
        435                 440                 445

Ala Lys Ile Gln Ser Gly Pro Gln Ile Thr Pro Val Met Pro Glu Asn
450                 455                 460

Ala Glu Arg Gln Thr Pro Thr Val Val Glu Ser Ala Glu Thr Asn Lys
465                 470                 475                 480

Thr Gln Cys Met Leu Asn Ser Asp Ile Gln Glu Val Asn Cys Arg Arg
            485                 490                 495

Phe Asn Gln Val Asp Ser Val Leu Pro Asn Pro Val Tyr Ser Glu Lys
            500                 505                 510

Arg Pro Met Pro Asp Ser Ser His Asp Val Lys Val Leu Thr Ser Lys
        515                 520                 525

Thr Ser Ala Val Glu Met Thr Gln Ala Val Leu Asn Thr Gln Leu Ser
    530                 535                 540

Ser Glu Asn Val Thr Lys Val Glu Gln Asn Ser Pro Ala Val Cys Glu
545                 550                 555                 560

Thr Ile Ser Val Pro Lys Ser Met Ser Thr Glu Glu Tyr Lys Ser Lys
                565                 570                 575

Ile Gln Asn Glu Asn Met Leu Leu Leu Ala Leu Leu Ser Gln Ala Arg
            580                 585                 590

Lys Thr Gln Lys Thr Val Leu Lys Asp Ala Asn Gln Thr Ile Gln Asp
        595                 600                 605

Ser Lys Pro Asp Ser Cys Glu Met Asn Pro Asn Thr Gln Met Thr Gly
610                 615                 620

Asn Gln Leu Asn Leu Lys Asn Met Glu Thr Pro Ser Thr Ser Asn Val
625                 630                 635                 640

Ser Gly Arg Val Leu Asp Asn Ser Phe Cys Ser Gly Gln Glu Ser Ser
                645                 650                 655

Thr Lys Gly Met Pro Ala Lys Ser Asp Ser Ser Cys Ser Met Glu Val
            660                 665                 670

Leu Ala Thr Cys Leu Ser Leu Trp Lys Lys Gln Pro Ser Asp Thr Ala
            675                 680                 685

Lys Glu Lys Glu Cys Asp Lys Leu Arg Thr Asn Thr Thr Ala Val Gly
690                 695                 700

Ile Ser Lys Pro Ala Asn Ile His Val Lys Ser Pro Cys Ser Val Val
705                 710                 715                 720

Gly Asn Ser Asn Ser Gln Asn Lys Ile Ser Pro Ser Gln Gln Thr
                725                 730                 735

Ala Leu Ser Met Val Met His Asn Tyr Glu Ser Ser Gly Ile Asn Ile
            740                 745                 750

Thr Lys Gly Thr Glu Leu Gln Ile Ala Val Val Ser Pro Leu Val Leu
        755                 760                 765

Ser Glu Val Lys Thr Leu Ser Val Lys Gly Ile Thr Pro Ala Val Leu
770                 775                 780

Pro Glu Thr Val Tyr Pro Val Ile Lys Glu Gly Ser Val Cys Ser Leu

-continued

```
            785                 790                 795                 800
    Gln Asn Gln Leu Ala Glu Asn Ala Lys Ala Thr Ala Ala Leu Lys Val
                    805                 810                 815

Asp Val Ser Gly Pro Val Ala Ser Thr Ala Thr Ser Thr Lys Ile Phe
                    820                 825                 830

Pro Leu Thr Gln Lys Glu Lys Gln Asn Glu Ser Thr Asn Gly Asn Ser
                    835                 840                 845

Glu Val Thr Pro Asn Val Asn Gln Gly Lys His Asn Lys Leu Glu Ser
                    850                 855                 860

Ala Ile His Ser Pro Met Asn Asp Gln Gln Ile Ser Gln Glu Ser Arg
    865                 870                 875                 880

Asn Ser Thr Val Val Ser Ser Asp Thr Leu Gln Ile Asp Asn Ile Cys
                    885                 890                 895

Ser Leu Val Glu Gly Asp Thr Ser Tyr Asn Ser Gln Ile Ala Lys Ile
                    900                 905                 910

Phe Ser Ser Leu Pro Leu Lys Met Val Glu Pro Gln Lys Pro Ser Leu
                    915                 920                 925

Pro Asn Gln Gln Gly Ile Gly Ser Arg Glu Pro Glu Lys Gln Leu Asp
                    930                 935                 940

Asn Thr Thr Glu Asn Lys Asp Phe Gly Phe Gln Lys Asp Lys Pro Val
    945                 950                 955                 960

Gln Cys Thr Asp Val Ser His Lys Ile Cys Asp Gln Ser Lys Ser Glu
                    965                 970                 975

Pro Pro Leu Glu Ser Ser Phe Asn Asn Leu Glu Thr Asn Arg Val Ile
                    980                 985                 990

Leu Glu Lys Ser Ser Leu Glu His Ala Thr Glu Lys Ser Thr Ala Asn
                    995                 1000                1005

Asp Thr Cys Ser Ser Ala Ala Ile Gln Glu Asp Ile Tyr Pro Gln
                    1010                1015                1020

Glu Ile Asp Ala Ser Ser Asn Tyr Thr Pro Gln Asp Pro Ala Arg
                    1025                1030                1035

Asn Glu Ile His Ser Asp Lys Ala Pro Val Leu Tyr Leu His Asp
                    1040                1045                1050

Gln Leu Ser Glu Leu Leu Lys Glu Phe Pro Tyr Gly Ile Glu Ala
                    1055                1060                1065

Val Asn Thr Arg Glu Gly Ser Val Gly Gln Gln Thr Thr Tyr Gln
                    1070                1075                1080

Thr Ser Glu Asp Gln Thr Ala Asp Lys Thr Ser Ser Asp Ser Lys
                    1085                1090                1095

Asp Pro Ala Asp Gln Ile Gln Ile Thr Ile Leu Ser Ser Glu Gln
                    1100                1105                1110

Met Lys Glu Ile Phe Pro Glu Gln Asp Asp Gln Pro Tyr Val Val
                    1115                1120                1125

Asp Lys Leu Ala Glu Pro Gln Lys Glu Pro Ile Thr Glu Val
                    1130                1135                1140

Val Ser Gln Cys Asp Leu Gln Ala Pro Ala Ala Gly Gln Ser Arg
                    1145                1150                1155

Asp Ser Val Ile Leu Asp Ser Glu Lys Ala Asp Ile His Cys Cys
                    1160                1165                1170

Ala Leu Gly Trp Leu Ser Met Val Tyr Glu Gly Val Pro Gln Cys
                    1175                1180                1185

Gln Cys Asn Ser Ile Lys Asn Ser Ser Ser Glu Glu Glu Lys Gln
                    1190                1195                1200
```

-continued

```
Lys Glu Gln Cys Ser Pro Leu Asp Thr Asn Ser Cys Lys Gln Gly
1205                1210                1215

Glu Arg Thr Ser Asp Arg Asp Val Thr Val Val Gln Phe Lys Ser
1220                1225                1230

Leu Val Asn Asn Pro Lys Thr Pro Pro Asp Gly Lys Ser His Phe
1235                1240                1245

Pro Glu Leu Gln Asp Asp Ser Arg Lys Asp Thr Pro Lys Thr Lys
1250                1255                1260

His Lys Ser Leu Pro Arg Thr Glu Gln Glu Leu Val Ala Gly Gln
1265                1270                1275

Phe Ser Ser Lys Cys Asp Lys Leu Asn Pro Leu Gln Asn His Lys
1280                1285                1290

Arg Lys Lys Leu Arg Phe His Glu Val Thr Phe His Ser Ser Asn
1295                1300                1305

Lys Met Thr Ala Ser Tyr Glu Gln Ala Ser Gln Glu Thr Arg Gln
1310                1315                1320

Lys Lys His Val Thr Gln Asn Ser Arg Pro Leu Lys Thr Lys Thr
1325                1330                1335

Ala Phe Leu Pro Asn Lys Asp Val Tyr Lys Lys His Ser Ser Leu
1340                1345                1350

Gly Gln Ser Leu Ser Pro Glu Lys Ile Lys Leu Lys Leu Lys Ser
1355                1360                1365

Val Ser Phe Lys Gln Lys Arg Lys Leu Asp Gln Gly Asn Val Leu
1370                1375                1380

Asp Met Glu Val Lys Lys Lys His Asp Lys Gln Glu Gln Lys
1385                1390                1395

Gly Ser Val Gly Ala Thr Phe Lys Leu Gly Asp Ser Leu Ser Asn
1400                1405                1410

Pro Asn Glu Arg Ala Ile Val Lys Glu Lys Met Val Ser Asn Thr
1415                1420                1425

Lys Ser Val Asp Thr Lys Ala Ser Ser Ser Lys Phe Ser Arg Ile
1430                1435                1440

Leu Thr Pro Lys Glu Tyr Leu Gln Arg Gln Lys His Lys Glu Ala
1445                1450                1455

Leu Ser Asn Lys Ala Ser Lys Lys Ile Cys Val Lys Asn Val Pro
1460                1465                1470

Cys Asp Ser Glu His Met Arg Pro Ser Lys Leu Ala Val Gln Val
1475                1480                1485

Glu Ser Cys Gly Lys Ser Asn Glu Lys His Ser Ser Gly Val Gln
1490                1495                1500

Thr Ser Lys Glu Ser Leu Asn Gly Leu Thr Ser His Gly Lys Asn
1505                1510                1515

Leu Lys Ile His His Ser Gln Glu Ser Lys Thr Tyr Asn Ile Leu
1520                1525                1530

Arg Asn Val Lys Glu Lys Val Gly Gly Lys Gln Pro Asp Lys Ile
1535                1540                1545

Trp Ile Asp Lys Thr Lys Leu Asp Lys Leu Thr Asn Ile Ser Asn
1550                1555                1560

Glu Ala Gln Phe Ser Gln Met Pro Pro Gln Val Lys Asp Gln Lys
1565                1570                1575

Lys Leu Tyr Leu Asn Arg Val Gly Phe Lys Cys Thr Glu Arg Glu
1580                1585                1590
```

```
Ser Ile Ser Leu Thr Lys Leu Glu Ser Ser Pro Arg Lys Leu His
    1595                1600                1605

Lys Asp Lys Arg Gln Glu Asn Lys His Lys Thr Phe Leu Pro Val
    1610                1615                1620

Lys Gly Asn Thr Glu Lys Ser Asn Met Leu Glu Phe Lys Leu Cys
    1625                1630                1635

Pro Asp Ile Leu Leu Lys Asn Thr Asn Ser Val Glu Glu Arg Lys
    1640                1645                1650

Asp Val Lys Pro His Pro Arg Lys Glu Gln Ala Pro Leu Gln Val
    1655                1660                1665

Ser Gly Ile Lys Ser Thr Lys Glu Asp Trp Leu Lys Phe Val Ala
    1670                1675                1680

Thr Lys Lys Arg Thr Gln Lys Asp Ser Gln Glu Arg Asp Asn Val
    1685                1690                1695

Asn Ser Arg Leu Ser Lys Arg Ser Phe Ser Ala Asp Gly Phe Glu
    1700                1705                1710

Met Leu Gln Asn Pro Val Lys Asp Ser Lys Glu Met Phe Gln Thr
    1715                1720                1725

Tyr Lys Gln Met Tyr Leu Glu Lys Arg Ser Arg Ser Leu Gly Ser
    1730                1735                1740

Ser Pro Val Lys
    1745

<210> SEQ ID NO 13
<211> LENGTH: 1747
<212> TYPE: PRT
<213> ORGANISM: Homo sapiens

<400> SEQUENCE: 13

Met Asn Trp Asn Glu Lys Pro Lys Ser Ala Thr Leu Pro Pro Leu Tyr
1               5                   10                  15

Pro Lys Ser Gln Pro Pro Phe Leu His Gln Ser Leu Ile Asn Gln Ile
                20                  25                  30

Thr Thr Thr Ser Gln Ser Ser Phe Ser Tyr Pro Gly Ser Asn Gln Glu
            35                  40                  45

Ala Cys Met Tyr Pro Gly Asn Ser Asn Pro Ile Ser Gln Pro Leu Leu
        50                  55                  60

Asn Ile Gln Asn Tyr Pro Gln Gln Ile Ser Val Ser Asp Met His Asn
65                  70                  75                  80

Gly Thr Val Val Ala Ser His Thr Ser Val Glu Arg Ile Thr Tyr Ala
                85                  90                  95

Asn Val Asn Gly Pro Lys Gln Leu Thr His Asn Leu Gln Met Ser Ser
            100                 105                 110

Gly Val Thr Gln Asn Val Trp Leu Asn Ser Pro Met Arg Asn Pro Val
        115                 120                 125

His Ser His Ile Gly Ala Thr Val Ser His Gln Thr Asp Phe Gly Ala
130                 135                 140

Asn Val Pro Asn Met Pro Ala Leu Gln Ser Gln Leu Ile Thr Ser Asp
145                 150                 155                 160

Thr Tyr Ser Met Gln Met Gln Met Ile Pro Ser Asn Ser Thr Arg Leu
                165                 170                 175

Pro Val Ala Tyr Gln Gly Asn Gln Gly Leu Asn Gln Ser Phe Ser Glu
            180                 185                 190

Gln Gln Val Asp Trp Thr Gln Gln Cys Ile Ser Lys Gly Leu Thr Tyr
        195                 200                 205
```

```
Pro Asp Tyr Arg Pro Pro Lys Leu Tyr Arg Tyr Ser Pro Gln Ser
    210                 215                 220

Phe Leu Pro Asp Ser Thr Ile Gln Lys Gln Asn Phe Ile Pro His Thr
225                 230                 235                 240

Ser Leu Gln Val Lys Asn Ser Gln Leu Leu Asn Ser Val Leu Thr Leu
                245                 250                 255

Pro Ser Arg Gln Thr Ser Ala Val Pro Ser Gln Gln Tyr Ala Thr Gln
                260                 265                 270

Thr Asp Lys Arg Pro Pro Pro Tyr Asn Cys Arg Tyr Gly Ser
            275             280             285

Gln Pro Leu Gln Ser Thr Gln His Ile Thr Lys His Leu Ser Met Glu
    290                 295                 300

Val Pro Gln Ser Arg Glu Met Leu Ser Ser Glu Ile Arg Thr Ser Phe
305                 310                 315                 320

Gln Gln Gln Trp Gln Asn Pro Asn Glu Asn Val Ser Thr Ile Gly Asn
                325                 330                 335

Phe Thr Asn Leu Lys Val Asn Thr Asn Ser Lys Gln Pro Phe Asn Ser
                340                 345                 350

Pro Ile Arg Ser Ser Val Asp Gly Val Gln Thr Leu Ala Gln Thr Asn
                355                 360                 365

Glu Glu Lys Ile Met Asp Ser Cys Asn Pro Thr Ser Asn Gln Val Leu
370                 375                 380

Asp Thr Ser Val Ala Lys Glu Lys Leu Val Arg Asp Ile Lys Thr Leu
385                 390                 395                 400

Val Glu Ile Lys Gln Lys Phe Ser Glu Leu Ala Arg Lys Ile Lys Ile
                405                 410                 415

Asn Lys Asp Leu Leu Met Ala Ala Gly Cys Ile Lys Met Thr Asn Thr
                420                 425                 430

Ser Tyr Ser Glu Pro Ala Gln Asn Ser Lys Leu Ser Leu Lys Gln Thr
    435                 440                 445

Ala Lys Ile Gln Ser Gly Pro Gln Ile Thr Pro Val Met Pro Glu Asn
450                 455                 460

Ala Glu Arg Gln Thr Pro Thr Val Val Glu Ser Ala Glu Thr Asn Lys
465                 470                 475                 480

Thr Gln Cys Met Leu Asn Ser Asp Ile Gln Glu Val Asn Cys Arg Arg
                485                 490                 495

Phe Asn Gln Val Asp Ser Val Leu Pro Asn Pro Val Tyr Ser Glu Lys
                500                 505                 510

Arg Pro Met Pro Asp Pro Ser His Asp Val Lys Val Leu Thr Ser Lys
    515                 520                 525

Thr Ser Ala Val Glu Met Thr Gln Ala Val Leu Asn Thr Gln Leu Ser
530                 535                 540

Ser Glu Asn Val Thr Lys Val Glu Gln Asn Ser Pro Ala Val Cys Glu
545                 550                 555                 560

Thr Ile Ser Val Pro Lys Ser Met Ser Thr Glu Glu Tyr Lys Ser Lys
                565                 570                 575

Ile Gln Asn Glu Asn Met Leu Leu Leu Ala Leu Leu Ser Gln Ala Arg
                580                 585                 590

Lys Thr Gln Lys Thr Val Leu Lys Asp Ala Asn Gln Thr Ile Gln Asp
        595                 600                 605

Ser Lys Pro Asp Ser Cys Glu Met Asn Pro Asn Thr Gln Met Thr Gly
610                 615                 620
```

```
Asn Gln Leu Asn Leu Lys Asn Met Glu Thr Pro Ser Thr Ser Asn Val
625                 630                 635                 640

Ser Gly Arg Val Leu Asp Asn Ser Phe Cys Ser Gly Gln Glu Ser Ser
                645                 650                 655

Thr Lys Gly Met Pro Ala Lys Ser Asp Ser Ser Cys Ser Met Glu Val
            660                 665                 670

Leu Ala Thr Cys Leu Ser Leu Trp Lys Lys Gln Pro Ser Asp Thr Ala
        675                 680                 685

Lys Glu Lys Glu Cys Asp Lys Leu Arg Thr Asn Thr Thr Ala Val Gly
690                 695                 700

Ile Ser Lys Pro Ala Asn Ile His Val Lys Ser Pro Cys Ser Val Val
705                 710                 715                 720

Gly Asn Ser Asn Ser Gln Asn Lys Ile Ser Asn Pro Ser Gln Gln Thr
                725                 730                 735

Ala Leu Ser Met Val Met His Asn Tyr Glu Ser Ser Gly Ile Asn Ile
            740                 745                 750

Thr Lys Gly Thr Glu Leu Gln Ile Ala Val Val Ser Pro Leu Val Leu
        755                 760                 765

Ser Glu Val Lys Thr Leu Ser Val Lys Gly Ile Thr Pro Ala Val Leu
770                 775                 780

Pro Glu Thr Val Tyr Pro Val Ile Lys Glu Gly Ser Val Cys Ser Leu
785                 790                 795                 800

Gln Asn Gln Leu Ala Glu Asn Ala Lys Ala Thr Ala Ala Leu Lys Val
                805                 810                 815

Asp Val Ser Gly Pro Val Ala Ser Thr Ala Thr Ser Thr Lys Ile Phe
            820                 825                 830

Pro Leu Thr Gln Lys Glu Lys Gln Asn Glu Ser Thr Asn Gly Asn Ser
        835                 840                 845

Glu Val Thr Pro Asn Val Asn Gln Gly Lys His Asn Lys Leu Glu Ser
850                 855                 860

Ala Ile His Ser Pro Met Asn Asp Gln Gln Ile Ser Gln Glu Ser Arg
865                 870                 875                 880

Asn Ser Thr Val Val Ser Ser Asp Thr Leu Gln Ile Asp Asn Ile Cys
                885                 890                 895

Ser Leu Val Glu Gly Asp Thr Ser Tyr Asn Ser Gln Ile Ala Lys Ile
            900                 905                 910

Phe Ser Ser Leu Pro Leu Lys Met Val Glu Pro Gln Lys Pro Ser Leu
        915                 920                 925

Pro Asn Gln Gln Gly Ile Gly Ser Arg Glu Pro Glu Lys Gln Leu Asp
930                 935                 940

Asn Thr Thr Glu Asn Lys Asp Phe Gly Phe Gln Lys Asp Lys Pro Val
945                 950                 955                 960

Gln Cys Thr Asp Val Ser His Lys Ile Cys Asp Gln Ser Lys Ser Glu
                965                 970                 975

Pro Pro Leu Glu Ser Ser Phe Asn Asn Leu Glu Thr Asn Arg Val Ile
            980                 985                 990

Leu Glu Lys Ser Ser Leu Glu His Ala Thr Glu Lys Ser Thr Ala Asn
        995                 1000                1005

Asp Thr Cys Ser Ser Ala Ala Ile Gln Glu Asp Ile Tyr Pro Gln
        1010                1015                1020

Glu Ile Asp Ala Ser Ser Asn Tyr Thr Pro Gln Asp Pro Ala Arg
        1025                1030                1035

Asn Glu Ile His Ser Asp Lys Ala Pro Val Leu Tyr Leu His Asp
```

-continued

```
            1040                1045                1050
Gln Leu Ser Glu Leu Leu Lys Glu Phe Pro Tyr Gly Ile Glu Ala
    1055                1060                1065
Val Asn Thr Arg Glu Gly Ser Val Gly Gln Gln Thr Thr Tyr Gln
    1070                1075                1080
Thr Ser Glu Asp Gln Thr Ala Asp Lys Thr Ser Ser Asp Ser Lys
    1085                1090                1095
Asp Pro Ala Asp Gln Ile Gln Ile Thr Ile Leu Ser Ser Glu Gln
    1100                1105                1110
Met Lys Glu Ile Phe Pro Glu Gln Asp Asp Gln Pro Tyr Val Val
    1115                1120                1125
Asp Lys Leu Ala Glu Pro Gln Lys Glu Glu Pro Ile Thr Glu Val
    1130                1135                1140
Val Ser Gln Cys Asp Leu Gln Ala Pro Ala Ala Gly Gln Ser Arg
    1145                1150                1155
Asp Ser Val Ile Leu Asp Ser Glu Lys Asp Asp Ile His Cys Cys
    1160                1165                1170
Ala Leu Gly Trp Leu Ser Met Val Tyr Glu Gly Val Pro Gln Cys
    1175                1180                1185
Gln Cys Asn Ser Ile Lys Asn Ser Ser Ser Glu Glu Glu Lys Gln
    1190                1195                1200
Lys Glu Gln Cys Ser Pro Leu Asp Thr Asn Ser Cys Lys Gln Gly
    1205                1210                1215
Glu Arg Thr Ser Asp Arg Asp Val Thr Val Val Gln Phe Lys Ser
    1220                1225                1230
Leu Val Asn Asn Pro Lys Thr Pro Pro Asp Gly Lys Ser His Phe
    1235                1240                1245
Pro Glu Leu Gln Asp Asp Ser Arg Lys Asp Thr Pro Lys Thr Lys
    1250                1255                1260
His Lys Ser Leu Pro Arg Thr Glu Gln Glu Leu Val Ala Gly Gln
    1265                1270                1275
Phe Ser Ser Lys Cys Asp Lys Leu Asn Pro Leu Gln Asn His Lys
    1280                1285                1290
Arg Lys Lys Leu Arg Phe His Glu Val Thr Phe His Ser Ser Asn
    1295                1300                1305
Lys Met Thr Ala Ser Tyr Glu Gln Ala Ser Gln Glu Thr Arg Gln
    1310                1315                1320
Lys Lys His Val Thr Gln Asn Ser Arg Pro Leu Lys Thr Lys Thr
    1325                1330                1335
Ala Phe Leu Pro Asn Lys Asp Val Tyr Lys Lys His Ser Ser Leu
    1340                1345                1350
Gly Gln Ser Leu Ser Pro Glu Lys Ile Lys Leu Lys Leu Lys Ser
    1355                1360                1365
Val Ser Phe Lys Gln Lys Arg Lys Leu Asp Gln Gly Asn Val Leu
    1370                1375                1380
Asp Met Glu Val Lys Lys Lys His Asp Lys Gln Glu Gln Lys
    1385                1390                1395
Gly Ser Val Gly Ala Thr Phe Lys Leu Gly Asp Ser Leu Ser Asn
    1400                1405                1410
Pro Asn Glu Arg Ala Ile Val Lys Glu Lys Met Val Ser Asn Thr
    1415                1420                1425
Lys Ser Val Asp Thr Lys Ala Ser Ser Ser Lys Phe Ser Arg Ile
    1430                1435                1440
```

Leu Thr Pro Lys Glu Tyr Leu Gln Arg Gln Lys His Lys Glu Ala
    1445                1450                1455

Leu Ser Asn Lys Ala Ser Lys Lys Ile Cys Val Lys Asn Val Pro
    1460                1465                1470

Cys Asp Ser Glu His Met Arg Pro Ser Lys Leu Ala Val Gln Val
    1475                1480                1485

Glu Ser Cys Gly Lys Ser Asn Glu Lys His Ser Ser Gly Val Gln
    1490                1495                1500

Thr Ser Lys Glu Ser Leu Asn Gly Leu Thr Ser His Gly Lys Asn
    1505                1510                1515

Leu Lys Ile His His Ser Gln Glu Ser Lys Thr Tyr Asn Ile Leu
    1520                1525                1530

Arg Asn Val Lys Glu Lys Val Gly Gly Lys Gln Pro Asp Lys Ile
    1535                1540                1545

Trp Ile Asp Lys Thr Lys Leu Asp Lys Leu Thr Asn Ile Ser Asn
    1550                1555                1560

Glu Ala Gln Phe Ser Gln Met Pro Pro Gln Val Lys Asp Gln Lys
    1565                1570                1575

Lys Leu Tyr Leu Asn Arg Val Gly Phe Lys Cys Thr Glu Arg Glu
    1580                1585                1590

Ser Ile Ser Leu Thr Lys Leu Glu Ser Ser Pro Arg Lys Leu His
    1595                1600                1605

Lys Asp Lys Arg Gln Glu Asn Lys His Lys Thr Phe Leu Pro Val
    1610                1615                1620

Lys Gly Asn Thr Glu Lys Ser Asn Met Leu Glu Phe Lys Leu Cys
    1625                1630                1635

Pro Asp Ile Leu Leu Lys Asn Thr Asn Ser Val Glu Glu Arg Lys
    1640                1645                1650

Asp Val Lys Pro His Pro Arg Lys Glu Gln Ala Pro Leu Gln Val
    1655                1660                1665

Ser Gly Ile Lys Ser Thr Lys Glu Asp Trp Leu Lys Phe Val Ala
    1670                1675                1680

Thr Lys Lys Arg Thr Gln Lys Asp Ser Gln Glu Arg Asp Asn Val
    1685                1690                1695

Asn Ser Arg Leu Ser Lys Arg Ser Phe Ser Ala Asp Gly Phe Glu
    1700                1705                1710

Met Leu Gln Asn Pro Val Lys Asp Ser Lys Glu Met Phe Gln Thr
    1715                1720                1725

Tyr Lys Gln Met Tyr Leu Glu Lys Arg Ser Arg Ser Leu Gly Ser
    1730                1735                1740

Ser Pro Val Lys
    1745

<210> SEQ ID NO 14
<211> LENGTH: 1521
<212> TYPE: PRT
<213> ORGANISM: Mus musculus

<400> SEQUENCE: 14

Met Asn Trp Asn Thr Lys Gln Glu Asn Val Pro Lys Pro Pro Tyr
1               5                   10                  15

Ser Lys Thr Gln Ser Ser Ile Leu Gln His Phe Leu Met Thr Ser Thr
                20                  25                  30

Thr Ser Gln Ser Ser Phe Asn Tyr Ser Pro His Asn Gln Glu Ala Ser

```
              35                  40                  45
Gln Thr Ser Phe Asn Tyr Ser Leu His Asn Gln Glu Ala Cys Met Tyr
 50                  55                  60

Ser Gly Asn Ser Asn Ser Val Ser Gln Pro Leu Leu Ser Gly Arg Asn
 65                  70                  75                  80

Tyr Ile Thr Pro Gln Thr Gln Ile Ser Val Ser Asn Met Pro Thr Arg
                 85                  90                  95

Thr Ile Val Ala Ser Gln Ser Ser Met Glu Arg Val Val Ser Thr Asn
            100                 105                 110

Gly Lys Gly Pro Gln Gln Pro Asn His Asn Leu Gln Thr Val Ser Ser
        115                 120                 125

Gly Ile Met Gln Asn Val Trp Leu Pro Ser His Thr Glu Ala Thr Ile
    130                 135                 140

Ser His Asn Pro Asp Gly Gly Thr Asn Met Pro Tyr Met His Pro Pro
145                 150                 155                 160

Gln Asn Gln Leu Val Thr Ser Asp Thr Tyr Ser Met Gln Leu Gln Met
                165                 170                 175

Ala Pro Leu His Ser Gly Lys Val Pro Met Thr His Gln Gly Ser Gln
            180                 185                 190

Gly Leu Asn His Phe Ile Pro Asp Gln Leu Val Asp Trp Thr Gln Tyr
        195                 200                 205

Thr Ser Asn Glu Leu Ser Tyr Pro Glu Tyr Arg Pro Pro Pro Lys Gln
    210                 215                 220

Tyr Ser Tyr Ile Leu Pro Ala Thr Thr Ser Leu Gln Val Lys Asn Asn
225                 230                 235                 240

Gln Leu Pro Thr Tyr Thr Gln Ser Leu Gln Ser Lys His Ser Val Pro
                245                 250                 255

Leu Ser Ser His Gln Tyr Ala Ala Glu Ala Ser Lys Arg Leu Ser Ala
            260                 265                 270

Leu Pro Tyr Ser Cys Arg Tyr Glu Asn Gln His Val Gln Asn Ala Gln
        275                 280                 285

Pro Val Ser Lys His Leu Pro Met Glu Val Pro Gln Ser Ser Glu Val
    290                 295                 300

His Ser Ser Glu Lys Lys Lys Asp Thr Tyr Arg Gly Phe Lys Gln Gln
305                 310                 315                 320

Trp Gln Asn Pro Asn Glu Lys Val Ser Ile Gly Gln Phe Ser Glu Val
                325                 330                 335

Lys Ile Asn Ile Lys Gln Pro Tyr Ser Glu Ser Val Arg Pro Ser Gly
            340                 345                 350

Asp Gly Val Gln Ala Leu Val Gln Asn Asn Gln Glu Lys Arg Lys Tyr
        355                 360                 365

Thr Tyr Asn Pro Asn Thr Asn Gln Val Ile Asp Thr Asn Ala Thr Lys
    370                 375                 380

Glu Lys Leu Val Arg Asp Ile Lys Ser Leu Val Glu Ile Lys Lys Lys
385                 390                 395                 400

Phe Ser Glu Leu Ala Arg Lys Ile Lys Ile Asn Lys Ser Leu Leu Met
                405                 410                 415

Ala Ala Gly Cys Ser Lys Thr Ala Asn Thr Ser Tyr Thr Glu Pro Ile
            420                 425                 430

Gln His Ser Glu Phe Ser Ala Lys Glu Met Ser Ala Lys Asn Gly Asn
        435                 440                 445

Asp Cys Ser Met Glu Leu Leu Ala Thr Cys Leu Ser Leu Trp Lys Asn
    450                 455                 460
```

```
Gln Pro Ser Lys Thr Thr Glu Glu Asn Val Pro Lys Pro Leu Glu Glu
465                 470                 475                 480

Lys Gln Cys Asn Thr Ser Arg Ile Ser Thr Thr Val Val Gly Ser Ala
                    485                 490                 495

Asn Pro Thr Asn Glu Val His Val Lys Ser Leu Cys Ser Gly Val Gly
                500                 505                 510

Asn Ser Gln Lys Met Met Ser Ser Gln Thr Val Leu Pro Val Leu
            515                 520                 525

Ile Pro Ser Cys Glu Ser Ser Gly Val Ala Val Gly Lys Gly Thr Glu
530                 535                 540

Leu Gln Ile Ala Val Val Ser Pro Leu Val Leu Ser Asp Thr Asn Thr
545                 550                 555                 560

Leu Pro Gly Lys Asp Ser Val Pro Glu Val Leu Pro Glu Thr Leu Tyr
                565                 570                 575

Pro Val Val Lys Glu Gly Ser Val Cys Ser Leu Gln Thr Gln Pro Thr
                580                 585                 590

Glu Thr Val Ala Leu Pro Phe Asp Val Ile Gly Ala Val Ala Ser Asn
        595                 600                 605

Asn Ile Ser Ala Glu Ile Pro Leu Pro Val Asp Lys Glu Lys Gln His
610                 615                 620

Lys Pro Ile Gln Gly Asp Pro Asp Ile Ala Asp Ser Ser Leu Gly Lys
625                 630                 635                 640

His Ser Pro Leu Gly Thr Glu Val Leu Pro Lys Pro Met Asp Ser Thr
                645                 650                 655

Ile Val Ser Gly Pro Met Leu Gln Ile Glu Ser Ile Cys Ser Leu Ala
                660                 665                 670

Glu Gly Asp Val Ser Tyr Asn Ser Gln Ile Ala Glu Ile Phe Asn Ser
            675                 680                 685

Val Gln Thr Glu Pro Gln Lys Pro Ser Pro Asn Gln Val Ile Asp Ser
        690                 695                 700

Gln Gln Glu Gln Val Tyr Asp Thr Thr Glu Asn Lys Asp Phe Ser Leu
705                 710                 715                 720

Gln Lys Asp Lys Cys Val Gln Cys Thr Asp Val Pro His Glu Val Pro
                725                 730                 735

Glu Gln Pro Glu Pro Leu Gln Pro Glu Glu Pro Ala Ser Ser Glu Tyr
                740                 745                 750

Val Glu Ala Asn Arg Glu Ala Thr Glu Glu Ser Cys Arg Glu Tyr Thr
            755                 760                 765

Gly Arg Lys Glu Ser Thr Ala Lys Asp Val Cys Leu Pro Ala Ala Ile
            770                 775                 780

Gln Gln Asp Pro His Pro Arg Glu Thr Asp Met Phe Ser Lys Ser Asp
785                 790                 795                 800

His Ser Leu Pro Ala Ile Asn Glu Ile Asn Asp Glu Ser Glu Pro Ile
                805                 810                 815

Ser Tyr Leu His Asp Gln Leu Ser Glu Leu Leu Lys Glu Phe Pro Tyr
                820                 825                 830

Gly Ile Glu Thr Phe Asn Arg His Glu Val Ser Leu Asp Gln Gln Lys
            835                 840                 845

Thr His Lys Ile Val Glu Asn Gln Thr Gly Gly Lys Thr Ser Asn Val
        850                 855                 860

Ser Gly Asp Ser Thr Asp Gln Ile Lys Ile Thr Val Leu Asn Ser Glu
865                 870                 875                 880
```

-continued

```
Gln Ile Lys Glu Leu Phe Pro Glu Asp Asp Gln Pro Cys Asp Lys Leu
                885                 890                 895
Ala Glu Pro Glu Asn Lys Glu Ile Val Ala Glu Val Lys Ser Pro Cys
            900                 905                 910
Asp Ser Gln Ile Pro Arg Glu Glu Ser His Asp Leu Gly Met Leu Asp
            915                 920                 925
Pro Glu Lys Asp Lys Ile His Cys Cys Ala Leu Gly Trp Leu Ser Met
        930                 935                 940
Val Tyr Glu Gly Val Pro Gln Cys His Cys Ser Ser Thr Glu Lys Lys
945                 950                 955                 960
Glu Lys Asp Gln Cys Leu Asp Ile Asn Ser Ser Lys Gln Gly Glu Gln
            965                 970                 975
Pro Cys Asn Ser Gly Ile Thr Ile Phe Glu Ile Asn Pro Val Ser Asn
            980                 985                 990
Asn Ser Lys Thr Pro Leu Thr Gln Ala Thr Glu Glu Gly His Phe Ser
            995                 1000                1005
Ala Val His Gly Glu Lys Thr Lys Ala Ser Lys Thr Lys Asp Asn
        1010                1015                1020
Arg Glu Gly Gln Glu Leu Ala Cys His Phe Ser Ala Lys Cys Tyr
        1025                1030                1035
Lys Lys Asp Lys Lys Gly Asn Phe Lys Ile Arg His Asp Thr Ser
        1040                1045                1050
Leu Lys Met Glu Gln Lys Leu Lys Asn Ile Ser Ser Lys Cys Asp
        1055                1060                1065
Ile Pro Asn Pro Ser Lys Cys Asn Lys Ile Ala Ala Pro Glu Ile
        1070                1075                1080
Leu His Val Thr Thr Ser Asn Ser Ala Lys Asn Met Pro Phe Ser
        1085                1090                1095
Lys Gln Ala Ser Gln Glu Ser Leu Gln Lys Lys His Thr Ser Gln
        1100                1105                1110
Asp Leu Gly Pro Val Lys Ala Pro Ile Glu Leu Ser Ser Asn Thr
        1115                1120                1125
Asp Pro Cys Arg Ser Asn Thr Ser Ser Val Gln Ser Val Ser Pro
        1130                1135                1140
Glu Lys Lys Lys Leu Lys Phe Lys Ala Gly Gly Ser Arg Leu Lys
        1145                1150                1155
Tyr Phe Glu Lys Arg Lys Thr Asp His Val Ile Ile Pro Asp Val
        1160                1165                1170
Glu Ile Lys Lys Lys Lys Tyr Glu Lys Gln Glu Gln Asn Lys Asn
        1175                1180                1185
Ala Gly Asp Thr Leu Lys Leu Cys Ser Ile Leu Thr Glu Ser Asn
        1190                1195                1200
Glu Arg Ala Ser Val Gln Glu Lys Thr Val Pro Ser Pro Glu Ser
        1205                1210                1215
Ser Asp Pro Lys Gly Ser Ser Ser Lys Ser Thr Arg Val Ile Thr
        1220                1225                1230
Val Gln Glu Tyr Leu Gln Arg Gln Lys Asp Lys Gln Ile Thr Gly
        1235                1240                1245
Asn Asn Ala Ser Arg Asn Ile Cys Val Glu Thr Val Leu Cys Asp
        1250                1255                1260
Ser Gly His Thr Lys Thr Ser Lys His Ser Ala Ala Val Ser Trp
        1265                1270                1275
Gly Lys Leu Val Glu Gly Gln Ser Ile Ser Ala Glu Thr Ala Lys
```

```
            1280                1285                1290

Glu Leu Glu His Asn Ser  Ser His Gly Lys Asp  Phe Lys Ile
        1295                1300            1305

His His Ser Glu Ala Ser  Arg Thr His Ser Val  Ser Asn Asn Asn
    1310                1315                1320

Lys Gly Lys Phe Asp Gly  Lys Gln Pro Asp Lys  Met Phe Lys Asn
1325                1330                1335

Lys Thr Ser Met Asn Glu  Ser Asn Gln Met Pro  Leu Gln Val
    1340                1345                1350

Lys Glu Gln Arg Lys Gln  Tyr Leu Asn Arg Val  Ala Phe Lys Cys
    1355                1360                1365

Thr Glu Arg Glu Ser Ile  Cys Leu Thr Lys Leu  Asp Ser Ala Ser
    1370                1375                1380

Lys Lys Leu Ser Ile Glu  Lys Lys Ser Gly Glu  Tyr Thr Ser Lys
1385                1390                1395

Thr Lys Asp Thr Asp Lys  Pro Ser Met Leu Glu  Phe Lys Leu Cys
    1400                1405                1410

Pro Asp Val Leu Leu Lys  Asn Thr Ser Thr Val  Asp Lys Gln Asp
    1415                1420                1425

Cys Pro Gly Pro Gly Pro  Glu Lys Glu Gln Ala  Pro Val Gln Val
    1430                1435                1440

Ser Gly Ile Lys Ser Thr  Lys Glu Asp Trp Leu  Lys Cys Ile Pro
    1445                1450                1455

Thr Arg Thr Lys Met Pro  Glu Ser Ser Gln Arg  Asp Ser Ala Asp
    1460                1465                1470

Ser Arg Leu Ser Lys Arg  Ser Leu Ser Ala Asp  Glu Phe Glu Ile
    1475                1480                1485

Leu Gln Asn Pro Val Lys  Glu Ser Asn Ile Met  Phe Arg Thr Tyr
    1490                1495                1500

Lys Lys Met Tyr Leu Glu  Lys Arg Ser Arg Ser  Leu Gly Ser Ser
    1505                1510                1515

Pro Val Lys
    1520

<210> SEQ ID NO 15
<211> LENGTH: 1741
<212> TYPE: PRT
<213> ORGANISM: Bos taurus

<400> SEQUENCE: 15

Met Asn Trp Asn Ala Lys  Pro Glu Ser Val Thr  Leu Pro Pro Gln Tyr
1               5                   10                  15

Pro Lys Lys Gln Ala Ser  Phe Leu Glu Gln Gly  Leu Val Asn Thr Leu
            20                  25                  30

Ser Thr Thr Ser Gln Ser  Ser Phe His Thr Gly  Ser Asn Gln Glu Pro
        35                  40                  45

Cys Leu Phe Leu Ser Asn  Ser His Pro Val Ser  Gln Pro Leu Leu Asn
    50                  55                  60

Ile Arg Asn His Lys Thr  Pro Pro Gln Ile Pro  Ile Ser Asp Leu His
65                  70                  75                  80

Ser Gly Thr Ile Val Thr  Ser Gln Thr Ser Val  Glu Arg Ile Thr Tyr
            85                  90                  95

Ala Asn Val Lys Gly Pro  Lys Gln Leu Ser His  Asp Leu Gln Ile Ser
            100                 105                 110
```

-continued

```
Ser Gly Val Thr Pro Asp Val Trp Leu Asn Ser Pro Met Gly Ser Ser
        115                 120                 125

Thr Leu Ser His Thr Gly Ala Thr Val Ser His Gln Thr Gly Phe Gly
130                 135                 140

Thr Asn Val Pro Asn Val His Ala Leu Gln Asn Gln Phe Leu Thr Ser
145                 150                 155                 160

Asp Thr Tyr Ser Met Gln Leu His Met Ile Pro Ser Asn Ser Gly Arg
                165                 170                 175

Val Pro Ile Thr Tyr Gln Gly Asn Thr Arg Leu Asn Leu Pro Leu Ser
            180                 185                 190

Glu Gln Gln Val Asp Trp Ala Pro Gln Arg Ala Ser Ser Gly Leu Thr
        195                 200                 205

Tyr Gln Asp Tyr Arg Pro Leu Pro Lys Gln Tyr Asn Tyr Ser Pro Arg
210                 215                 220

Ser Phe Leu Gln Glu Pro Ala Leu Gln Lys Gln Asn Ala Met Ser Ser
225                 230                 235                 240

Val Ser Phe Gln Val Lys Asn Asn Gln Ser Pro Asn Pro Ala Leu Thr
                245                 250                 255

Phe Lys Ser Lys Gln Ile Ala Ala Val Pro Ser Tyr Gln Tyr Ala Val
            260                 265                 270

Thr Gln Thr Asp Lys Arg Pro Pro Pro Tyr Asp Cys Arg Tyr Ala
        275                 280                 285

Ser Gln Ser Leu Gln Ser Thr Pro Arg Val Val Lys Gln Ser Ser Met
        290                 295                 300

Glu Val Pro Gln Ser Gln Glu Met His Leu Pro Glu Met Arg Lys Asp
305                 310                 315                 320

Phe Cys Arg Asp Phe Gln Gln Gln Trp Gln Asn Leu Asn Glu Asn Phe
                325                 330                 335

Ser Met Met Gly Gly Ser Cys Asn Leu Lys Val Asn Thr Ser Val Asn
            340                 345                 350

His Pro Phe Asn Glu Pro Val Arg Ser Ser Val Thr Gly Ala Gln Ala
        355                 360                 365

Leu Ala Gln Asn Asn Gln Glu Arg Thr Val Asp Ser Gln Asn Leu Thr
370                 375                 380

Ser Asn Gln Ala Leu Asp Thr Ser Ala Thr Lys Glu Lys Leu Val Arg
385                 390                 395                 400

Asp Ile Lys Thr Leu Val Glu Ile Lys Lys Lys Phe Ser Asp Leu Ala
                405                 410                 415

Arg Lys Ile Lys Ile Asn Lys Ser Leu Leu Met Ala Ala Gly Cys Ile
            420                 425                 430

Lys Thr Pro Asn Thr Ser Tyr Ser Glu Ser Ala Gln Asn Ser Gly Leu
        435                 440                 445

Ser Leu Lys Gln Thr Ala Lys Ile Gln Ser Glu Pro Gln Leu Thr Leu
450                 455                 460

Val Thr Pro Glu Ile Val Glu Asp Lys Pro Thr Val Met Glu Ser
465                 470                 475                 480

Ala Glu Glu Thr Asn Arg Pro Gln Arg Val Leu Ser Ser Asn Leu Gln
                485                 490                 495

Asp Arg Asn Phe Asn Gln Val Ser Val Ser Leu Asn Ser Ala Cys
            500                 505                 510

Ser Glu Lys Leu Pro Ile Pro Glu Gln Val His Asp Leu Glu Val Val
        515                 520                 525

Asn Ser Leu Lys Thr Ser Thr Val Glu Val Thr Gln Ala Pro Leu Asn
```

```
                530             535             540
Asn Thr Gln Leu Ser Ser Gly Asn Ser Val Ser Ile Ala Gln Asn Val
545                 550                 555                 560

Pro Thr Asn Ser Glu Val Thr Phe Leu Pro His Ser Thr Ser Ser Glu
                565                 570                 575

Glu Tyr Ile Ser Lys Tyr Pro Asn Lys Asn Arg Leu Ile Leu Ser Leu
                580                 585                 590

Leu Thr Ser Gly Ser Lys Thr Gln Lys Leu Leu Lys Asp Thr Gly
                595                 600                 605

Glu Cys Ile His Asp Ser Lys Leu His Asn Phe Glu Met Asn Ala Asn
            610                 615                 620

Thr Glu Asn Thr Gly Asn Gln Leu Lys Thr Thr Glu Thr Val Asn Leu
625                 630                 635                 640

Pro Arg Thr Cys Asn Arg Asn Ala Lys Val Ala Asp Thr Ser Cys Leu
                645                 650                 655

Glu Cys Lys Ser Phe Asn Gly Val Ser Ser Asn Ser Gly Ser Arg Phe
                660                 665                 670

Ser Met Glu Leu Leu Ala Thr Cys Leu Ser Leu Trp Lys Lys Gln Pro
            675                 680                 685

Ser Glu Pro Thr Lys Glu Lys Gln Asp Asn Glu Ser Lys Thr Asn Ile
            690                 695                 700

Thr Ala Ile Ala Val Ser Lys Pro Ala Pro Ile Cys Glu Ser Ser Pro
705                 710                 715                 720

Phe Ser Pro Val Gly Asn Ser Gln Asn Lys Ile Val Asn Ser Ser Leu
                725                 730                 735

Glu Thr Ile Ser Ser Val Val Ala Gln Asn Tyr Glu Ser Ser Gly Thr
                740                 745                 750

Thr Thr Thr Lys Gly Ile Ala Val Val Ser Pro Leu Ile Leu Ser Asp
            755                 760                 765

Val Asn Thr Leu Ser Val Lys Asp Thr Thr Ser Glu Ala Leu Pro Glu
            770                 775                 780

Met Val Tyr Pro Val Ile Lys Glu Gly Ser Val Cys Ser Leu Gln Asn
785                 790                 795                 800

Lys Leu Thr Glu Asn Thr Ala Ala Leu Lys Ile Asn Val Asn Glu Pro
                805                 810                 815

Val Thr Ser Thr Thr Gly Ile Met Ile Phe Pro Leu Ile Glu Asp Lys
                820                 825                 830

Gln Ser Glu Ser Thr Asn Thr Asn Ser Glu Gly Ile Pro Asn Thr Asn
            835                 840                 845

Gln Gly Lys His Asn Glu Ser Glu Pro Asp Ile Gln Cys Pro Val Ser
850                 855                 860

Asp Gln Gln Thr Ser Tyr Ile Ser Lys Asp Ser Ser Val Gly Ser
865                 870                 875                 880

Asp Val Leu Gln Ile Gly Ser Ile Cys Ser Leu Val Glu Gly Asp Thr
                885                 890                 895

Ser Tyr Asp Ser Gln Ile Ala Glu Ile Phe Asn Leu Leu Pro Leu Gln
            900                 905                 910

Lys Val Glu Pro Gln Lys Pro Leu Pro Asn His Gln Met Met Ser Ser
            915                 920                 925

Arg Gln Gln Asn Glu His Leu Glu Asn Ile Thr Glu Ser Lys Asp Phe
            930                 935                 940

Asp Phe Lys Lys Asp Glu Phe Val Gln Cys Thr Asp Val Ser Asn Lys
945                 950                 955                 960
```

-continued

```
Ile Thr Asp Gln Ser Glu Ser Leu Gln Leu Pro Ala Leu Ser Pro Leu
                965                 970                 975
Lys Cys Val Glu Ala Lys Ser Gly Ile Leu Glu Gly Ser Leu Glu
            980                 985                 990
His Ile Thr Glu Asn Glu Ser Met Ala Asn Asp Thr Cys Ser Ser Ala
        995                1000                1005
Ala Thr Gln Gln Asp Ser Tyr Pro Gln Glu Ala Asp Thr Ser Cys
       1010                1015                1020
Ser Tyr Thr Glu Gln Asp Pro Thr Thr Asp Glu Ser Leu His Asp
       1025                1030                1035
Lys Thr Ser Ile Leu Tyr Leu His Asp Gln Leu Ser Glu Leu Leu
       1040                1045                1050
Lys Glu Phe Pro Tyr Gly Ile Glu Pro Val Asn Met His Glu Ser
       1055                1060                1065
Ser Val Val Gln Gln Met Ala Asn Gln Ile Ser Glu Ala Gln Thr
       1070                1075                1080
Cys Gly Lys Thr Asp Cys Asp Ser Lys Gly Ser Thr Asp Gln Ile
       1085                1090                1095
Gln Ile Thr Ile Leu Asn Thr Asp Gln Met Lys Glu Leu Phe Pro
       1100                1105                1110
Glu Gln Asp Asp Gln Pro Ser Glu Val Asp Lys Leu Thr Glu Pro
       1115                1120                1125
Gln Lys Glu Lys Pro Val Thr Lys Glu Glu Lys Gln Cys Asp Pro
       1130                1135                1140
Gln Ala Cys Arg Val Glu Glu Arg Cys Ala Ser Val Pro Leu Asp
       1145                1150                1155
Ser Glu Lys Asp Asp Ile Arg Cys Cys Ala Leu Gly Trp Leu Ser
       1160                1165                1170
Met Val Tyr Glu Gly Val Pro Gln Cys Gln Cys Asn Ser Ile Lys
       1175                1180                1185
Lys Ser Asp Ser Lys Glu Lys Lys Gln Ile Asn Pro Cys Ser Pro
       1190                1195                1200
Ser Glu Ala Lys Ser Tyr Lys Gln Gly Glu Arg Thr Ser Asp Arg
       1205                1210                1215
Asp Val Pro Val Ala Leu Asn Ser Pro Asn Asn Pro Pro Lys
       1220                1225                1230
Ser Pro Leu Thr Ser Ser Val Glu Lys Lys His Phe Pro Glu Thr
       1235                1240                1245
Lys Gln Ser Ser Asn Ile Lys Asp Lys Ser Lys Thr Glu Arg Asn
       1250                1255                1260
Ser Ser Leu Arg Thr Glu Gln Glu Leu Ser Gly Gln Leu Leu Ser
       1265                1270                1275
Lys Gly Asp Lys Lys Leu Asp Ser Leu Gln Ser His Lys Arg Lys
       1280                1285                1290
Arg Asn Leu Gln Phe His Glu Val Asn Phe Asn Ser Ala Asn Lys
       1295                1300                1305
Ile Thr Lys Phe Ser Gln Glu Ser Leu Gln Arg Lys Phe Met Ala
       1310                1315                1320
Gln Asn Leu Gly Pro Leu Lys Pro Lys Met Ser Phe Leu Thr Ser
       1325                1330                1335
Lys Thr Lys Asp Leu Asn Met Lys Asn Gly Ser Ser Val Gln Ser
       1340                1345                1350
```

```
Val Ser Pro Glu Lys Arg Lys Leu Lys Ser Ala Gly Ser Lys Gln
1355                1360                1365

Lys Ser Leu Glu Glu Arg Lys Leu Asp Glu Gly Ile Thr Leu Asp
1370                1375                1380

Ser Glu Ile Lys Arg Lys Lys His Asp Lys Gln Glu Gln Asn Lys
1385                1390                1395

Asn Val Gly Gly Gly Ala Phe Lys Phe Cys Asn Phe Ser Thr Pro
1400                1405                1410

Asn Glu Arg Ala Trp Ile Lys Glu Lys Thr Val Ser Asn Val Lys
1415                1420                1425

Ser Ser Gly Ser Lys Asp Ser Ser Lys Met Asn Arg Val Leu
1430                1435                1440

Ser Pro Lys Glu Tyr Leu Ser Arg Gln Lys His Lys Glu Ala Leu
1445                1450                1455

Lys Lys Asn Tyr Leu Lys Asn Ser Asp Ser Gln Tyr Met Arg Pro
1460                1465                1470

Ser Lys Leu Ser Val Gln Val Glu Ser Ser Gly Lys Ser Asn Glu
1475                1480                1485

Arg Pro Asn Gly Ser Val Gln Thr Cys Lys Glu Ser Leu Asn Ile
1490                1495                1500

Gly Thr Gly His Gly Lys Ser Ile Lys Thr His His Ser Lys Glu
1505                1510                1515

Ser Lys Thr Tyr Ile Ser Arg Asn Ile Lys Gly Thr Val Gly Gly
1520                1525                1530

Lys Gln Ser Asp Lys Met Trp Ile Asp Arg Thr Lys Leu Asp Lys
1535                1540                1545

Asn Leu Asn Asn Ile Asn Asn Glu Gly Glu Leu Ser Gln Met Ser
1550                1555                1560

Ser Gln Thr Lys Asp Gln Arg Lys Leu Tyr Leu Asn Arg Val Ala
1565                1570                1575

Phe Lys Cys Thr Glu Arg Arg Ile Cys Leu Thr Lys Leu Asp
1580                1585                1590

Asn Ser Pro Arg Lys Leu Lys Glu Lys Arg Pro Glu Ser Lys Cys
1595                1600                1605

Lys Asn Pro Leu Pro Val Lys Asp Thr Thr Glu Lys Leu Ser Met
1610                1615                1620

Leu Glu Phe Lys Leu Cys Pro Asp Gly Val Phe Lys Asn Thr Asn
1625                1630                1635

Thr Val Glu Asp Gln Lys Asp Leu Gln His Thr Pro Arg Lys Glu
1640                1645                1650

Gln Ala Pro Val Gln Val Ser Gly Ile Lys Ser Thr Lys Glu Asp
1655                1660                1665

Trp Leu Lys Cys Val Thr Glu Glu Lys Arg Met Pro Glu Ala Asn
1670                1675                1680

Gln Glu Ile Asp Asp Asn Val Leu Ala Asn Ser Arg Leu Ser Lys
1685                1690                1695

Arg Asn Cys Ser Ala Asp Gly Phe Glu Ile Leu Gln Asn Pro Val
1700                1705                1710

Lys Asp Ser Lys Ala Met Phe Gln Thr Tyr Lys Lys Leu Tyr Met
1715                1720                1725

Glu Lys Arg Ser Arg Ser Leu Gly Ser Ser Pro Leu Glu
1730                1735                1740
```

```
<210> SEQ ID NO 16
<211> LENGTH: 1746
<212> TYPE: PRT
<213> ORGANISM: Sus scrofa

<400> SEQUENCE: 16

Met Asn Trp Asn Ala Lys Pro Glu Ser Val Thr Leu Pro Pro Gln Tyr
1               5                   10                  15

Pro Arg Lys Gln Thr Ser Phe Leu Glu Gln Ala Leu Val Ser Thr Leu
            20                  25                  30

Thr Thr Ser Gln Ser Pro Leu Asn His Pro Gly Ser Asn Gln Glu Ala
        35                  40                  45

Cys Leu Phe Leu Ser Asn Ser Asn Pro Val Ser Gln Pro Leu Leu Asn
    50                  55                  60

Asn Arg Asn Tyr Lys Thr Pro Gln Gln Ile Pro Ile Ser Asp Met His
65                  70                  75                  80

Ser Gly Thr Ile Val Thr Ser Gln Thr Ser Val Glu Arg Ile Thr Tyr
                85                  90                  95

Thr Asn Val Lys Gly Pro Lys Gln Leu Asn Gln Asp Leu Gln Val Ser
            100                 105                 110

Ser Gly Val Thr Gln Asp Met Trp Leu Asn Ser Pro Met Arg Asn Ser
        115                 120                 125

Met Leu Ser His Thr Gly Ala Thr Val Ser His Gln Thr Gly Phe Gly
    130                 135                 140

Thr Asn Pro Pro Asn Val His Ala Leu Gln Asn Gln Phe Val Thr Ser
145                 150                 155                 160

Asp Thr Tyr Ser Met Gln Leu Gln Met Met Pro Ser Asn Ser Gly Arg
                165                 170                 175

Ala Pro Ile Thr Tyr Gln Asp Asn Pro Arg Leu Asn Pro Pro Leu Ser
            180                 185                 190

Glu Gln Gln Val Asp Trp Pro Gln Gln Cys Ala Ser Ser Gly Leu Ala
        195                 200                 205

Tyr Pro Asn Tyr Arg Pro Leu Pro Lys Gln Tyr Gly Tyr Ser Ser Arg
    210                 215                 220

Ser Phe Val Gln Gly Pro Thr Leu Pro Lys Gln Asn Thr Met Ser Ala
225                 230                 235                 240

Gly Ser Leu Gln Val Lys Asn Ser Pro Ser Asn Pro Val Leu Pro
                245                 250                 255

Leu Gln Ser Lys Gln Ile Ala Thr Ile Pro Ser Tyr Gln Tyr Ala Val
            260                 265                 270

Thr His Thr Asp Glu Arg Pro Pro Pro Tyr Asp Cys Arg Tyr Ala
        275                 280                 285

Ser Gln Pro Leu Gln Ser Ile Gln His Val Val Lys Arg Ser Ser Met
    290                 295                 300

Asp Gly Pro Gln Thr Gln Glu Met Tyr Leu Pro Glu Met Gly Lys Asp
305                 310                 315                 320

Phe Cys Arg Gly Phe Gln Gln Trp Gln Asn Ser Asn Glu Asn Phe
                325                 330                 335

Ser Met Met Gly Asn Thr Cys Asn Leu Lys Val Asn Thr Asn Val Gly
            340                 345                 350

Gln Pro Phe Asn Arg Pro Val Arg Ser Ser Leu Asp Ser Val Gln Ala
        355                 360                 365

Leu Gly Gln Asn Thr Gln Glu Lys Arg Val Asp Ser Gly Asn Leu Thr
    370                 375                 380
```

```
Ser Asn Gln Val Leu Asp Thr Arg Ala Lys Lys Lys Leu Val Arg
385                 390                 395                 400

Asp Ile Lys Thr Leu Val Glu Ile Lys Lys Phe Ser Asp Leu Ala
        405                 410                 415

Arg Lys Ile Lys Ile Asn Lys Ser Leu Leu Met Ala Ala Gly Cys Ile
            420                 425                 430

Lys Thr Thr Ser Ser Pro Tyr Ser Asn Thr Ala Gln Asn Ser Gln Phe
        435                 440                 445

Ser Leu Lys Gln Thr Ala Lys Val Gln Cys Gly Pro Gln Val Thr Ile
    450                 455                 460

Val Thr Pro Glu Thr Met Glu Asn Lys Ser Pro Ile Val Met Glu Ser
465                 470                 475                 480

Ser Glu Val Ala Asn Lys Thr His Ser Pro Ser Asn Ser Asn Leu Gln
                485                 490                 495

Asp Arg His Phe Asn Gln Val Ser Ser Val Leu Leu Asn Ser Val Pro
            500                 505                 510

Ser Glu Lys Leu Pro Ile Pro Glu Gln Leu Arg Asp Leu Lys Val Val
    515                 520                 525

Thr Ser Ser Lys Met Ser Thr Val Glu Ile Pro His Ala Thr Ser Asn
530                 535                 540

Asn Ile Gln Phe Ser Ser Gly Asn Leu Val Asn Ser Thr Lys Asn Val
545                 550                 555                 560

Pro Ala His Ser Glu Thr Thr Pro Leu Pro Gln Phe Met Thr Phe Glu
                565                 570                 575

Glu Tyr Ile Ser Lys His Pro Asn Lys Asn Arg Leu Val Leu Ser Leu
            580                 585                 590

Leu Ala Pro Gly Gly Lys Ile Glu Arg Lys Leu Leu Lys Asp Thr Ile
    595                 600                 605

Glu Thr Val Lys Asp Ser Lys Met Arg Ser Ser Asp Val Asn Pro Asn
610                 615                 620

Thr Thr Asn Thr Gly Asn Leu Met Asn Leu Lys Thr Val Glu Thr Ala
625                 630                 635                 640

Ser Ala Cys Asn Ile Asn Ala Lys Ile Ser Asp Asn Ser Ser Gly Phe
            645                 650                 655

Glu His Lys Ser Leu Asn Gly Met Ser Ser Lys Ser Asp Ser His Phe
            660                 665                 670

Ser Met Glu Leu Leu Ala Thr Cys Leu Ser Leu Trp Lys Lys Gln Pro
    675                 680                 685

Ser Glu Pro Thr Val Glu Lys Gln Ser Asn Glu Ser Lys Thr Asn Arg
    690                 695                 700

Ala Ala Ala Gly Val Ser Lys Pro Val Glu Val Cys Glu Thr Ser Pro
705                 710                 715                 720

Phe Ser Ala Val Gly Asn Ser Gln Asn Lys Val Thr Ser Ser Ser Gln
                725                 730                 735

Glu Thr Val Leu Ser Met Val Thr Gln Asn Phe Glu Ser Ser Gly Ser
            740                 745                 750

Thr Thr Thr Lys Gly Ile Ala Val Val Ser Pro Leu Ile Leu Ser Asp
        755                 760                 765

Val Lys Thr Leu Ser Val Lys Gly Ile Thr Pro Glu Ala Leu Pro Glu
    770                 775                 780

Thr Ala Tyr Pro Val Ile Lys Glu Gly Ser Ile Cys Ser Leu Gln Asn
785                 790                 795                 800

Lys Leu Glu Asn Thr Ala Ala Leu Lys Val Ser Val His Glu Pro Val
```

```
              805                 810                 815
Thr Ser Thr Thr Ser Thr Lys Ile Phe Pro Leu Ile Gln Lys Glu Lys
              820                 825                 830
Gln Asn Glu Ser Thr Asn Ala Asn Ser Glu Gly Thr Pro Asn Thr Ser
              835                 840                 845
Gln Gly Lys Tyr Asn Glu Thr Glu Pro Asp Val Gln Cys Pro Val Ser
              850                 855                 860
Asp Gln Gln Thr Ser Tyr Val Ser Lys Asp Ser Asp Val His Ser
865               870                 875                 880
Asp Val Leu Gln Ile Asp Asn Ile Cys Ser Leu Val Glu Gly Asp Thr
              885                 890                 895
Ser Tyr Asn Ser Gln Ile Ala Lys Ile Phe Asn Leu His Pro Leu Glu
              900                 905                 910
Lys Val Glu Gln Gln Lys Pro Leu Leu Ser His Gln Val Met Ser Ser
              915                 920                 925
Arg Gln Gln Asn Glu Gln Val Asp Val Thr Glu Ser Lys Asp Phe Asp
              930                 935                 940
Cys Gln Lys Asp Asn Phe Val Gln Cys Thr Asp Thr Ser His Glu Thr
945               950                 955                 960
Ile Asp Gln Ser Met Leu Leu His Pro Pro Glu Ser Ser Ser Leu Lys
              965                 970                 975
Tyr Thr Glu Ala Lys Arg Gly Ile Pro Glu Glu Ser Ser Leu Glu Gln
              980                 985                 990
Ile Thr Glu Ile Glu Ser Leu Ala Asp Asp Val Val Ser Pro Ala Ala
              995                 1000                1005
Ile Gln Gln Asp Asn Cys Pro Gln Glu Thr Asp Met Ser Cys Ser
              1010                1015                1020
Tyr Thr Ala Gln Asp Pro Thr Lys Asn Glu Leu Leu Asp Asp Glu
              1025                1030                1035
Thr Ser Ile Leu Tyr Leu Gln Asp Gln Leu Ser Glu Leu Leu Lys
              1040                1045                1050
Glu Phe Pro Tyr Gly Ile Glu Pro Val Asn Met His Glu Gly Cys
              1055                1060                1065
Ala Val Gln Gln Met Ala Asp Pro Ile Ser Lys Pro Gln Thr Cys
              1070                1075                1080
Glu His Thr Gly Cys Asp Ser Lys Asp Ser Thr Asp Gln Ile Gln
              1085                1090                1095
Ile Thr Ile Leu Asn Ser Glu Gln Met Lys Glu Leu Phe Pro Glu
              1100                1105                1110
Gln Asp Gly Pro Pro Asn Glu Val Asp Arg Leu Thr Glu Leu Gln
              1115                1120                1125
Glu Glu Lys Pro Val Thr Lys Glu Gly Asn Gln Cys Asp Pro Gln
              1130                1135                1140
Ala Arg Thr Ile Glu Glu Ser Cys Glu Ser Val Val Leu Asp Ser
              1145                1150                1155
Glu Lys Asp Asp Val Arg Cys Cys Ala Leu Gly Trp Leu Ser Met
              1160                1165                1170
Val Tyr Glu Gly Val Pro Gln Cys Gln Cys Asn Ser Ile Lys Asn
              1175                1180                1185
Ser Ala Ser Lys Glu Glu Lys Gly Lys Asp Pro Cys Ser Leu Glu
              1190                1195                1200
Ala Asn Ala Asn Ser Tyr Lys Arg Gly Glu Arg Thr Ser Asp Gly
              1205                1210                1215
```

-continued

Asp Asp Ser Val Thr Phe Glu Asn Pro Pro Asp Asn Gln Lys Leu
1220                 1225                 1230

Pro Leu Thr Phe Pro Val Glu Glu Lys His Phe Pro Glu Thr Glu
1235                 1240                 1245

Gly Gly Arg Asn Ile Asn Asp Lys Ser Glu Thr Glu Gln Asn Ser
1250                 1255                 1260

Ser Leu Arg Thr Glu Gln Glu Leu Pro Gly Gln Phe Leu Cys Lys
1265                 1270                 1275

Gly Gly Lys Arg Arg Asp Pro Leu Gln Arg His Lys Lys Lys Pro
1280                 1285                 1290

Leu Gln Phe His Glu Val Thr Phe Gln Ser Thr Asn Lys Thr Ile
1295                 1300                 1305

Lys Ile Cys Gln Glu Ser Leu Gln Arg Lys Leu Met Ala Gln Asn
1310                 1315                 1320

Leu Arg Pro Leu Lys Pro Lys Met Gly Phe Leu Thr Ser Lys Asn
1325                 1330                 1335

Lys Asp Leu His Val Lys Asn Ala Ser Leu Val Gln Ser Ile Thr
1340                 1345                 1350

Pro Glu Lys Arg Lys Leu Lys Ala Ala Gly Ser Lys His Lys Val
1355                 1360                 1365

Leu Glu Lys Arg Lys Leu Asp Asp Gly Ser Ile His Asp Ser Glu
1370                 1375                 1380

Val Lys Lys Lys Lys Tyr Asp Lys Gln Glu Gln Asn Lys Asn Val
1385                 1390                 1395

Gly Ser Gly Thr Phe Lys Leu Tyr Asn Phe Ser Thr Pro Ser Glu
1400                 1405                 1410

Arg Ala Met Thr Lys Glu Lys Thr Val Ser Asn Val Lys Ser Ser
1415                 1420                 1425

Gly Ser Lys Asp Gly Ser Ser Lys Ile Asn Arg Val Leu Thr Ala
1430                 1435                 1440

Lys Glu Tyr Leu Ala Arg Gln Lys His Lys Glu Ala Val Ser Gly
1445                 1450                 1455

Lys Thr Leu Lys Lys Asn Cys Leu Lys Asn Leu Pro Cys Asp Ser
1460                 1465                 1470

Gln Tyr Lys Lys Ser Ser Lys Leu Pro Val Arg Val Gly Ser Cys
1475                 1480                 1485

Gly Lys Ser Ser Glu Arg Gln Asn Ser Asn Val Gln Thr Thr Lys
1490                 1495                 1500

Glu Ser Leu Pro Ile Ser Ser Asn His Gly Lys Ser Leu Lys Ile
1505                 1510                 1515

His His Ser Arg Asp Ser Lys Thr His Ile Leu Arg Asn Ile Lys
1520                 1525                 1530

Gly Thr Val Gly Gly Lys Gln Pro Asp Lys Met Trp Ile Asp Lys
1535                 1540                 1545

Thr Lys Ser Asp Lys Asn Val Asn Asn Val Asn Asn Glu Ala Glu
1550                 1555                 1560

Phe Ser Gln Met Ser Ser Gln Ala Lys Asp Gln Arg Lys Thr Tyr
1565                 1570                 1575

Leu Asn Arg Val Gly Phe Lys Cys Thr Glu Arg Glu Arg Ile Cys
1580                 1585                 1590

Leu Thr Lys Leu Asp Gly Ser Pro Arg Lys Leu Asn Lys Glu Lys
1595                 1600                 1605

```
Arg Pro Glu Asn Lys Pro Lys Asn His Val Pro Gly Lys Asp Thr
    1610                1615                1620

Ser Glu Lys Leu Ser Met Leu Glu Phe Lys Leu Cys Pro Asp Gly
    1625                1630                1635

Leu Phe Lys Asn Pro Asn Pro Val Glu Asp Gln Lys Asp Leu Gln
    1640                1645                1650

Pro Cys Pro Met Lys Glu Gln Ala Pro Val Gln Val Ser Gly Ile
    1655                1660                1665

Lys Ser Thr Lys Glu Asp Trp Leu Lys Cys Val Thr Glu Glu Lys
    1670                1675                1680

Lys Ile Pro Glu Pro Asn Gln Glu Ile Asp Asp Val Leu Ala Asn
    1685                1690                1695

Ser Arg Leu Ser Lys Arg Ser Phe Ser Ala Asp Gly Tyr Glu Thr
    1700                1705                1710

Gln Gln Asn Gln Val Lys Asp Ser Lys Ala Met Phe Gln Thr Tyr
    1715                1720                1725

Lys Lys Met Tyr Met Glu Lys Arg Ser Arg Ser Leu Gly Ser Ser
    1730                1735                1740

Pro Leu Glu
    1745

<210> SEQ ID NO 17
<211> LENGTH: 4644
<212> TYPE: DNA
<213> ORGANISM: Cricetulus griseus

<400> SEQUENCE: 17
atgaattgga atgcaaaacc agagaatgct gccccaaacc caccatattc taaaagccag      60
tcgtctcttt tgcagcagtt tttaatgcct tccacaactt ctcaaagttc tttcagctgt     120
ctcccacata accaagaagc atgcatatat cccactaatt caaattcagt tcacagcca      180 cttctgaacg tcaggagttt cataaatcct ccgatctctg tttctaatgt gcataatagg     240
acagttgtgg cctcacagac ctcagtagaa agagtcacat atacaaatgt taaaggagcc     300
caacaaccaa accacaattt gcaaacagtg tcttctggag ttgtgcaaaa tgcctggatg     360
aattcaacaa tgaggaattt tatgccttct cttacagagg caaccatatc tcataaacct     420
gatggtgggc ctagtatgcc atatatgcat gcaccacaga gtcatcttgt cacatcagac     480
acctactctg tgcaactaca gatgactcct tcaaactctg taagaggccc tgtaacttac     540
caaggaaatt atcaaggaaa tccgggactt aaccactcga tggcaggtga gcttggctgg     600
gtacaatgtg catccagtga acttacttat ccagattaca gaccacctcc aaagcaatat     660
ccttatttac cacaaagctt tgtgcaagac acttctgttc agaaacaaaa ctttgtgtca     720
tctacatcat tacaagttaa aaataatcag cttccaccct ctacacagac cttaccatca     780
aagcgccctg tacctgtgtc gtcatatcag tatgctgcag aaaccagcaa aagactccct     840 ccccccccctt acagctgtag atatggaagc caacatgtgc aaaattctca gtctgtttct     900
agacacttgc ctgtggaagt tcctcagagt tcagaaatgc actcgtctga aaaaagaaa      960 gatgcttaca agtctttca acagcagtgg cagagcacta gtaaaaatgt cagtacaata    1020
ggaaaattct gtgagttgaa aattaataca aaacagtctt acaatgactc tgctggctct    1080
tctggggatg gtgttcatac tcttgttcaa aataatcaag aagaaagaaa gtattcttat    1140
aatccaagta caaatcaaat actagacaca atgtcacaa agaaaagct ggtgagggat      1200 attaaatcac tagtagaaat taaaagaaa ttttcagaac ttgcaagaaa aattaaaatc    1260
```

```
aacaaaaagc ttttgatggc agctggttgc agtaaaacag ctaatacttc ttatactgaa    1320
ccaactcggc attctgaatt ttcagcaaaa gaaatgtctg ctaaaaggga caatcagtgc    1380
tccatggaat tgctagcaac atgcctttct ctttggaaaa accaacctcc aaaaaccaca    1440
gaagaaaatg tttcaaaacc tttagaagaa aaacaatata atgcatcaag aactagtaca    1500
acagcggttg gcccttcaaa tcccatgaat gaagttcatg tgaagaattt ttgttcaggt    1560
gttagaaatt ctcagaaaat aaccacctcg tcacaaacag tcttgtcagt tctcacacca    1620
gtttacgatt cttcagatgt agctgttgga aaaggaacag agcttcagat tgctgtggtt    1680
tcacctttaa ttctttcaga tgtcagtact gtacctggga aagagttagc tcctgaagtc    1740
gtatctgaaa ctgtatatcc agttgtgaag gaaggcagtg tttgtagctt acaaaaccag    1800
caggcagaaa atgcaacagt aactgctggt ttgccctttg atgttatcag agcagtagca    1860
agtgctactg tatcagctga gctatcactg cctgggcata agaaaagca gcacaaacca     1920 acacagagtg atctagacat cgctgatggc agcctaggga acactctcc ccagggtgct     1980 gaagctttgc ctaaccctag ggacagcacc attgtgagtg ggcctatatt acagattgaa    2040
agtatctgtt ctcttgcaga aggtgatgta tcttacaatt cccaaatagc agagatattc    2100
aactctgtac aaaatgagcc ccagaaacct tcacctgatc agcaagtaat taatagtcaa    2160
caagaagaac aagtagataa ggttgctgaa aataaagact taagttttct gaaagacaag    2220
tgtatgcagt gtacagatgt tcctcatgaa gtcactgaac agccagagcc actgcagcct    2280
ttagagacaa catctgatga gtatgttgaa gcaaacggag aaatcctaga ggaaagcagt    2340
aaggagaatc ctggtgaaaa agagatgact aaggacatat tgtgttcacc agctgctgtt    2400
cagcaagatc ctcaacctca ggaaattgac acagccagca gtaagtcagg acacagtttt    2460
tctacagtaa atgagattaa tgatgaaaat gaacctgtct cataccacta tgaccagctg    2520
ttagaacttc taaaagagtt tccttatggc attgaaacta ttgccaggcc tgaagtttat    2580
gtgggccaac aaaagacaca tgaaatctta gaaaatcaaa ctggtagtaa aactggtaat    2640
gtgtctgggg ataacacaga ccaaataaaa attacagtat taaactcaga acaaatcaaa    2700
gaattatttc ctgaagagga tcagccatgt gatgtagaca aattggcaga acccgagaat    2760
acaaaaatca ttgcagaagt aaagagcctg tgtgattcac aggtccccag agaagaaagt    2820
cacaaccctg gaatgttgga tctggagaaa gataaaatcc attgctgtgc cttgggctgg    2880
ctctcaatgg tttatgaagg tgtgccacag tgtcagtgca gttccatgga agagaaagag    2940
aaagaccagt gttctttgga aatctctaat tgcaaacaag gagagcaggc ctgcaatagt    3000
ggaatcacta tttttgaaat taatcctatt tctaataact caaaaagtcc tctgatccaa    3060
gaatctgaga aaggccattt ttctgacata catggtgaaa agataaaaac atctgaaaca    3120
aaaaacagca gctcaccaag ggtagaacag gaattaactg gtcattttc aatgaaatgt    3180 taccagaaag ataaatctac aacaaaacag gatagctcac tgaaaacaga gcaaaaaata    3240
aaaaatcttt cttctaaatg tgacaaacca aatcccttaa aaagcagtaa aataccaacc    3300
cctgaaacat ttaatgtggt aacttccaac tctgataaaa atatgccagc attttctaaa    3360
caagattctc agggaagcct gcagaagaaa cacctattcc aagactcaga tccagtaaaa    3420
ggacatgtat ggctttttgcc aaataaagat ccacgcagga gaatacctt tttagtacag    3480 tcagtatcac cagaaaagaa aaagtttaaa ttcaaatcgg gtagctccaa actgaaatat    3540
tttgaaaaaa gaaaaatgga ccatttgctt atctcagatg tggaaataaa aaagaagaaa    3600
```

```
tacgaaaaac aagagcagaa caaaaatgct ggaggcacac tcaaattatg tagtactctg    3660
actgaaccaa atgaaagagc ctgtgctaaa gaaaagatag tgacaaattc tgagccctca    3720
gactcaaagg gaagctcctc taagagtact agagttataa ctgtgcagga atatttacag    3780
cggaaaaaag acaaacatgt aataggaaat aatgcctcca aaaacatctg tgtagaaaat    3840
gtgccatgtg actctgaacc catgaagtcc agtaaacatt ctgcatcacc tagtttggga    3900
aaattaattg agggccaggg tgtcagtgca gagactttaa aagaagtaga acataattcc    3960
accagccatg gcaaaaatct caagacccac cgttctgagg agactaggcc atacagtgtg    4020
tcaaatagta aagagaaatt ttataggaca catccagaca aatcttacat tgataaagct    4080
aaattagaaa gattgaccag tatgagtagt aagtccagcc agctccaggt aaaggaaaaa    4140
aggaaacagt acctgaatcg agttgcattc aaatgcacag aacaggaaag catttgtctc    4200
accaaattgg acagtgcatc caagaagctt agtaaagaga agaaaagag tacagcatgt    4260 gcacccatga caaagactg cacacacaag cccatgttgg agtttaaatt atgtccagat    4320
gtgctattga agaatacaag ctccattgac aaagggatg atccaaggcc tgggcctgag    4380
aaggagcgag cacctgtgca gtttcagga ataaaaacta caaagaaga ctggttaaaa    4440 tgtatcccaa caaggacaaa gatgcccgaa tcaagtgaac aaacagatcg ggctgactca    4500
agactctcta agagaagctt cagtgcagat gaatttgaaa ctctacaaaa cccagtaaaa    4560
gactcaaatg tcatgttccg gactttcaaa agatgtacc tggagaagag aagcaggagc    4620
ctggggagca gtccagtgaa gtag                                          4644
```

<210> SEQ ID NO 18
<211> LENGTH: 112
<212> TYPE: DNA
<213> ORGANISM: Cricetulus griseus

<400> SEQUENCE: 18

```
tgctgggatt taaggggaaa gctttaataa aagatcttta tttgtatttc ttgcagattt     60
gtgacattca aaaccacaga ctatgcaaca ctactactaa accaggtcaa at           112
```

<210> SEQ ID NO 19
<211> LENGTH: 36
<212> TYPE: DNA
<213> ORGANISM: Cricetulus griseus

<400> SEQUENCE: 19

```
cttcgggata gagtggtttt gcttttacca ccagga                              36
```

<210> SEQ ID NO 20
<211> LENGTH: 205
<212> TYPE: PRT
<213> ORGANISM: Homo sapiens

<400> SEQUENCE: 20

```
Ile Ala Trp Ala Arg Thr Glu Leu Leu Asn Val Cys Met Asn Ala Lys
1               5                   10                  15

His His Lys Glu Lys Pro Gly Pro Glu Asp Lys Leu His Glu Gln Cys
            20                  25                  30

Arg Pro Trp Arg Lys Asn Ala Cys Cys Ser Thr Asn Thr Ser Gln Glu
        35                  40                  45

Ala His Lys Asp Val Ser Tyr Leu Tyr Arg Phe Asn Trp Asn His Cys
    50                  55                  60

Gly Glu Met Ala Pro Ala Cys Lys Arg His Phe Ile Gln Asp Thr Cys
```

```
                65                  70                  75                  80
Leu Tyr Glu Cys Ser Pro Asn Leu Gly Pro Trp Ile Gln Gln Val Asp
                    85                  90                  95

Gln Ser Trp Arg Lys Glu Arg Val Leu Asn Val Pro Leu Cys Lys Glu
                100                 105                 110

Asp Cys Glu Gln Trp Trp Glu Asp Cys Arg Thr Ser Tyr Thr Cys Lys
                115                 120                 125

Ser Asn Trp His Lys Gly Trp Asn Trp Thr Ser Gly Phe Asn Lys Cys
                130                 135                 140

Ala Val Gly Ala Ala Cys Gln Pro Phe His Phe Tyr Phe Pro Thr Pro
145                 150                 155                 160

Thr Val Leu Cys Asn Glu Ile Trp Thr His Ser Tyr Lys Val Ser Asn
                    165                 170                 175

Tyr Ser Arg Gly Ser Gly Arg Cys Ile Gln Met Trp Phe Asp Pro Ala
                180                 185                 190

Gln Gly Asn Pro Asn Glu Glu Val Ala Arg Phe Tyr Ala
                195                 200                 205

<210> SEQ ID NO 21
<211> LENGTH: 27
<212> TYPE: PRT
<213> ORGANISM: Homo sapiens

<400> SEQUENCE: 21

Ala Ala Met Ser Gly Ala Gly Pro Trp Ala Trp Pro Phe Leu Leu
1               5                   10                  15

Ser Leu Ala Leu Met Leu Leu Trp Leu Leu Ser
                20                  25

<210> SEQ ID NO 22
<211> LENGTH: 257
<212> TYPE: PRT
<213> ORGANISM: Homo sapiens

<400> SEQUENCE: 22

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
                35                  40                  45

Pro Glu Asp Lys Leu His Glu Gln Cys Arg Pro Trp Arg Lys Asn Ala
                50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                    85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
                115                 120                 125

Val Leu Asn Val Pro Leu Cys Lys Glu Asp Cys Glu Gln Trp Trp Glu
                130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
```

```
              165                 170                 175
Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 23
<211> LENGTH: 128
<212> TYPE: DNA
<213> ORGANISM: Cricetulus griseus

<400> SEQUENCE: 23
atgtttggtt ttcacaagcc aaagatgtac cgaagtatag agggctgctg tatctgcaga      60
gccaagtcct ccagctctcg gttcacggac agtaaacgtt atgaaaagga cttccagagc     120
tgttttgg                                                              128

<210> SEQ ID NO 24
<211> LENGTH: 25
<212> TYPE: DNA
<213> ORGANISM: Cricetulus griseus

<400> SEQUENCE: 24
tgtaccgaag tatagagggc tgctg                                            25

<210> SEQ ID NO 25
<211> LENGTH: 25
<212> TYPE: DNA
<213> ORGANISM: Cricetulus griseus

<400> SEQUENCE: 25
tgtccgtgaa ccgagagctg gagga                                            25

<210> SEQ ID NO 26
<211> LENGTH: 20
<212> TYPE: DNA
<213> ORGANISM: Artificial Sequence
<220> FEATURE:
<223> OTHER INFORMATION: Primer 1

<400> SEQUENCE: 26
gtcccagcac tcatgaggat                                                  20

<210> SEQ ID NO 27
<211> LENGTH: 20
<212> TYPE: DNA
<213> ORGANISM: Artificial Sequence
<220> FEATURE:
<223> OTHER INFORMATION: Primer 2

<400> SEQUENCE: 27
cctcctagct ccaggtattt                                                  20

<210> SEQ ID NO 28
```

```
<211> LENGTH: 20
<212> TYPE: DNA
<213> ORGANISM: Artificial Sequence
<220> FEATURE:
<223> OTHER INFORMATION: Primer 3

<400> SEQUENCE: 28
gaggacttgg ctctgcagat                                              20

<210> SEQ ID NO 29
<211> LENGTH: 20
<212> TYPE: DNA
<213> ORGANISM: Artificial Sequence
<220> FEATURE:
<223> OTHER INFORMATION: Primer 4

<400> SEQUENCE: 29
ttccacagag cacagccgat                                              20

<210> SEQ ID NO 30
<211> LENGTH: 1080
<212> TYPE: DNA
<213> ORGANISM: Cricetulus griseus

<400> SEQUENCE: 30
ccttagtatt gggattttga ccagggtagt taatttcagt catcatttct aaactctaag    60
gttgtcatat ctgtgatttt cataccttcc taaaggtgac tgtatagaac ttcagttatc   120
aaagaacaca ccccccactt ccacagagca cagccgatat gtggagcctc ttgtgtcctg   180
ggaacagagt ggtcatagtg aatgcacact actttcccag cagggagttt aaagttttag   240
gtacattctt aatggcatgt gtgtatgggg gtgggcacag tagtaaagaa agtgccaaca   300
tgactgactg ctccatgatg tggttaaggt ttttattaga tgaacagcag ccagcaaact   360
gggcatggcc agggttctgt ctcttgagta ttgtggtata gttagttcct atgttgtgtg   420
atataagaaa caaaggaggt agtggatgcc tcctagctcc aggtattttc gaatgttttg   480
tatactggcc ctatggagta gtagatctgg ggaattcttg tagtttgttt gacttggcta   540
taaaattgta tgtgctggag gtagggtgga acagagaaaa gtccttgcat cgtttcttgt   600
catttccctt aacaaagctg tgccaattcc tttgtcttta caggtattgc tcagaagaaa   660
agatgtttgg ttttcacaag ccaaagatgt accgaagtat agagggctgc tgtatctgca   720
gagccaagtc ctccagctct cggttcacgg acagtaaacg ttatgaaaag gacttccaga   780
gctgttttgg gtaagattag ttatggtccc tcccccaccc cattacccct cactctccac   840
cgaggcaggg tttctctgta gcttaagagc ttgtcctgga actggctctg tagaccaggt   900
tagcctcaaa ctcacagaga tcctcatgag tgctgggact aaaggcatgc accaccacca   960
tccacctgta ttccattctt agagggaaaa ataatcagga ttgtgtggaa atgtttccat  1020
gcaaagcaat gggaacaatg tgctaatatt taaaatcact agttttctat tatttgggtt  1080

<210> SEQ ID NO 31
<211> LENGTH: 114
<212> TYPE: DNA
<213> ORGANISM: Cricetulus griseus

<400> SEQUENCE: 31
atgtttggtt ttcacaagcc aaagatgtac cgaagtatag agggctgctg tatcctccag    60
ctctcggttc acggacagta aacgttatga aaaggacttc cagagctgtt ttgg         114
```

-continued

```
<210> SEQ ID NO 32
<211> LENGTH: 123
<212> TYPE: DNA
<213> ORGANISM: Cricetulus griseus

<400> SEQUENCE: 32
atgtttggtt ttcacaagcc aaagatgtac cgaagtatag agggctgctg tatctgccaa      60
gtcctccagc tctcggttca cggacagtaa acgttatgaa aaggacttcc agagctgttt    120
tgg                                                                   123

<210> SEQ ID NO 33
<211> LENGTH: 21
<212> TYPE: DNA
<213> ORGANISM: Artificial
<220> FEATURE:
<223> OTHER INFORMATION: siRNA - METTL20_1 sense

<400> SEQUENCE: 33
cccugauguu guuagaggat t                                                21

<210> SEQ ID NO 34
<211> LENGTH: 21
<212> TYPE: DNA
<213> ORGANISM: Artificial
<220> FEATURE:
<223> OTHER INFORMATION: siRNA - METTL20_1 antisense

<400> SEQUENCE: 34
uccucuaaca acaucagggt t                                                21

<210> SEQ ID NO 35
<211> LENGTH: 21
<212> TYPE: DNA
<213> ORGANISM: Artificial
<220> FEATURE:
<223> OTHER INFORMATION: siRNA - C12orf35_1 sense

<400> SEQUENCE: 35
cauccagaca aaucuuacat t                                                21

<210> SEQ ID NO 36
<211> LENGTH: 21
<212> TYPE: DNA
<213> ORGANISM: Artificial
<220> FEATURE:
<223> OTHER INFORMATION: siRNA - C12orf35_1 antisense

<400> SEQUENCE: 36
uguaagauuu gucuggaugt g                                                21

<210> SEQ ID NO 37
<211> LENGTH: 21
<212> TYPE: DNA
<213> ORGANISM: Artificial
<220> FEATURE:
<223> OTHER INFORMATION: siRNA - C12orf35_2 sense

<400> SEQUENCE: 37
ccagaaagau aaaucuacat t                                                21

<210> SEQ ID NO 38
<211> LENGTH: 21
<212> TYPE: DNA
<213> ORGANISM: Artificial
<220> FEATURE:
```

```
<223> OTHER INFORMATION: siRNA - C12orf35_2 antisense

<400> SEQUENCE: 38
uguagauuua ucuuucuggt a                                              21

<210> SEQ ID NO 39
<211> LENGTH: 21
<212> TYPE: DNA
<213> ORGANISM: Artificial
<220> FEATURE:
<223> OTHER INFORMATION: siRNA - Caprin2_6 sense

<400> SEQUENCE: 39
ugaccugccc ugaaagaaat t                                              21

<210> SEQ ID NO 40
<211> LENGTH: 21
<212> TYPE: DNA
<213> ORGANISM: Artificial
<220> FEATURE:
<223> OTHER INFORMATION: siRNA - Caprin2_6 antisense

<400> SEQUENCE: 40
uuucuuucag ggcaggucag t                                              21

<210> SEQ ID NO 41
<211> LENGTH: 21
<212> TYPE: DNA
<213> ORGANISM: Artificial Sequence
<220> FEATURE:
<223> OTHER INFORMATION: siRNA - FAM60A Sense

<400> SEQUENCE: 41
gcuuccagcu cuaacagaat t                                              21

<210> SEQ ID NO 42
<211> LENGTH: 21
<212> TYPE: DNA
<213> ORGANISM: Artificial Sequence
<220> FEATURE:
<223> OTHER INFORMATION: siRNA - FAM60A Antisense

<400> SEQUENCE: 42
uucuguuaga gcuggaagcc a                                              21

<210> SEQ ID NO 43
<211> LENGTH: 21
<212> TYPE: DNA
<213> ORGANISM: Artificial
<220> FEATURE:
<223> OTHER INFORMATION: siRNA - IPO8_1 sense

<400> SEQUENCE: 43
gacccgaacu uugacccuat t                                              21

<210> SEQ ID NO 44
<211> LENGTH: 21
<212> TYPE: DNA
<213> ORGANISM: Artificial
<220> FEATURE:
<223> OTHER INFORMATION: siRNA - IPO8_1 antisense

<400> SEQUENCE: 44
uagggucaaa guucggguct g                                              21
```

```
<210> SEQ ID NO 45
<211> LENGTH: 21
<212> TYPE: DNA
<213> ORGANISM: Artificial
<220> FEATURE:
<223> OTHER INFORMATION: siRNA - IPO8_2 sense

<400> SEQUENCE: 45
cggagacucu ucaaauugat t                                              21

<210> SEQ ID NO 46
<211> LENGTH: 21
<212> TYPE: DNA
<213> ORGANISM: Artificial
<220> FEATURE:
<223> OTHER INFORMATION: siRNA - IPO8_2 antisense

<400> SEQUENCE: 46
ucaauuugaa gagucuccgg a                                              21

<210> SEQ ID NO 47
<211> LENGTH: 21
<212> TYPE: DNA
<213> ORGANISM: Artificial
<220> FEATURE:
<223> OTHER INFORMATION: siRNA - IPO8_3 sense

<400> SEQUENCE: 47
gccugauuga agacgaggat t                                              21

<210> SEQ ID NO 48
<211> LENGTH: 21
<212> TYPE: DNA
<213> ORGANISM: Artificial
<220> FEATURE:
<223> OTHER INFORMATION: siRNA - IPO8_3 antisense

<400> SEQUENCE: 48
uccucgucuu caaucaggct t                                              21

<210> SEQ ID NO 49
<211> LENGTH: 21
<212> TYPE: DNA
<213> ORGANISM: Artificial
<220> FEATURE:
<223> OTHER INFORMATION: siRNA - Dennd5b_2 sense

<400> SEQUENCE: 49
gggucucccu uauucaagat t                                              21

<210> SEQ ID NO 50
<211> LENGTH: 21
<212> TYPE: DNA
<213> ORGANISM: Artificial
<220> FEATURE:
<223> OTHER INFORMATION: siRNA - Dennd5b_2 antisense

<400> SEQUENCE: 50
ucuugaauaa gggagaccct g                                              21

<210> SEQ ID NO 51
<211> LENGTH: 21
<212> TYPE: DNA
<213> ORGANISM: Artificial
<220> FEATURE:
<223> OTHER INFORMATION: siRNA - Amn1_4 sense
```

```
<400> SEQUENCE: 51
gcugcuuaag uauuacugat t                                              21

<210> SEQ ID NO 52
<211> LENGTH: 21
<212> TYPE: DNA
<213> ORGANISM: Artificial
<220> FEATURE:
<223> OTHER INFORMATION: siRNA - Amn1_4 antisense

<400> SEQUENCE: 52
ucaguaauac uuaagcagcc a                                              21

<210> SEQ ID NO 53
<211> LENGTH: 21
<212> TYPE: DNA
<213> ORGANISM: Artificial
<220> FEATURE:
<223> OTHER INFORMATION: siRNA - TMTC1_1 sense

<400> SEQUENCE: 53
guauaccugu gauaaaacat t                                              21

<210> SEQ ID NO 54
<211> LENGTH: 21
<212> TYPE: DNA
<213> ORGANISM: Artificial
<220> FEATURE:
<223> OTHER INFORMATION: siRNA - TMTC1_1 antisense

<400> SEQUENCE: 54
uguuuuauca cagguauaca t                                              21

<210> SEQ ID NO 55
<211> LENGTH: 21
<212> TYPE: DNA
<213> ORGANISM: Artificial
<220> FEATURE:
<223> OTHER INFORMATION: siRNA - TMTC1_2 sense

<400> SEQUENCE: 55
cggugaaugu cauucuacat t                                              21

<210> SEQ ID NO 56
<211> LENGTH: 21
<212> TYPE: DNA
<213> ORGANISM: Artificial
<220> FEATURE:
<223> OTHER INFORMATION: siRNA - TMTC1_2 antisense

<400> SEQUENCE: 56
uguagaauga cauucaccgc a                                              21

<210> SEQ ID NO 57
<211> LENGTH: 20
<212> TYPE: DNA
<213> ORGANISM: Artificial
<220> FEATURE:
<223> OTHER INFORMATION: PCR20 forward primer

<400> SEQUENCE: 57
accagtgaat aatcgtgttt                                                20

<210> SEQ ID NO 58
<211> LENGTH: 20
```

```
<212> TYPE: DNA
<213> ORGANISM: Artificial
<220> FEATURE:
<223> OTHER INFORMATION: PCR20 reverse primer

<400> SEQUENCE: 58
ctatgagtca atgtcccaag                                           20

<210> SEQ ID NO 59
<211> LENGTH: 23
<212> TYPE: DNA
<213> ORGANISM: Artificial
<220> FEATURE:
<223> OTHER INFORMATION: PCR28 forward primer

<400> SEQUENCE: 59
cacacacaac ctcctaacaa ccc                                       23

<210> SEQ ID NO 60
<211> LENGTH: 20
<212> TYPE: DNA
<213> ORGANISM: Artificial
<220> FEATURE:
<223> OTHER INFORMATION: PCR28 reverse primer

<400> SEQUENCE: 60
ttccgcaccg actcagttct                                           20
```

EUKARYOTIC CELLS AND METHODS FOR RECOMBINANTLY EXPRESSING A PRODUCT OF INTEREST

FIELD OF THE DISCLOSURE

The present disclosure concerns the field of recombinant expression technologies. It inter alia provides altered eukaryotic cells which are capable of expressing a product of interest with increased stability as well as their use in recombinant expression methods. Furthermore, tools are provided which allow early in the selection process the identification of eukaryotic cells that express a recombinant product with improved stability based on the expression profile of the eukaryotic cell. The eukaryotic cell preferably is a mammalian cell.

BACKGROUND OF THE DISCLOSURE

The market for biopharmaceuticals continues to grow at a high rate as biopharmaceuticals become more and more important for today's medicine. Currently, an increasing number of biopharmaceuticals is produced in eukaryotic cells such as in particular mammalian cells. Successful and high yield production of biopharmaceuticals in eukaryotic cells is thus crucial. The time to generate such a cell line producing a therapeutic protein of interest is an essential part of the time needed to bring any biopharmaceutical in the clinic. Furthermore, also considering the production costs for biopharmaceuticals and other recombinant products it is important to have high but in particular also stably expressing recombinant eukaryotic cell lines, in particular mammalian cell lines.

For biopharmaceutical production efficiency's sake in particular on industrial scale, a tremendous effort is put into the clone selection process, with the goal to identify high producing clones with good stability and growth characteristics in a short amount of time. However, even if high expressing clones are identified in the course of the screening process, these initially high expressing clones often lose their advantageous expression characteristics and the expression yield decreases over time. This gradual loss of recombinant protein expression in cell clones during prolonged subculture is a common issue with many cell lines such as CHO cell lines and is referred to as instability. This instability seriously affects the industrial production process of recombinantly produced polypeptides. Causes of production instability are contemplated to be related to loss of recombinant gene copies due to genetic instability of the host cells and epigenetic silencing of transgene sequences. Furthermore, it was found that the instability rate can vary depending on the individual project, i.e. the individual product of interest to be expressed. Instability rates between 25% and up to almost 90% were observed in eukaryotic cell lines. Therefore, care must be taking in order to identify within the population of successfully expressing cells and even among the cell clones which express the protein of interest initially with a good yield those cells, respectively cell clones, which also have a high production stability during prolonged cultivation and therefore, are not prone to a gradual loss of recombinant protein expression. Such clones are also called "stable" clones. During prolonged culturing periods, stable clones should not lose more than 30%, preferably not more than 25% of their initial productivity within a period of 8-12 weeks, e.g. 10 weeks. Productivity is defined as volumetric productivity, which is the expressed amount of protein per volume (e.g. g/L) at a certain time point of cultivation, respectively as cell specific productivity, which is the specific amount of expressed protein per cell per day (e.g. pg/cell/day). In order to avoid that a cell clone is selected for subsequent large scale production which is prone to instability and therefore will lose titer during prolonged culturing, usually extensive stability analyses are performed over several weeks up to several months in order to eliminate those cell clones which become unstable during that time period and to identify the stable clones. Therefore, the generation of recombinant cell clones for production of therapeutic proteins and other recombinant polypeptides that are produced on large scale usually comprises excessive screening of individual clones by time consuming stability studies in order to identify cell clones that show the expression stability necessary for large scale production. This screening practice for eliminating unstable clones and identifying stable clones prolongs the development of biotechnological production processes. Even when using highly stringent selection systems that favour survival of high expressing cells under the used selection conditions, finding a suitable production clone within the surviving population which combines a high expression rate with good growth and stability characteristics is difficult.

It is an object of the invention to improve recombinant production of a product of interest in eukaryotic cells such as in particular mammalian cells. In particular, it is an object of the present invention to provide a novel eukaryotic cell line which upon stable transfection with a polynucleotide encoding a product of interest expresses the product of interest with improved stability characteristics. In particular, it is the object to provide a recombinant eukaryotic cell wherein the risk of a significant productivity loss during prolonged culturing is reduced. Additionally, it is an object to provide an improved method for recombinantly producing a product of interest using stably transfected eukaryotic cells, in particular mammalian cells. Furthermore, it is one object to provide analysis tools that allow discriminating between stable and unstable cell clones at an early stage of the development process.

SUMMARY OF THE DISCLOSURE

The present disclosure is inter alia based on the unexpected finding that altering the genome of a eukaryotic cell to impair the effect of protein FAM60A in said cell, e.g. by reducing or eliminating the functional expression of the FAM60A gene, significantly increases the expression stability of a recombinant product of interest in said cells. With the FAM60A gene, a key gene was identified that influences the stability of recombinant expression. Impairing the effect of FAM60A in the cells allows to significantly improve the recombinant production of a product of interest by increasing the expression stability. As is shown in the examples, when using the novel eukaryotic cells described herein as host cells, recombinant cell clones are obtained after selection which show significantly improved stability characteristics. Pronounced losses in expression stability during prolonged culturing are rarer with respective host cells and furthermore, if occurring, result in a less dramatic decrease in the productivity compared to cells wherein the genome is not altered to impair the effect of protein FAM60A in the cell. The abundance of stable clones is increased upon stable transfection. Therefore, stability analyses for identifying host cells that are not or are less prone to instability may be shortened or even skipped. This is an important advantage as it shortens the time that is required for obtaining stably expressing cell clones that express the recombinant product of interest with good yield over a prolonged time period and which accordingly, are suitable for large scale production purposes. Therefore, the present invention significantly reduces the screening effort and makes an important contribution to the prior art.

According to a first aspect, the present disclosure provides an isolated eukaryotic cell, wherein the genome of the eukaryotic cell is altered so that the effect of protein FAM60A is impaired in said cell and wherein said cell comprises integrated into its genome a heterologous polynucleotide encoding a product of interest. The effect of protein FAM60A can be impaired in said cell e.g. by reducing or eliminating functional expression of the endogenous gene FAM60A, e.g. by gene silencing, gene deletion or by mutating the gene so that a non- or less functional protein is expressed. Other options are also described herein.

According to a second aspect, a method is provided for selecting a host cell which recombinantly expresses a product of interest, comprising
(a) providing eukaryotic cells according to the first aspect as host cells; and
(b) selecting one or more host cells expressing the product of interest.

According to a third aspect, a method is provided for recombinantly producing a product of interest, comprising using a eukaryotic cell according to the first aspect as host cell for recombinant expression of the product of interest. The product of interest is encoded by the heterologous polynucleotide that is stably integrated into the genome of the eukaryotic cell according to the first aspect. As described above, due to their favourable expression stability characteristics, these novel eukaryotic cells are particularly suitable as host cells for recombinant production of a product of interest.

According to a fourth aspect, a method is provided for producing a eukaryotic cell suitable for recombinant production of a product of interest, comprising impairing the effect of protein FAM60A in an eukaryotic cell by altering the genome of said cell and stably transfecting into said cell at least one expression vector comprising a polynucleotide encoding a product of interest. The effect of FAM60A can be impaired e.g. by reducing or eliminating functional expression of gene FAM60A in said cell.

According to a fifth aspect, a method is provided for analyzing eukaryotic cells for their suitability as host cells for stably expressing a recombinant product of interest, comprising analyzing directly or indirectly whether the effect of protein FAM60A is impaired in said cells. This method can be advantageously used e.g. in combination with the method according to the fourth aspect in order to identify whether a eukaryotic cell was obtained, wherein the effect of protein FAM60A is impaired in the cell. Furthermore, this method can be used as analytical tool in order to discriminate early in the selection process between stable and unstable cell clones that express the product of interest.

According to a sixth aspect, the present disclosure pertains to the use of an isolated eukaryotic cell for recombinantly expressing a product of interest, wherein the genome of the eukaryotic cell is altered so that the effect of protein FAM60A is impaired in said cell.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

A corresponding overview over the telomeric region of chromosome 6 of mouse can be found e.g. in the Ensembl database. Chromosome 6 of mouse has a structure which corresponds to chromosome 8 of Chinese hamster. The subsequent link of the Ensemble database shows the telomeric region of chromosome 6 of mouse which contains the FAM60A gene:
http://www.ensembl.org/Mus_musculus/Location/View?db=core;g=ENSMUSG00000039985; r=6: 148921035-148946467

Figure 1:
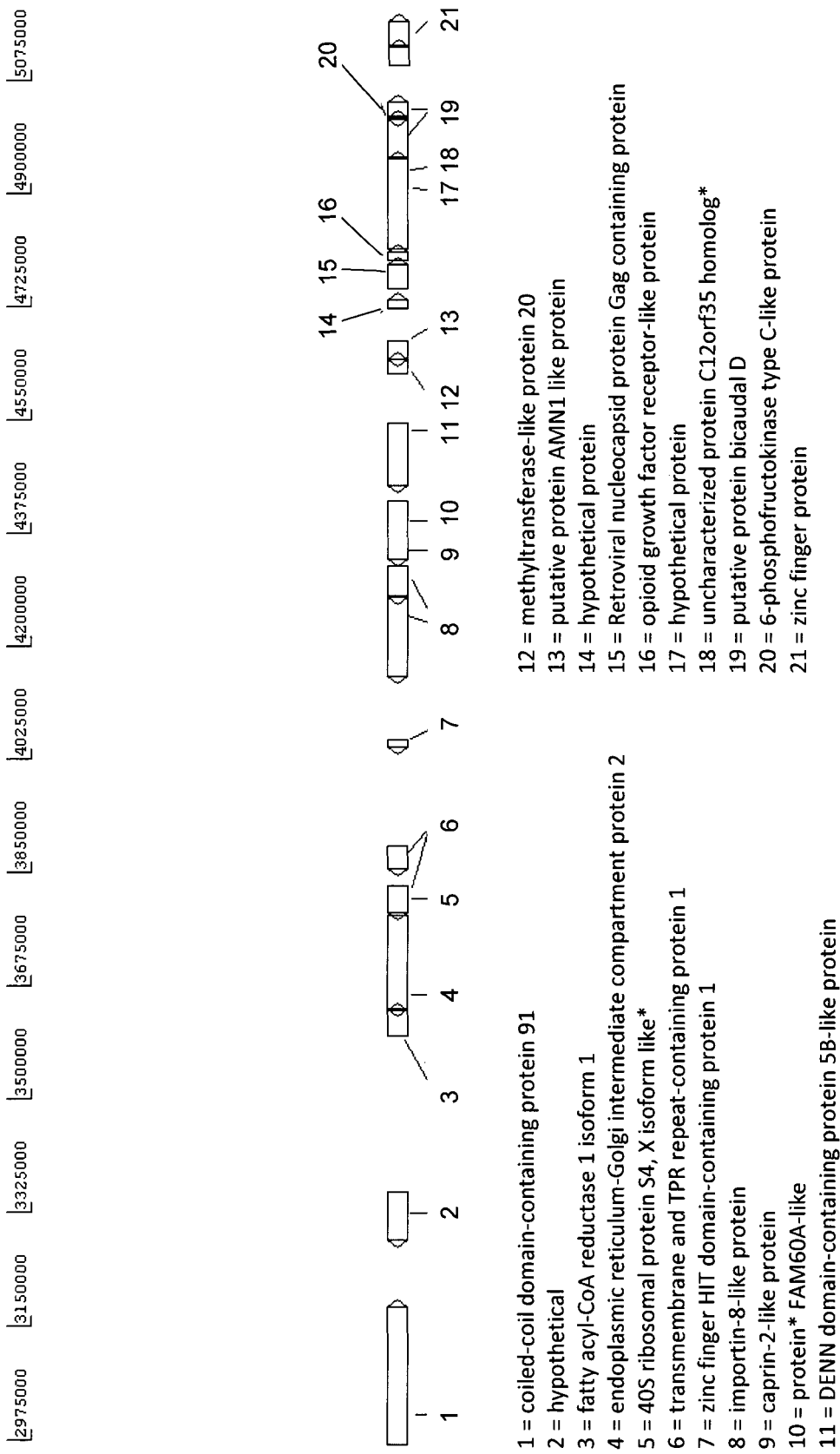
FIG. 1 provides a schematic overview of the telomeric region of chromosome 8 of Chinese hamster ovary (CHO) cells and genes located in said telomeric region. The genomic region depicted in the figure is the result of the merged scaffolds number 6 and 25 on chromosome 8. An overview over genes and putative genes on chromosome 8 of CHO cells can be found using the gene bank annotation file associated with the assembly of Brinkrolf et al. (Nature Biotechnology Volume 31, 694-695 (2013); see gene bank: APMK00000000, version APMK01000000 as is described in said publication). Furthermore, the Beijing Genomics Institute also provided an annotation of this region (Xu et al, Nature Biotechnology, Volume 29, number 8, 735-741 (2011); see gene bank: AFTD00000000, version AFTD01000000). Annotations which are marked with an * in FIG. 1 are from gene bank file AFTD01000000.

The subsequent Table 1 provides an overview over abbreviations and alternative names (aliases) of genes and encoded products shown in FIG. 1 and indicates the corresponding annotation in mouse and Chinese hamster (according to Brinkrolf et al, 2013 and/or Xu et al, 2011) where feasible. Table 1 also lists alternative names used e.g. in different species. Wherein the present disclosure refers to a specific protein or gene name, this also refers to and encompasses any alternative names of said protein or gene e.g. used to characterize the corresponding gene or protein in a different species. In particular, homologs and orthologs having the same function are encompassed thereby.

TABLE 1

Abbreviations and alternative names (aliases) of products encoded by genes located in chromosome 8 of Chinese hamster or chromosome 6 of mouse.

| Abbreviation | In public annotation of Chinese hamster, the gene product is annotated as | In public annotation of mouse the gene product is annotated as | Aliases (see www.genecards.org) |
| --- | --- | --- | --- |
| Ccdc91 | Coiled-coil domain-containing protein 91 | Coiled-coil domain containing 91 | Coiled-Coil Domain Containing 91<br>P56<br>GGA-Binding Partner<br>P56 Accessory Protein<br>DKFZp779L1558<br>FLJ11088<br>Coiled-Coil Domain-Containing Protein 91 |

TABLE 1-continued

Abbreviations and alternative names (aliases) of products encoded by genes located in chromosome 8 of Chinese hamster or chromosome 6 of mouse.

| Abbreviation | In public annotation of Chinese hamster, the gene product is annotated as | In public annotation of mouse the gene product is annotated as | Aliases (see www.genecards.org) |
|---|---|---|---|
| Far2 | Fatty acyl CoA reductase 1 isoform 1 | Fatty acyl CoA reductase 2 | GGA Binding Partner<br>GGABP<br>Fatty Acyl CoA Reductase 2<br>MLSTD1<br>SDR10E2<br>Male Sterility Domain-Containing Protein 1<br>EC 1.2.1.N2<br>FLJ10462<br>Male Sterility Domain Containing 1<br>Fatty Acyl-CoA Reductase 2<br>Short Chain Dehydrogenase/Reductase Family 10E, Member 2 |
| Ergic2 | Endoplasmic reticulum-Golgi intermediate compartment protein 2 | ERGIC and golgi 2 | ERGIC And Golgi 2<br>PTX1<br>Erv41<br>Cd002<br>CD14 Protein<br>Endoplasmic Reticulum-Golgi Intermediate Compartment Protein 2<br>ERV41<br>CDA14 |
| RPS4Y2 | 40S ribosomal protein S4, X isoform like | Ribosomal protein S4, Y linked 2 | Ribosomal Protein S4, Y-Linked 2<br>RPS4Y2P<br>Ribosomal Protein S4, Y-Linked 2 Pseudogene<br>40S Ribosomal Protein S4, Y<br>40S Ribosomal Protein S4, Y Isoform 2 |
| Tmtc1 | Transmembrane and TPR repeat-containing protein 1 | Transmembrane and tetratricopeptide repeat containing 1 | Transmembrane And Tetratricopeptide Repeat Containing 1<br>OLF<br>ARG99<br>FLJ31400<br>FLJ41625<br>TMTC1A<br>Transmembrane And Tetratricopeptide Repeat Containing 1A<br>Transmembrane And TPR Repeat-Containing Protein 1 |
| Zfp 1 | Zinc finger HIT domain-containing protein1 | | ZFP1 Zinc Finger Protein<br>ZNF475<br>Zinc Finger Protein 475<br>FLJ34243<br>Zinc Finger Protein 1<br>Zinc Finger Protein 1 Homolog (Mouse)<br>Zfp-1<br>Zinc Finger Protein 1 Homolog |
| IPO8 | Importin-8-like | Importin-8 | Importin 8<br>RANBP8<br>RAN Binding Protein 8<br>Ran-Binding Protein 8<br>IMP8<br>Imp8<br>Importin-8<br>RanBP8 |
| Caprin2 | Caprin-2-like protein | Caprin family member 2 | Caprin Family Member 2<br>C1QDC1<br>EEG1<br>RNG140<br>Caprin-2<br>Cytoplasmic Activation/Proliferation-Associated Protein 2<br>Gastric Cancer Multidrug Resistance-Associated Protein<br>C1q Domain-Containing Protein 1<br>RNA Granule Protein 140<br>FLJ11391<br>FLJ22569<br>C1q Domain Containing 1 |

TABLE 1-continued

Abbreviations and alternative names (aliases) of products encoded by genes located in chromosome 8 of Chinese hamster or chromosome 6 of mouse.

| Abbreviation | In public annotation of Chinese hamster, the gene product is annotated as | In public annotation of mouse the gene product is annotated as | Aliases (see www.genecards.org) |
|---|---|---|---|
| FAM60A | Protein FAM60A-like | Family with sequence similarity 60, member A | EEG-1<br>KIAA1873<br>Protein EEG-1<br>Family With Sequence Similarity 60, Member A<br>C12orf14<br>TERA<br>Tera Protein Homolog<br>Chromosome 12 Open Reading Frame 14<br>Protein FAM60A |
| Dennd5b | Denn domain-containing protein 5B-like | DENN/MADD domain containing 5B | DENN/MADD Domain Containing 5B<br>Rab6IP1-Like Protein<br>MGC24039<br>DENN Domain-Containing Protein 5B |
| METTL20 | Methyltransferase-like protein 20 | 4833442J19Rik | METTL20<br>C12orf72<br>DKFZp451L235<br>MGC50559<br>Chromosome 12 Open Reading Frame 72<br>Methyltransferase-Like Protein 20<br>EC 2.1.1. |
| AMN1 | Putative protein AMN1 like protein | Antagonist of mitotic exit network 1 | Antagonist Of Mitotic Exit Network 1 Homolog (*S. Cerevisiae*)<br>Protein AMN1 Homolog |
| C12orf35 | Opioid growth factor receptor-like protein<br>Uncharacterized protein C12orf35 homolog | Opioid growth factor receptor-like protein<br>likely orthologue of H. sapiens chromosome 12 open reading frame 35 (C12orf35); 2810474O19Rik | KIAA1551,<br>C12orf35<br>FLJ10652,<br>FLJ20696<br>Chromosome 12 Open Reading Frame 35<br>Uncharacterized Protein C12orf35<br>Uncharacterized Protein KIAA1551 |
| Bicd 1 | Putative protein bicaudal D | Bicaudal D homolog 1 | Bicaudal D Homolog 1 (*Drosophila*)<br>Bic-D 1<br>Bicaudal D (*Drosophila*) Homolog 1<br>BICD<br>Cytoskeleton-Like Bicaudal D Protein Homolog 1<br>Protein Bicaudal D Homolog 1 |

Figure 2:
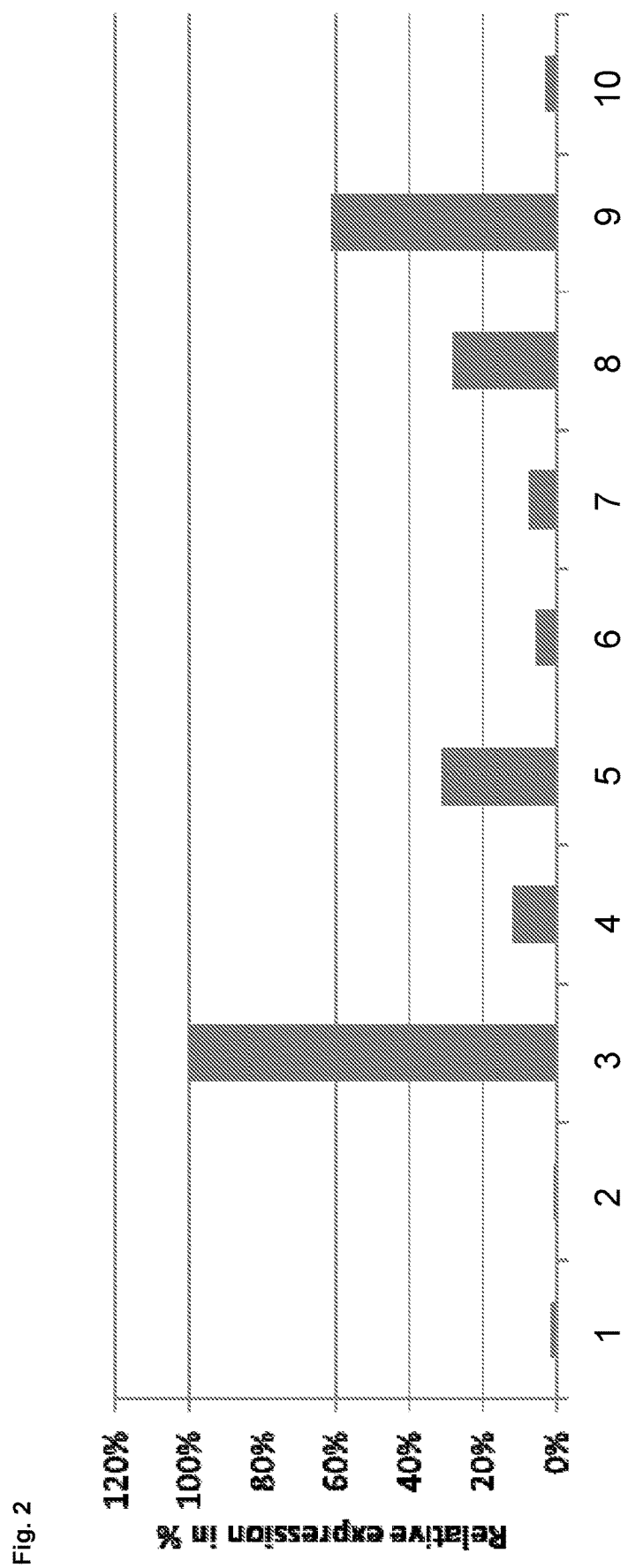

FIG. 2 shows the relative expression levels of genes located in the telomeric region of chromosome 8 in a CHO cell line, namely TMTC1 (1), RPS4Y2 (2), IPO8 (3), CAPRIN2 (4), FAM60A (5), Dennd5b (6), METTL20 (7), AMN1 (8), C12orf35 (9), Bicd1 (10).

Figure 3:
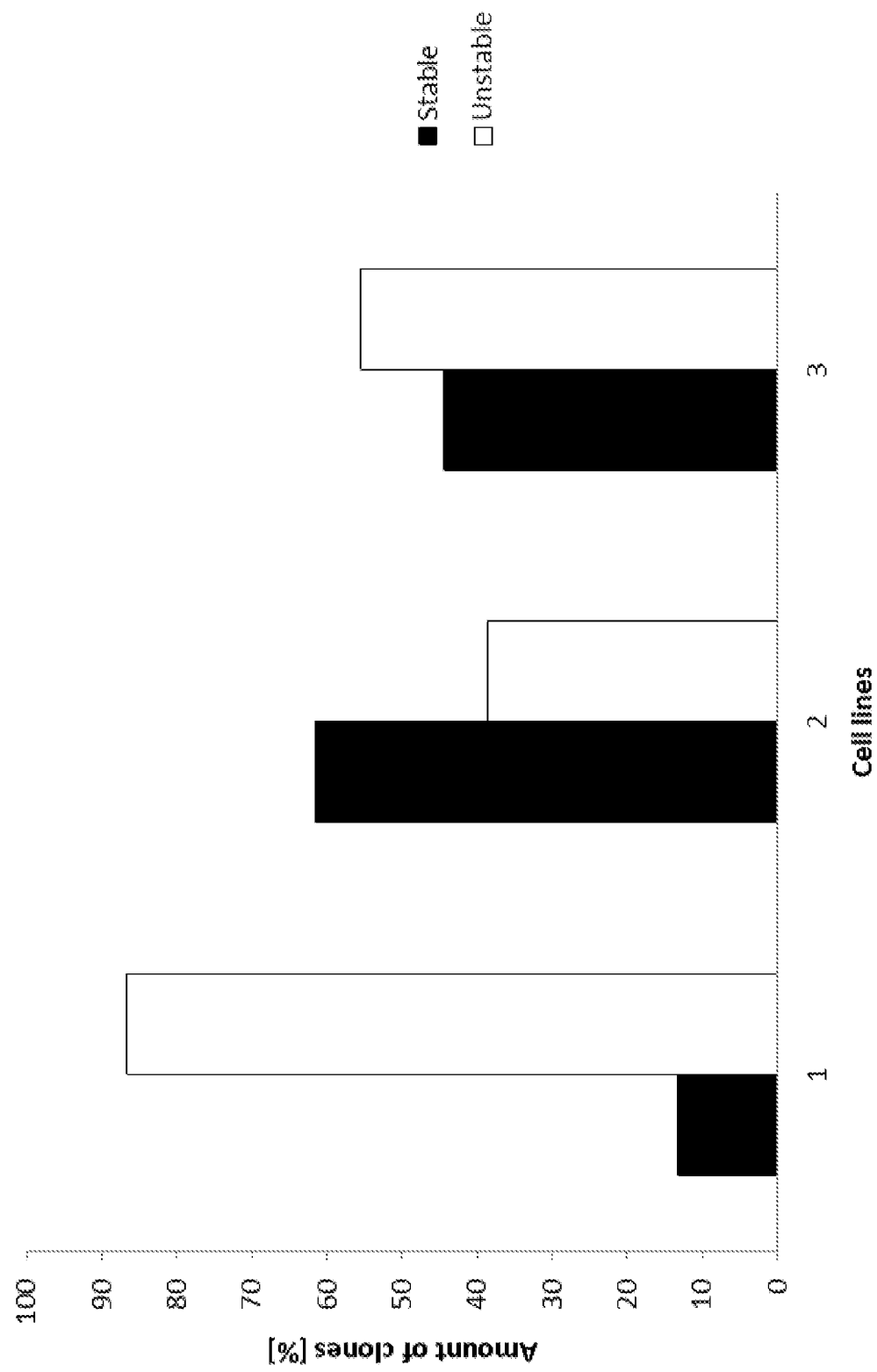

FIG. 3 shows the results of stability tests performed for 7/8 weeks with three different cell clones (CHO wildtype and two FAM60A knock-out clones s16 and s23 derived from said wildtype) following stable transfection with an expression vector encoding an antibody as product of interest. (1) shows the stability results obtained with the parental wildtype cells (derived from CHO-K1); (2) shows the stability results with the FAM60A knock-out clone s16; (3) shows the stability results with the FAM60A knock-out clone s23. As can be seen, the expression stability was significantly increased in the cell clones that derived from the FAM60A knock-out cells (see (2) and (3)). The number of stable clones was significantly increased when using the FAM60A knock-out cells for recombinant expression. Thus, impairing the effect of FAM60A in the host cell, here by gene knock-out, significantly improved the expression stability.

Figure 4:
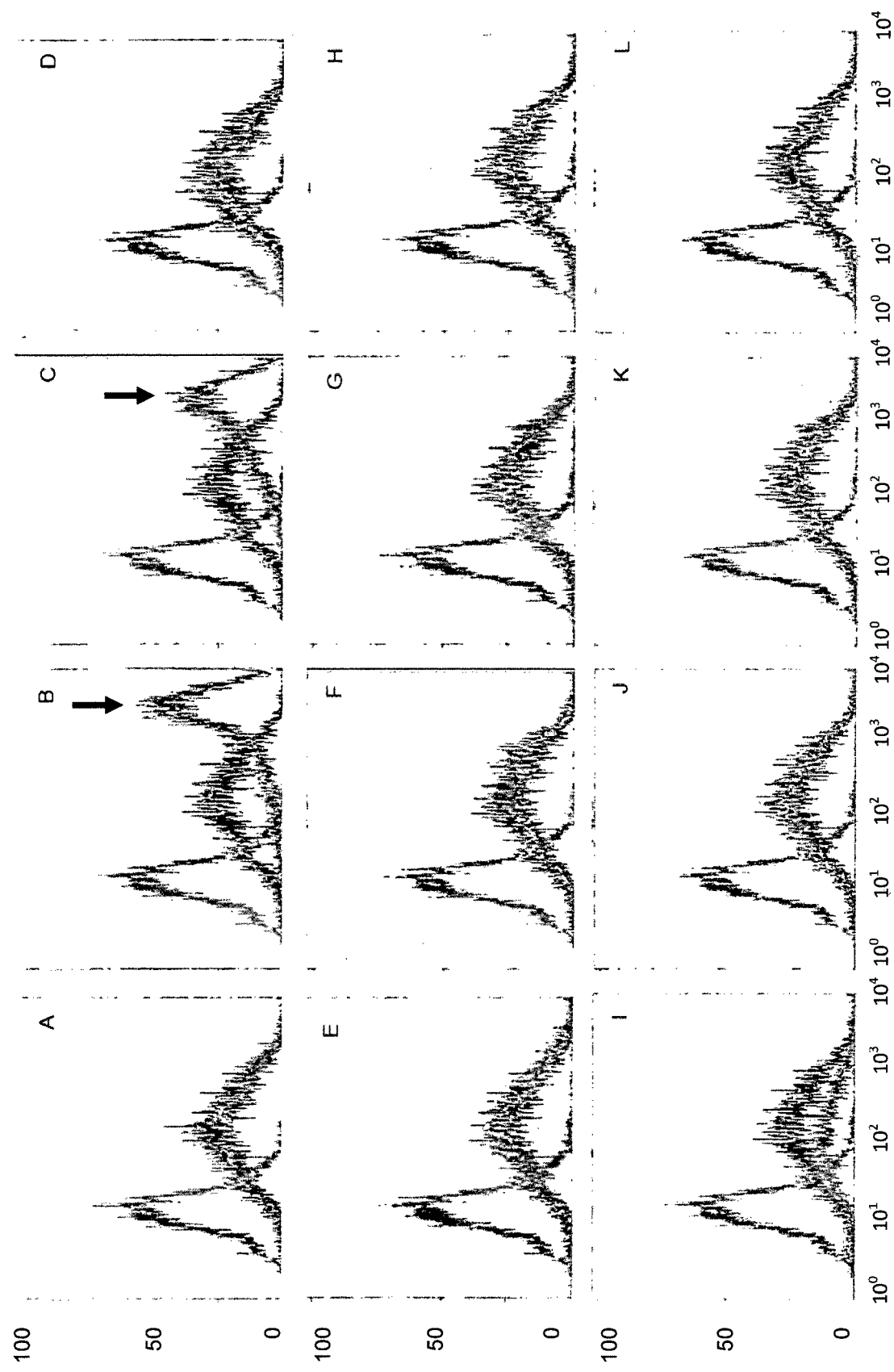

FIG. 4A to L show FACS profiles obtained after reducing the expression of different target genes located in the telomeric region of chromosome 8 of Chinese hamster (CHO) cells using siRNAs. Cells that were stably transfected with an expression vector and expressed the encoded antibody as product of interest were fluorescently stained to detect the amount of recombinantly expressed antibody. The higher the intensity in the FACS profile, the more the antibody is expressed by the stained cell. The left peak shown in the FACS profile corresponds to the parental cell line (not transfected and hence not expressing the antibody) which was included for comparative purposes. The two other curves represent results obtained for a cell clone that was stably transfected with the expression vector and which recombinantly expresses the antibody. This cell clone was transfected with either a siRNA negative control (dark curve; no effect on expression of any gene) or with a siRNA that reduces the expression of a target gene (light grey curve). If silencing of the target gene does not have an effect on recombination expression of the antibody, the fluorescent curve for the siRNA control and the target siRNA overlap and remain the same. If silencing of the target gene increases the expression rate of the recombinantly expressed antibody, the intensity of the corresponding FACS profile increases and shifts to the right. A: gene Mettl20_1, 125 pmol, 24.9%; B: gene C12orf35_1, 125 pmol, 30.6%; C: gene C12orf35_2, 150 pmol, 31.7%; D: gene Caprin2_6, 100 pmol, 53.3%; E: FAM60A_3, 150 pmol, 48%; F: Ipo8_1, 125 pmol, 20.3%; G: Ipo8_2, 150 pmol, 57.5%; H: Ipo8_3, 150 pmol, 21.5%; I: Dennd5b_2, 100 pmol, 36.9%; J: Amn1_4, 125 pmol, 30.8%; K: TMTC1_1, 150 pmol, 60.6%; L:TMTC1_2, 150 pmol, 53.4% (percentage values correspond to mRNA expression of the target gene between reference siRNA versus ctrl siRNA). FIGS. 4B and C show that a downregulation of gene C12orf35 significantly increases expression of the recombinant antibody and thus results in a higher productivity as is indicated by the clear shift of the FACS profile to the right (see light grey curve on the right, also marked with an arrow). Therefore, according to one embodiment, the effect of the expression product of gene C12orf35 is additionally impaired in the host cell in order to improve the yield.

Figure 5:
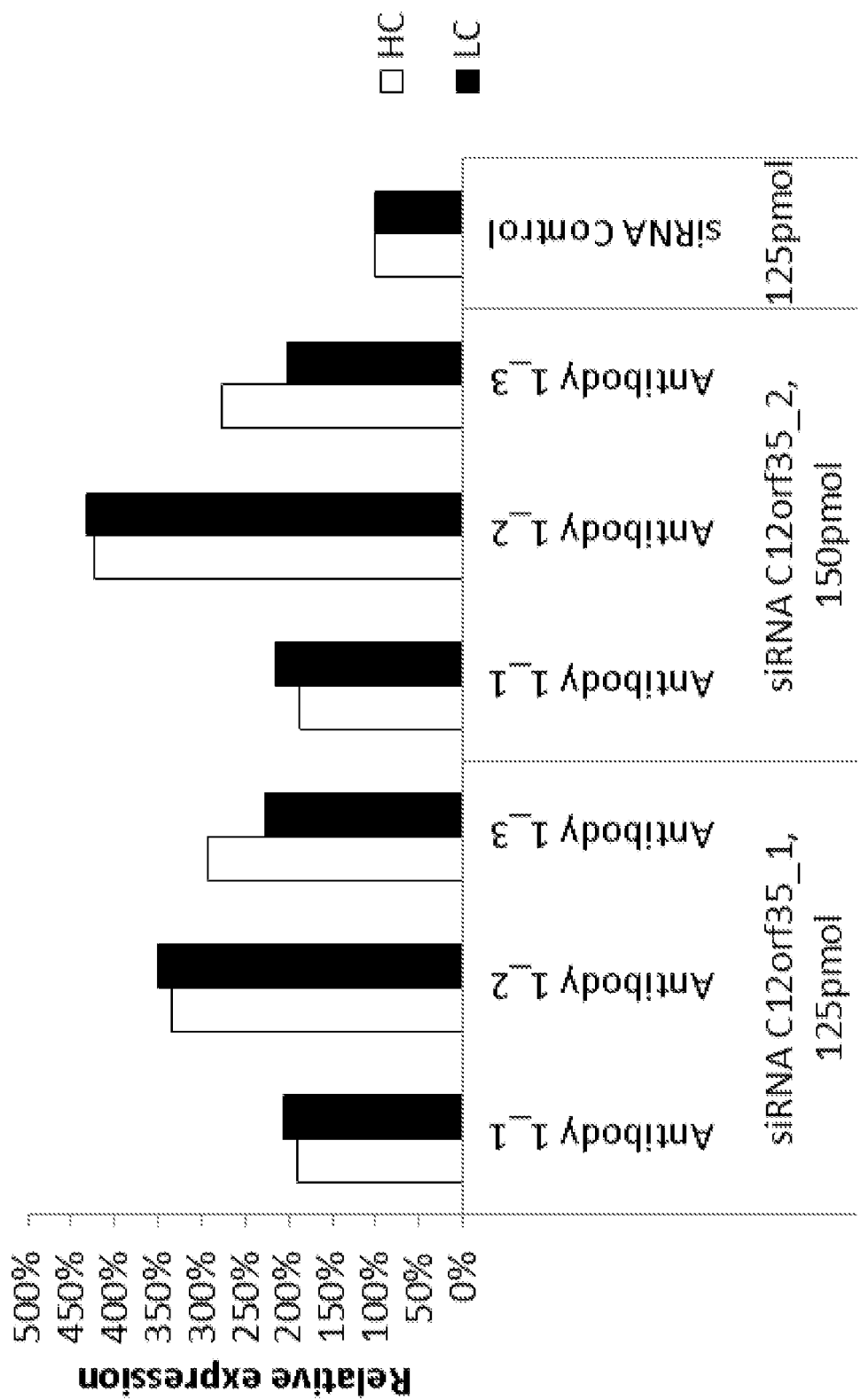
Figure 6:
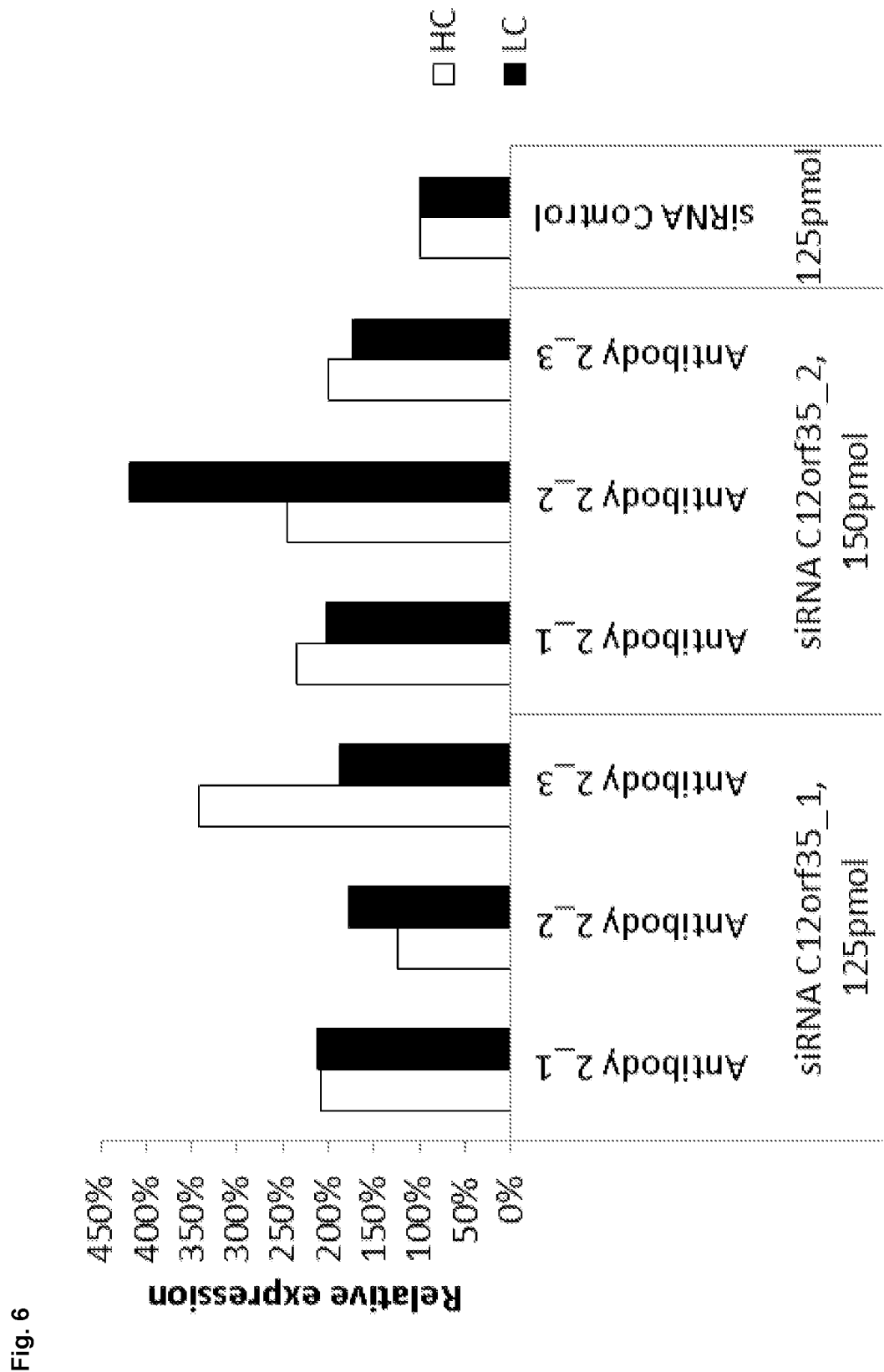

FIGS. 5 and 6 show the mRNA expression levels of the antibody light and heavy chains of two different model polypeptides of interest (antibody 1 and 2) in different clones and pools in each case after reducing expression of gene C12orf35 in CHO cells by RNAi. The mRNA levels of the antibody chains are upregulated, if expression of gene C12orf35 is reduced by gene silencing. Thus, reduction of C12orf35 expression surprisingly leads to higher mRNA levels of HC and LC.

Figure 7:
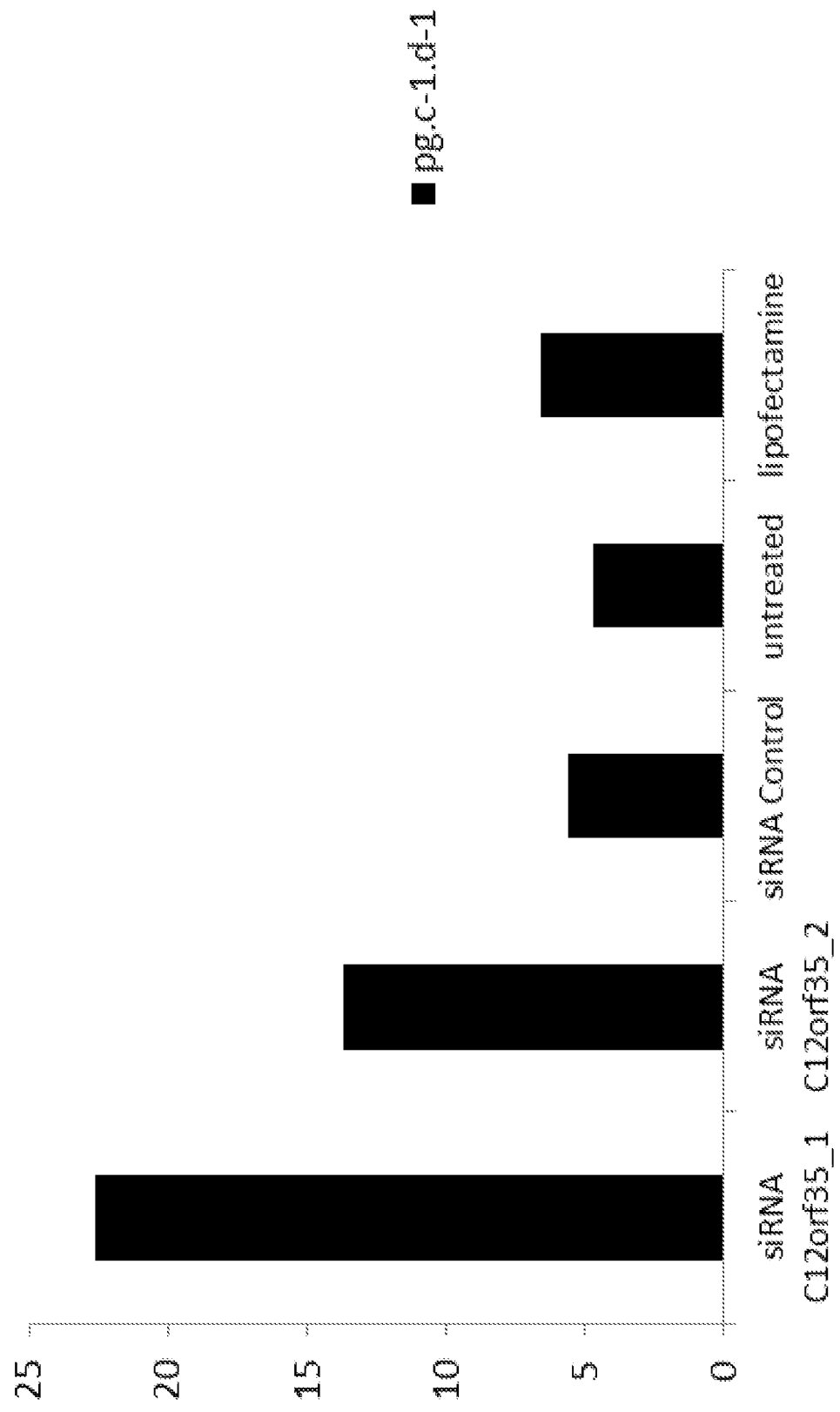

FIG. 7 shows that upon silencing of gene C12orf35 using siRNA, significantly higher cell specific expression titers are obtained (calculated from days 3, 4, 5 and 6 of cultivation).

Figure 8:
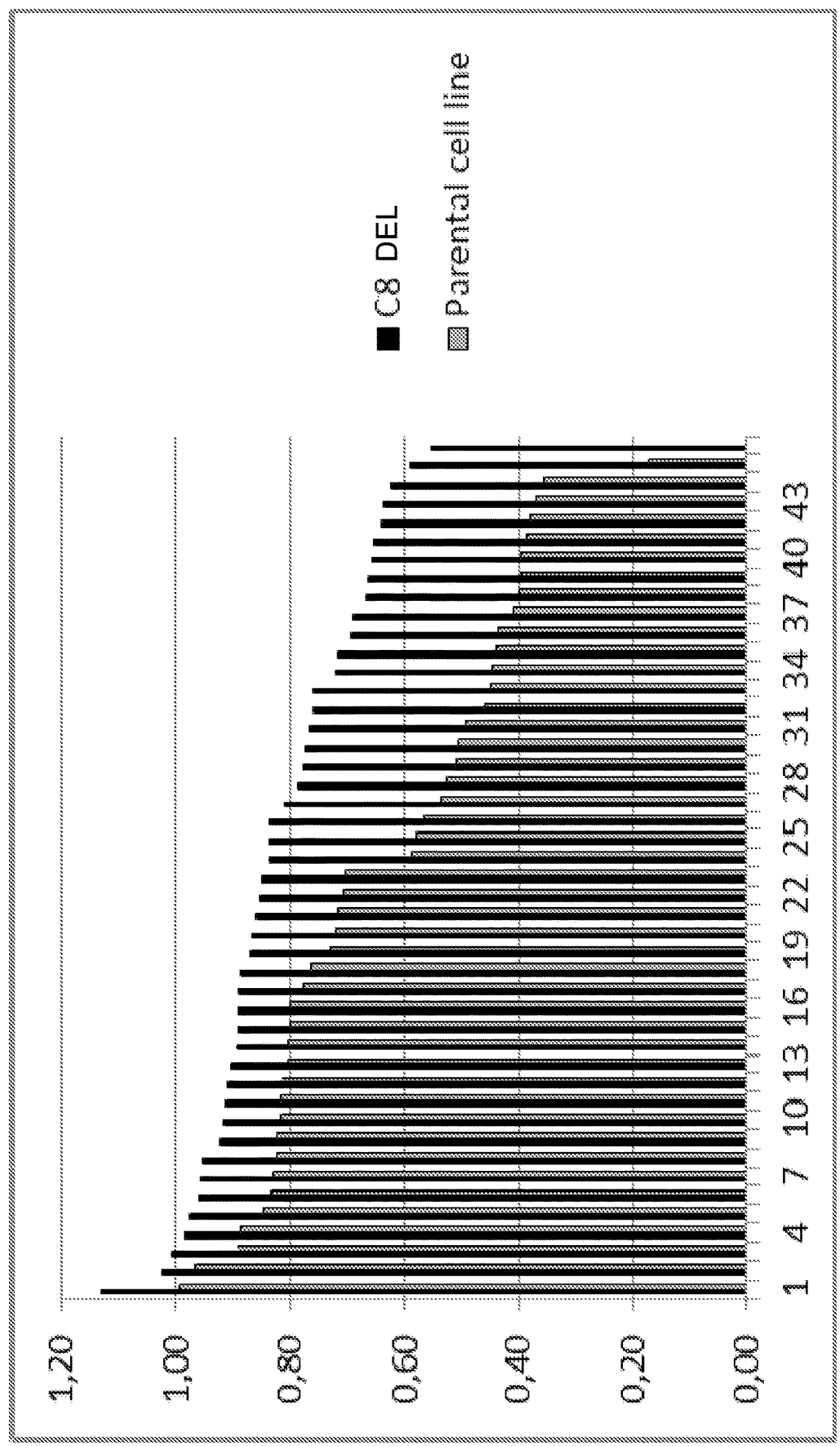

FIG. 8 shows that the 46 highest producing clones (black) derived from a CHO cell line in which the telomeric region comprising gene FAM60A and gene C12orf35 on chromosome 8 (q arm) is deleted (C8DEL) have higher titers compared to the 45 highest producing clones obtained from the parental cell line which were tested to be IPO8 positive (grey).

Figure 9:
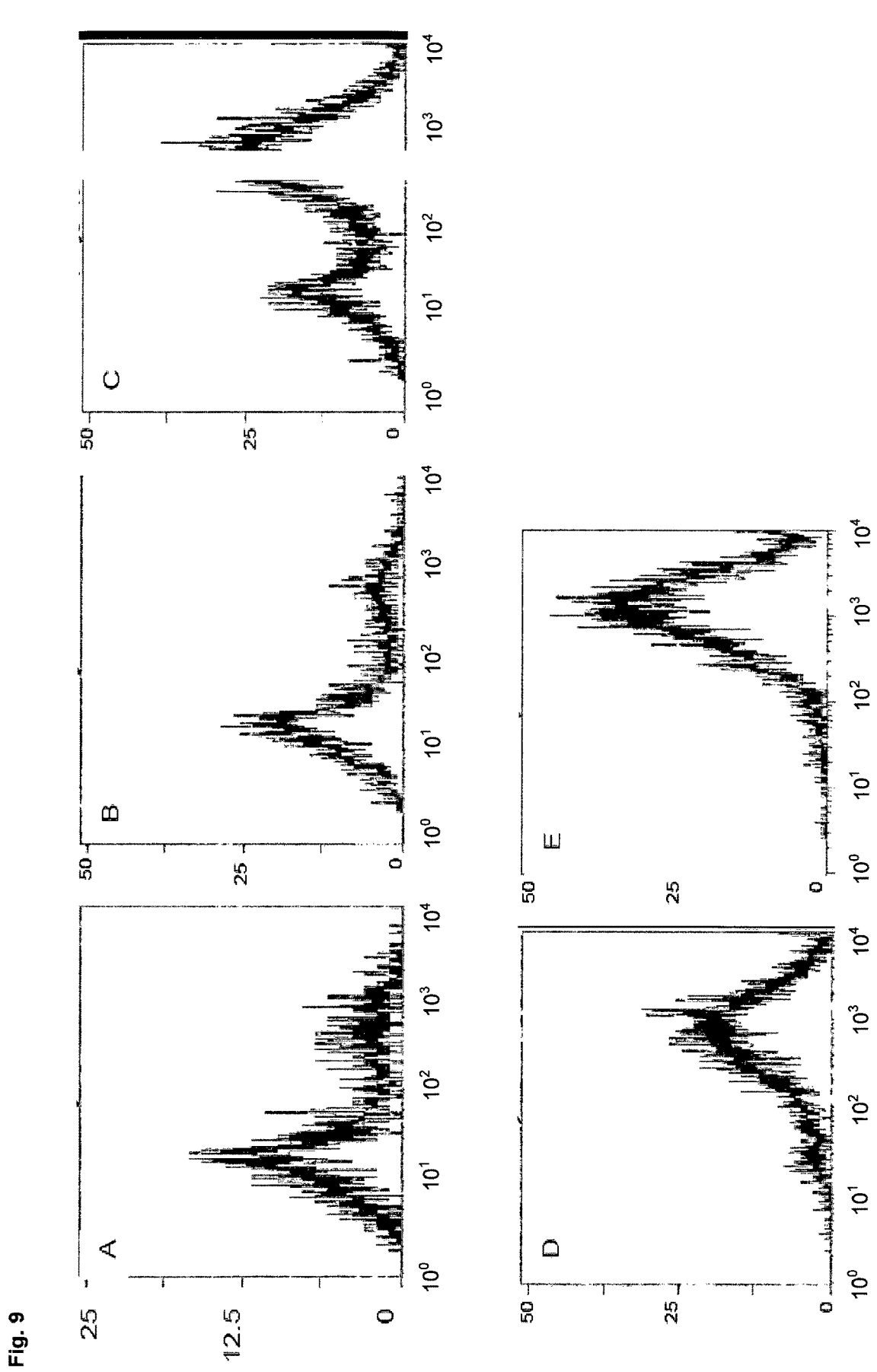

FIG. 9 shows FACS profiles of stably transfected C8DEL cell pools after selection using a folate receptor/DHFR system. The concentration of MTX was increased from A to E (A: no MTX; B: 1 nM MTX; C: 5 nM MTX; D: 10 nM MTX; E: 50 nM MTX). Recombinant antibody expression was detected based on fluorescence. At 50 nM MTX, predominantly high producing cells were comprised in the obtained pool as is demonstrated by FACS analysis. The obtained pool profile remarkably resembled the profile of a cell clone. This supports the extraordinary improvement the technology described herein achieves on the expression characteristics of a recombinant host cell.

DETAILED DESCRIPTION OF THE DISCLOSURE

The present disclosure is inter alia based on the surprising finding that eukaryotic cells, in which the effect of protein FAM60A is impaired, e.g. by reducing or eliminating functional expression of the endogenous FAM60A gene in said cell, e.g. by deleting said gene or by introducing mutations into the coding sequence, are upon stable transfection capable of expressing a recombinant product of interest with significantly improved stability characteristics. As is shown by the examples for mammalian cells, respectively altered cells surprisingly show very stable expression characteristics during prolonged culturing times, thereby allowing to shorten or even skip time-consuming stability analyses for identifying stable clones. In a population of successfully transfected host cells, the number of host cells which lose their favorable expression characteristics during prolonged culturing periods is significantly reduced when using respectively altered eukaryotic cells. Thus, because of their favorable stability characteristics, these altered eukaryotic cells are particularly suitable as host cells for recombinant production technologies and can be used for recombinant production of a product of interest. Based on this surprising finding that gene FAM60A has a strong impact on recombinant expression stability in eukaryotic host cells, the present disclosure also provides novel selection and production methods and associated technologies which allow improving the recombinant production of a product of interest. Therefore, the present disclosure makes an important contribution to the prior art.

The individual aspects and suitable and preferred embodiments thereof will now be described in detail.

A. Modified Eukaryotic Cells

According to a first aspect, the present disclosure provides an isolated eukaryotic cell, wherein the genome of the eukaryotic cell is altered so that the effect of protein FAM60A is impaired in said cell and wherein said cell comprises integrated into its genome a heterologous polynucleotide encoding a product of interest. As is shown in the examples, these altered cells show a significant higher production stability of the product of interest compared to unmodified cells wherein the effect of FAM60A is not impaired. The abundance of cells which exhibit stable expression characteristics is increased in the population of transfected cells as was shown for the preferred embodiment wherein a mammalian cell is used as eukaryotic cell. This improved expression stability allows to shorten or even skip time consuming long-term stability studies of high expressing cell clones. Further advantages are also described in the following and are also apparent from the examples. Thus, using these advantageous novel eukaryotic cell lines for recombinant production of a product of interest reduces screening efforts for identifying high expressing cells or cell clones with stable expression characteristics and in particular reduces the time needed for obtaining stable cell clones suitable for producing the product of interest on large scale. Thus, these altered eukaryotic cell lines have important advantages when being used as host cells for recombinant production technologies.

FAM60A is a sub-unit of the SIN3-histone deacetylase (HDAC) complex (SIN3/HDAC complex) that functions in transcriptional repression (Munoz et al., 2012, THE JOURNAL OF BIOLOGICAL CHEMISTRY VOL. 287, NO. 39, pp. 32346-32353; Smith et al., 2012, Mol Cell Proteomics 11 (12): 1815-1828). Histone deacetylases (HDAC) catalyze the removal of acetyl groups from histones. Acetylation of histones on lysines is a major mechanism for modulating chromatin conformation. Histone acetylation promotes a relaxed, transcriptionally active chromatin state whereas deacetylation catalyzed by histone deacetylases (HDACs) favor a silent, inactive state. Database analysis revealed the presence of at least one FAM60A ortholog in most metazoans, but not in nematodes. The FAM60A gene is conserved in metazoans and can be found in all vertebrate and most invertebrate genomes that have been completely sequenced. E.g. a 100% sequence identity of FAM60A protein can be found between human, rat, mouse and cow. Sequence similarity research of FAM60A homologs indicates that predominantly, there is only a single representative member of this family in the genome. There are only few exceptions. According to the Smith et al, 2012, the FAM60A protein has a unique sequence lacking any known protein domains. Moreover, it was described by Smith et al 2012, that it does not exhibit any sequence homology to other known proteins in the human proteome. Sequence comparison between FAM60A proteins from different species showed that the FAM60A protein generally comprises three regions: (1) an N-terminus comprising highly conserved segments in all metazoans (2) a middle region which is highly conserved across vertebrates whereas in invertebrates it consists of a non-conserved spacer of a variable length (3) a C-terminus comprising highly conserved segments in all metazoans. Thus, highest conservation was observed in the FAM60A N- and C-terminal regions.

As described above, research indicates that FAM60A associates with SIN3/HDAC complexes in various eukaryotic cell types such as in particular mammalian cells. However, to date, functional information about FAM60A is quite restricted. Recent functional studies (see Smith et al, 2012) indicate that FAM60A may repress gene expression and regulates a specific subset of genes. Smith et al 2012 report a role of FAM60A in the regulation of the TGF-beta signaling pathway, which plays a pivotal role in processes like cancer progression, metastasis, cell migration and immune surveillance. There are findings indicating that FAM60A acts as a transcriptional repressor of components of the TGF-beta signaling pathway whereas this FAM60A function seems to be permitted via its role in the SIN3-HDAC complex. Depletion of FAM60A in different cancer cell lines using siRNA against FAM60A resulted in a change of normal cancer cell morphology. Furthermore, it was found that FAM60A protein levels do periodically change within the course of the cell cycle in U2OS cells (Munoz et al, 2012). FAM60A knock-down experiments using FAM60A siRNA in U2OS human bone osteosarcoma cells revealed that FAM60A restrains cyclin D1 gene expression. Against this scientific background, it was highly surprising to find that impairing the effect of protein FAM60A in a eukaryotic cell such as preferably a mammalian cell, significantly increases the stability of heterologous gene expression in said cell without negatively affecting other characteristics of the cell that are important for recombinant expression. This correlation between the effects of protein FAM60A and the expression stability during prolonged culturing of the cells was unexpected.

As described, the FAM60A gene is endogenously expressed in metazoan and hence in mammalian species such as human, mouse, rat and hamster and the amino acid sequence of FAM60A is highly conserved in mammalian species as well as in vertebrates. The altered eukaryotic cell according to the first aspect is derived from a eukaryotic cell which endogenously expresses FAM60A. For the ease of simplicity, the protein FAM60A as well as the FAM60A gene encoding protein FAM60A is spelled herein in capital letters even though in some species a different spelling is used for the gene and/or the protein. The sequence listing shows exemplary amino acid sequences of known and/or predicted FAM60A proteins of different vertebrate species, namely Homo sapiens (SEQ ID NO: 1), Rattus norvegicus (SEQ ID NO: 2), Mus musculus (SEQ ID NO: 3), Cricetulus griseus (SEQ ID NO: 4), Gallus gallus (SEQ ID NO: 5), Pan troglodytes (SEQ ID NO: 6), Pongo abelii (SEQ ID NO: 7) and Bos taurus (SEQ ID NO: 8). The predicted FAM60A cDNA of Cricetulus griseus is shown in SEQ ID NO: 9 (coding sequence from 14-679; see also NCBI Reference Sequence: XM_003505482.1). Different names can be assigned for protein FAM60A or the FAM60A gene in different species and non-limiting alternative names (aliases) are also listed above in Table 1. The term "FAM60A" as used herein also encompasses any homologs and orthologs of FAM60A which have the same function as FAM60A. According to one embodiment the term "FAM60A" as used herein in particular refers a protein that shares at least 50%, at least 60%, at least 70%, at least 75%, at least 80%, at least 85%, at least 90%, at least 95%, at least 96%, at least 97%, at least 98% or at least 99% homology to one or more of the amino acid sequences shown in SEQ ID NO: 1 to 8. According to one embodiment, the foregoing percentage values refer to polypeptide identity instead of homology. Homology, respectively identity, may be calculated over the entire length of the reference protein. A respective protein preferably has the same function as the protein having an amino acid sequence that is shown in SEQ ID NO: 1 or one or more of SEQ ID NO: 2 to 8, preferably SEQ ID NO: 4. The FAM60A protein has not been described in detail in the literature. Thus, it was highly surprising that the expression stability of a recombinant host cell can be improved, if the genome of the host cell is altered so that the effect of endogenous protein FAM60A is impaired in the cell, as can be e.g. achieved by reducing or eliminating the functional expression of the FAM60A gene in said cell. It was unexpected that FAM60A influences the expression stability of a recombinant product of interest.

The FAM60A gene encoding the FAM60A protein can be modified as described herein in order to impair the effect of FAM60A in the cell. This can be achieved e.g. by genetic engineering technologies such as gene knock-out technologies. The genomic gene sequence of different mammalian species is known, and is e.g. described in Homo sapiens (NCBI Gene-ID: 58516); Rattus norvegicus (NCBI Gene-ID: 686611); Mus musculus (NCBI Gene-ID: 56306); Bos Taurus (NCBI Gene-ID: 538649) and others. Transcript variants may exist in a species-dependent manner and in different numbers. E.g. the human FAM60A gene expresses 3 putative transcript isoforms which differ in the UTRs but encode the same protein.

The present disclosure inter alia pertains to modified eukaryotic cells, such as preferably mammalian cells, wherein the genome of the eukaryotic cell is altered so that the effect of protein FAM60A, which is endogenously expressed by a corresponding unmodified eukaryotic cell, is impaired. This modification allows to increase the number of stably expressing cells in the cell population that was stably transfected with an expression vector comprising a polynucleotide encoding a product of interest.

There are several possibilities to modify the genome of a cell to impair the effect of protein FAM60A in said cell. The effect of FAM60A may be impaired e.g. on the gene level or on the protein level. The effect of FAM60A can be impaired, for example, by modification of the structure/sequence, the transcription, translation and/or interaction with other components forming the SIN3/HDAC complex. Non-limiting options are described in the following.

According to one embodiment, the effect of protein FAM60A is impaired because the functional expression of gene FAM60A is reduced or eliminated in said cell. As is shown by the examples, altering the expression of gene FAM60A, e.g. by gene knock-out or by reducing the expression level, is a very efficient measure to provide altered cells that express a recombinant product of interest with improved stability characteristics.

Reduction or elimination of functional expression of gene FAM60A may be achieved by various means. Functional expression can be reduced for example by reducing the expression level of FAM60A or by disrupting the function of FAM60A or by a combination of such methodologies. According to one embodiment, the cell is altered so that functional expression of the FAM60A gene is reduced or eliminated by gene knock-out, gene mutation, gene deletion, gene silencing or a combination of any of the forgoing. According to one embodiment, functional expression of gene FAM60A is reduced or eliminated in the cell by gene knockout. A gene knockout is a genetic technique by which a gene is made inoperative by disrupting its function. E.g. a nucleic acid can be inserted into the coding sequence, thereby disrupting the gene function. Furthermore, the complete FAM60A gene or a portion thereof can be deleted, whereby no or no functional protein is expressed by a respectively altered cell. Another option is to introduce one or more knock-out mutations into the coding sequence, which render a non- or a less functional expression product. E.g. one or more frameshift mutations can be introduced into the coding sequence that result in a non- or less-functional expression product. Alternatively or additionally, one or more stop codons can be introduced into the coding sequence so that a truncated, non- or less functional protein is obtained. Furthermore, splicing sites may be altered. Hence, according to one embodiment, the FAM60A gene comprises one or more mutations which provide a non- or less functional expression product. According to one embodiment, one or more mutations are introduced into exon 1 of the FAM60A gene. According to one embodiment, due to the introduced one or more mutations, all or a part of the N-terminal or the C-terminal region of FAM60A is not present in the expression product. Other options include but are not limited to one or more mutations in the promoter, in the 5'- and/or 3' UTRs or other regulatory elements. According to one embodiment, the promoter function of the FAM60A gene is disrupted, e.g. by introducing a promoter deletion or by introducing a construct between the promoter and the transcription start. Methods for achieving a gene knockout to suppress or eliminate expression of the target gene are also well-known to the skilled person and thus, do not need any detailed description herein. Some non-limiting examples are nevertheless described below.

According to one embodiment, the FAM60A gene is functionally knocked out by genetic engineering. Examples include but are not limited to genome editing, such as genome editing with engineered nucleases (GEEN). This is a type of genetic engineering in which DNA is inserted, replaced or removed from a genome using artificially engineered nucleases, or "molecular scissors." The nucleases create specific double-stranded breaks (DSBs) at desired locations in the genome, and harness the cell's endogenous mechanisms to repair the induced break by natural processes of homologous recombination (HR) and nonhomologous end-joining (NHEJ). There are at least four families of engineered nucleases that can be used: Zinc finger nucleases (ZFNs), Transcription Activator-Like Effector Nucleases (TALENs), CRISPR, and engineered meganuclease re-engineered homing endonucleases. TALEN technology was also used in the examples to provide altered mammalian cells wherein the FAM60A gene was knocked out thereby impairing the effect of protein FAM60A in said cells.

According to one embodiment at least one copy and optionally, if more copies of gene FAM60A are present in the genome of the eukaryotic cell, all copies are altered, e.g. knocked-out, deleted or otherwise rendered inoperative, to reduce or eliminate and hence impair the effect of protein FAM60A in the eukaryotic cell. Thus, according to one embodiment, at least one copy of gene FAM60A is deleted or functionally inactivated in the genome of the eukaryotic cell. For example, one or more mutations may be inserted into the one or more copies of the FAM60A gene to provide a non- or less functional expression product or to eliminate or reduce expression in toto and, hence impair the effect of FAM60A in the eukaryotic cell. Thereby, the FAM60A gene is basically inactivated in the genome. According to one embodiment, all copies of gene FAM60A are respectively altered in the eukaryotic cell, which preferably is a mammalian cell.

According to one embodiment, the eukaryotic cell is a metazoan cell, a vertebrate cell or preferably, a mammalian cell. According to one embodiment, a portion of a chromosome is deleted in the said cell, wherein the deleted portion comprises gene FAM60A. According to one embodiment, a chromosomal portion comprising gene FAM60A is deleted in all chromosomes which comprise a copy of gene FAM60A if more than one copy is present. Thereby, all copies of gene FAM60A are deleted from the genome.

According to one embodiment, a portion of the telomeric region of a chromosome is deleted, wherein the deleted portion comprises gene FAM60A. According to a preferred embodiment, the altered cell is a rodent cell. According to one embodiment, the cell is a hamster cell such as e.g. a CHO cell and at least a portion of the telomeric region of chromosome 8 is deleted in the genome, wherein said deleted portion comprises gene FAM60A. The meaning of the term "FAM60A" is explained above and non-limiting alternative names of homologs and orthologs that are also encompassed by the scope of said term are also indicated in Table 1. According to one embodiment, such deletion occurs in the q arm of chromosome 8 of a hamster cell, in particular a Chinese hamster cell, which comprises the FAM60A gene. As is shown by the examples, a CHO cell comprising a respective deletion in the telomeric region of chromosome 8 is particularly suitable as host cell for recombinant expression. After stable transfection with an expression vector, these cells show significant higher expression stability and productivity compared to cells wherein said portion of the telomeric region of chromosome 8 is not lost. Furthermore, the abundance and thus the proportion of stably expressing cells in the transfected cell population is significantly increased. Significant losses in titer during prolonged culturing are rarely observed. Thus, the stability of recombinant expression is significantly improved in such hamster cells which have lost said portion of the telomeric region in chromosome 8. Further important advantages are described in detail in the examples wherein CHO cells in which a respective portion of the telomeric region of chromosome 8 is deleted due to chromosome breakage are further characterized. The advantageous properties render these hamster cells particularly suitable as industrial production cell lines. Alternatively, the altered rodent cell may be a mouse cell wherein at least a portion of the telomeric region of chromosome 6 is deleted in the genome, wherein said deleted portion comprises gene FAM60A. The telomeric region of chromosome 6 of mouse is highly similar to the telomeric region of chromosome 8 of hamster.

According to one embodiment, at least a portion of the telomeric region is deleted or not present in both chromosomes of chromosome pair 8 of hamster (or chromosome pair 6 in case of mouse cells), wherein the deleted portions comprise the FAM60A gene.

According to one embodiment, at least a portion of the telomeric region is deleted in one chromosome of chromosome pair 8 of hamster (or chromosome pair 6 in case of mouse), wherein said deleted portion comprises the FAM60A gene and the expression of gene FAM60A in the other chromosome, if a further copy is present, is reduced or eliminated. Suitable ways to reduce or eliminate the expression of a gene are known to the skilled person and non-limiting examples are also described herein. According to one embodiment, such deletion occurs in the q arm of chromosome 8 of hamster, in particular Chinese hamster.

According to one embodiment, the deleted chromosomal region comprises the FAM60A gene and additionally comprises one or more or all genes selected from the group consisting of Bicd1, C12orf35, Amn1, methyltransferase-like protein 20, Dennd5b, Caprin2 and Ipo8. According to one embodiment, all of the aforementioned genes are deleted. According to one embodiment the deleted chromosomal region additionally comprises at least a portion of or the full gene Tmtc1. In hamster cells such as CHO cells, these genes may be located in the telomeric region of chromosome 8. According to one embodiment, the deleted chromosomal region additionally comprises gene RPS4Y2, if present. An overview over the telomeric region of chromosome 8 of the Chinese hamster genome wherein the location of aforementioned genes is shown is provided as FIG. 1. As is shown by the examples, CHO cells comprising a respective deletion in the telomeric region of chromosome 8 (q arm) have particular advantageous properties with respect to expression yield and expression stability. In mouse cells the aforementioned genes are located in the telomeric region of chromosome 6. Non-limiting alternative names of the aforementioned individual genes and/or encoded proteins including orthologs and homologs are also indicated in Table 1 above and the respective genes are encompassed by the scope of the terms used above for the individual genes.

According to one embodiment, the deletion of the FAM60A gene is due to a chromosome breakage. A chromosome breakage can be induced e.g. by treating the mammalian cells with a toxic agent that promotes chromosome breakage, such as e.g. MTX, aphidicolin or hygromycin. Other options for inducing chromosome breakages include but are not limited to radiation, irradiation, mutagens, cancerogenic substances and bleomycin. Chromosome breakages may also occur spontaneously during transfection e.g. electroporation. Methods for inducing chromosome breakage are also known to the skilled person and thus, do not need any detailed description here. After inducing chromosome breakage, cells having the desired breakpoint (which results in a deletion of gene FAM60A) can be identified e.g. be analyzing the DNA or by using the method according to the fifth aspect of the present disclosure. For example, the expression profile of the treated cells can be analyzed to determine whether gene FAM60A or genes located centromeric of gene FAM60A are expressed, whether the expression is reduced or whether the genes are not expressed. For example, in case of mouse or hamster cells it can be analysed whether gene FAM60A is expressed and alternatively or in addition thereto, it can be analyzed whether one or more genes selected from the group consisting of Bicd1, C12orf35, methyltransferase-like protein 20, Dennd5b, Caprin2, Ipo8, Tmtc1 or genes that are located telomeric of the aforementioned genes (wherein telomeric in this respect means into the direction of the telomeric end) are expressed by the cell and/or whether the expression is reduced or eliminated. If the induced breakpoint is located centromeric of the respective gene(s) (wherein centromeric in this respect means further into the chromosome and hence further away from the telomeric end), the telomeric end comprising said genes is deleted which eliminates or reduces (if other copies of the gene exist elsewhere that are expressed) their expression. As is evident from FIG. 1, gene FAM60A is located telomeric of the aforementioned genes Caprin2, Ipo8 and Tmtc1, i.e. it is located further into the direction of the telomeric end. Thus, if the aforementioned genes are deleted by a chromosome break, the deleted region also includes gene FAM60A. Thus, the above genes can be validly used as markers in order to basically indirectly determine whether the induced chromosome breakage resulted in a deletion of a chromosome portion that includes gene FAM60A. Furthermore, it was found that even though located telomeric of gene FAM60A, also other genes such as Bicd1 or C12orf35 can be used as marker to determine whether a chromosome breakage was induced which resulted in a deletion of gene FAM60A. It was found in CHO cells that if e.g. gene Bicd1 or gene C12orf35 is deleted because of a chromosome breakage, the deletion usually also includes gene FAM60A. It was confirmed by analyzing the expression characteristics of several hundred clones that the aforementioned genes can be validly used as markers in order to discriminate cell clones with high and stable expression characteristics from cell clones having low and unstable expression characteristics. The relative expression of the aforementioned genes in CHO cells is shown in FIG. 2. As can be seen from FIG. 2, genes Ipo8 (3), FAM60A (5) and C12orf35 (9) are relatively highly expressed in comparison to other genes that are located in the telomeric region of chromosome 8 in normal CHO-K1 cells, which do not comprise a deletion in the telomeric region of chromosome 8. Thus, it is advantageous to include one or more of the aforementioned genes in the analysis, as this simplifies the detection that their expression is eliminated or reduced. Non-limiting alternative names of the aforementioned individual genes and encoded proteins, including homologs and orthologs, are also indicated in Table 1 above and the respective genes are encompassed by the scope of the terms used above for the individual genes.

According to one embodiment, the breakpoint on chromosome 8 is located centromeric of the FAM60A gene, centromeric of the Caprin2 gene, centromeric of the Ipo8 gene or centromeric of gene RPS4Y2. It was found that the breakpoint on chromosome 8 of the hamster genome is often located centromeric of the Ipo8 gene. According to one embodiment, the breakpoint on chromosome 8 is located within the Tmtc1 gene and said gene is not expressed or its expression is low. According to one embodiment, the Ergic2 gene, which is located centromeric of the Tmtc1 gene, is not deleted on chromosome 8. Thus, according to this embodiment, the breakpoint is telomeric of the Ergic 2 gene (wherein telomeric in this respect means downstream into the direction of the telomeric end) and the Ergic 2 gene is present.

According to one embodiment, the genome of the cell is altered so that functional expression of gene FAM60A is reduced or eliminated. Functional expression of FAM60A can be influenced by various means, for example by altering the promoter and/or an enhancer of the FAM60A gene so that less or no transcript is produced, or by gene silencing technologies such as transcriptional or post-transcriptional gene silencing. According to one embodiment, the isolated eukaryotic cell comprises one or more mutations in the promoter region of the FAM60A gene. For example, the promoter region may be altered to provide a less functional or non-functional promoter, the promoter may also be completely eliminated. Alternatively or in addition, it is possible to add a polynucleotide sequence encoding a polypeptide including a stop codon between the promoter and the start codon of the FAM60A gene which leads to the expression of the other polypeptide instead of FAM60A. Respective methods are well-known to the skilled person and thus, do not need any detailed description here.

Reduction of functional gene expression may achieve a level wherein expression is even eliminated. Post-transcriptional gene silencing can be achieved e.g. by antisense molecules or molecules that mediate RNA interference. Non-limiting examples will be briefly described in the following.

Antisense polynucleotides may be designed to specifically bind to RNA, resulting in the formation of RNA-DNA or RNA-RNA hybrids, with an arrest of reverse transcription or messenger RNA translation. Many forms of antisense have been developed and can be broadly categorized into enzyme-dependent antisense or steric blocking antisense. Enzyme-dependent antisense includes forms dependent on RNase H activity to degrade target mRNA, including single-stranded DNA, RNA, and phosphorothioate antisense. Antisense polynucleotides are typically generated within the cell by expression from antisense constructs that contain the antisense strand as the transcribed strand. Trans-cleaving catalytic RNAs (ribozymes) are RNA molecules possessing endoribonuclease activity. Ribozymes may be specifically designed for a particular target and may be engineered to cleave any RNA species site-specifically in the background of cellular RNA. The cleavage event renders the mRNA unstable and prevents protein expression. The genome of the eukaryotic cell can be altered so that a respective antisense molecule is e.g. permanently expressed.

Another suitable option for reducing functional expression of gene FAM60A on a post-transcriptional level is based on RNA interference (RNAi). Methods for silencing genes by RNAi are well known to the skilled person and thus, do not need any detailed description here. Several embodiments and variations of siRNA compounds are known in the prior art and can be used to reduce expression of gene FAM60A. Suitable siRNAs targeting the chosen/identified target sequences of the target genes on the RNA level can be identified by using proper computational methods, applying certain design-algorithms. According to one embodiment, the RNAi inducing compound is expressed by a vector that is stably transfected into the eukaryotic cell and thus is integrated into the genome of the eukaryotic cell. For siRNA, this can be done e.g. by the introduction of a loop between the two strands, thus producing a single transcript, which can be then processed into a functional siRNA in the eukaryotic cell. Such transcription cassettes typically use an RNA polymerase III promoter (for example U6 or H1) which usually direct the transcription of small nuclear RNAs (shRNAs). It is assumed that the resulting shRNA transcript from the vector is then processed by dicer, thereby producing the double-stranded siRNA molecules, preferably having the characteristic 3' overhangs. According to one embodiment, such shRNA providing vector is stably integrated into the genome of the eukaryotic cell. This embodiment is advantageous, as the downregulation of gene FAM60A is due to the constantly produced siRNA stable and not transient and therefore, is feasible for providing a mammalian host cell with improved expression stability. Cells comprising a respective shRNA providing vector can then be transfected with an expression vector comprising a polynucleotide encoding the product of interest. Alternatively, co-transfection strategies can be used, wherein the vector generating the shRNA is co-transfected with the expression vector comprising the polynucleotide encoding the product of interest.

Transcriptional gene silencing may e.g. include epigenetic modifications. According to one embodiment, functional expression of gene FAM60A is reduced by epigenetic silencing. Furthermore, the sequence of the gene FAM60A can be changed to reduce the half-life of the FAM60A mRNA. Thereby, less FAM60A protein is obtained which also achieves a reduction in the effect of the FAM60A protein in the cell.

According to one embodiment, functional expression of gene FAM60A is reduced or eliminated by targeting a regulatory element involved in the regulation of expression of the FAM60A gene. E.g. a transcription factor, promoter (see also above), enhancer, UTRs, or other regulatory elements can be targeted e.g. by knock-out, deletion, downregulation or any other alteration that inactivates or reduces the activity of said regulatory element, thereby preventing or reducing functional expression of gene FAM60A and thereby impairing the effect of endogenous FAM60A in said cell.

According to one embodiment, the genome of the eukaryotic cell is altered to impair the effect of FAM60A by heterologous expression of a mutant FAM60A which is non- or less functional than the endogenously expressed FAM60A protein. In this embodiment, the isolated eukaryotic cell comprises in addition to the heterologous polynucleotide encoding the polypeptide of interest a further heterologous polynucleotide encoding the mutant FAM60A. By overexpressing a respective non- or less functional mutant FAM60A, a dominant negative phenotype can be created. A further option to impair and hence reduce the effect of FAM60A in the cell is the heterologous expression of a protein such as an antibody which neutralizes FAM60A and hence impairs the effect of FAM60A in the cell. According to one embodiment, the effect of FAM60A is impaired in the cell by reducing or eliminating functional expression of molecules that functionally interact with FAM60A, e.g. by reducing or eliminating functional expression of one or more members of the SIN3/HDAC complex. Such embodiments also impair the effect of FAM60A, because one or more interaction partners of FAM60A that are required so that FAM60A can exert its biological effect, are not present in a functional form because their functional expression was reduced or eliminated.

According to one embodiment, expression of gene FAM60A is reduced by at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold, at least 100 fold or at least 125 fold, at least 250 fold, at least 500 fold, at least 750 fold, at least 1000 fold, at least 1250 fold, at least 1500 fold, at least 1750 fold, at least 2000 fold, at least 2500 fold, at least 3000 fold or at least 3500 fold. Expression can be determined e.g. by using real-time RT-PCR or other sensitive RNA detection methods. Such reduction can be achieved e.g. in comparison with the unmodified reference cell wherein the expression of endogenous gene FAM60A is not reduced. According to one embodiment, expression of gene FAM60A is 0.05% or less, 0.04% or less, 0.03% or less, 0.02% or less, 0.01% or less, 0.005% or less or 0.0025% or less compared to the expression of the 18S RNA (set as 100%) in the same cell. According to one embodiment, expression of gene FAM60A is even less, such as 0.001% or less, 0.0005% or less or even 0.0002 or less compared to the expression of the 18S RNA (set as 100%) in the same cell.

According to one embodiment, the isolated eukaryotic cell which preferably is a mammalian cell, originates from a population of eukaryotic cells which are altered so that the effect of protein FAM60A is impaired in said cells and wherein said cells comprise stably integrated into their genome a heterologous polynucleotide encoding a product of interest, wherein on average at least 40%, at least 50%, at least 60%, at least 70%, at least 75%, at least 80%, at least 85% or at least 90% of the cells originating from said population do not lose more than 30%, preferably not more than 25%, of their product of interest expression titer over a time period of at least 8 weeks, preferably 10 weeks, more preferably over a time period of 12 weeks. As is shown in the examples, after transfection and identification of stably transfected cells, the amount of cells which do not show a gradual loss in productivity during prolonged culturing is increased when using the altered cells described herein, i.e. more stable cell clones are obtained from a selected cell population. The stability property can be tested by cultivating individual cells from said population as cell clones and determining the titer over the indicated time period. The stability can be tested using e.g. the assays described in the examples. As explained above, the stability rates can vary from project to project depending on the expressed protein and whether it is e.g. codon-optimized. However, with the altered eukaryotic cells according to the present disclosure, in all projects analyzed, a significant increase in stably expressing clones was observed compared to the unmodified wildtype cells. The percentage of cell clones that stably express the product of interest was in certain projects 80% or even higher in the analyzed clones during prolonged culturing for time spans in the range of 8 to 12 weeks. Therefore, the abundance of cells with stable expression characteristics was significantly increased in the population of successfully transfected host cells. Therefore, the risk that an instable clone which gradually loses productivity during prolonged culturing is chosen for large scale production is significantly reduced with the teachings of the present disclosure. This important advantage allows to significantly reduce or even completely skip long term stability analyses in order to eliminate instable clones.

According to one embodiment, additionally the effect of the expression product of one or more genes selected from the group consisting of Bicd1, C12orf35, Amn1, methyltransferase-like protein 20, Dennd5b, Fam60a, Caprin2, Ipo8, RPS4Y2 and Tmtc1 or one or more genes located telomeric of the aforementioned genes is impaired. Non-limiting alternative names of the aforementioned individual genes and/or the encoded proteins, including homologs and orthologs, are also indicated in Table 1 above and the respective genes encoding the respective proteins are encompassed by the scope of the terms used above for the individual genes or proteins encoded by said genes. Impairment of the effect can likewise be achieved e.g. by reducing or eliminating the functional expression of the respective genes. Suitable technologies and embodiments are described above in conjunction with the FAM60A gene and likewise apply for any other target gene. As described above, said genes are located in the telomeric region of chromosome 8 of Chinese hamster and chromosome 6 of mouse. If a portion of said telomeric region is deleted, e.g. by inducing a chromosome breakage as described above, the deleted region usually comprises one or more of the aforementioned genes.

According to a preferred embodiment, in said cell wherein the effect of protein FAM60A is impaired, additionally the effect of the expression product of gene C12orf35 is impaired in said cell, preferably by reducing or eliminating functional expression of gene C12orf35. A further unexpected finding was that impairing the effect of the expression product of gene C12orf35 in a eukaryotic cell, for example by reducing or eliminating functional expression of said endogenous gene, results in a significantly increase in the expression of the recombinant product of interest. Thus, a further key gene was identified that influences recombinant expression. Impairing the effect of the expression product of gene C12orf35 in a eukaryotic cell significantly increases the expression yield as is evidenced by the examples. Therefore, impairing the effect of FAM60A and C12orf35 is particularly advantageous, because host cells are provided which show improved characteristics with respect to expression stability and yield and hence, show particularly advantageous properties for the production of a recombinant product of interest. As described, the host cells are preferably mammalian cells.

The C12orf35 gene is endogenously expressed in eukaryotic cells such as e.g. mammalian species such as human, mouse and hamster. The expression product of the C12orf35 gene is a rather large protein. The sequence listing shows exemplary amino acid sequences or putative amino acid sequences of the protein encoded by the endogenous C12orf35 gene of different mammalian species such as hamster (SEQ ID NO: 10 and 11), human (SEQ ID NO: 12 and 13), mouse (SEQ ID NO: 14), cattle (SEQ ID NO: 15) and wild boar (SEQ ID NO: 16). The CDS (Coding DNA Sequence) of C12orf35 from Chinese hamster is shown as SEQ ID NO: 17. Furthermore, a section of the 5'UTR (see SEQ ID NO: 18) and of the 3'UTR (see SEQ ID NO: 19) of the C12orf35 mRNA from Chinese hamster was sequenced. Gene C12orf35 is also referred to as C12orf35 like or C12orf35 homolog in hamster or 2810474O19Rik in mouse. Information about the gene, the coding sequence and the predicted C12orf35 protein is also disclosed for *Cricetulus griseus* in NCBI: XM_003512865, herein incorporated by reference. In human, it also referred to as KIAA1551. Different names can be assigned in different species for the protein or the gene and non-limiting alternative names (aliases) are also listed above in Table 1. Accordingly, the term "C12orf35 gene" as used herein in particular encompasses any endogenous gene which encodes a protein that shares at least 50%, at least 60%, at least 70%, at least 75%, at least 80%, at least 85%, at least 90%, at least 95%, at least 96%, at least 97%, at least 98% or at least 99% homology or identity to one or more of the amino acid sequences shown in SEQ ID NO: 10 to 16 or the protein encoded by SEQ ID NO 17. The protein encoded by such gene preferably has the same function as the protein having an amino acid sequence as is shown in SEQ ID NO: 10 or one or more of SEQ ID NO: 11 to 16 or the protein encoded by SEQ ID NO: 17. Said gene can be modified as described herein in order to impair the function of the expression product that is expressed by the unmodified cell. The protein expressed by gene C12orf35 has not been described in detail in the literature. The terms "C12orf35 protein" or "expression product of endogenous C12orf35 gene" and similar expressions as used herein in particular encompass any protein that shares at least 50%, at least 60%, at least 70%, at least 75%, at least 80%, at least 85%, at least 90%, at least 95%, at least 96%, at least 97%, at least 98% or at least 99% homology or identity to one or more of the amino acid sequences shown in SEQ ID NO: 10 to 16 or the protein encoded by SEQ ID NO 17. Homology, respectively identity may be calculated over the entire length of the reference protein. According to one embodiment, expression of gene C12orf35 is reduced by at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold, at least 100 fold or at least 125 fold, at least 250 fold, at least 500 fold, at least 750 fold, at least 1000 fold, at least 1250 fold, at least 1500 fold, at least 1750 fold or at least 2000 fold. This can be determined e.g. by using real-time RT-PCR or other sensitive RNA detection methods. Such reduction can be achieved e.g. in comparison with the unmodified reference cell wherein the expression of endogenous gene C12orf35 is not reduced. According to one embodiment, expression of gene C12orf35 is 0.05% or less, 0.0475% or less, 0.045% or less, 0.0425% or less, 0.04% or less, 0.0375% or less, 0.035% or less, 0.0325% or less, 0.03% or less, 0.0275% or less, 0.025% or less, 0.0225% or less, 0.02% or less, 0.0175% or less, 0.015% or less compared to the expression of the 18S RNA (set as 100%) in the same cell. According to one embodiment, expression of gene C12orf35 is even less such as 0.001% or less, 0.0001% or less or even 0.00001% or less compared to the expression of the 18S RNA (set as 100%) in the same cell. The functional expression of gene C12orf35 is reduced such that it results in an increase in the expression of a recombinant product of interest if said modified eukaryotic cell is transfected with an expression vector encoding the product of interest compared to a corresponding cell wherein the functional expression of gene C12orf35 is not reduced or eliminated. According to one embodiment, expression of the recombinant product or interest is at least 1.5 times higher, at least 1.75 times higher, at least 2 times higher, at least 2.5 times higher, at least 3 times higher, at least 4 times higher or at least 5 times higher than the expression of a corresponding cell wherein the functional expression of gene C12orf35 is not reduced or eliminated. According embodiments, expression rates are obtained that are at least 8 times higher, at least 10 times higher or at least 15 times higher than the expression of a corresponding cell wherein the expression of gene C12orf35 is not reduced or eliminated. The expression rate of the recombinant product can be tested using e.g. the assays described in the examples.

The eukaryotic cell is derived from a cell type which normally endogenously expresses FAM60A. Examples are described below. As explained above (see also Smith et al, 2012), FAM60A is endogenously expressed in eukaryotic cells such as all metazoas, in particular vertebrates but also invertebrates and in all mammalian cells. The term "isolated" is used to render clear that the eukaryotic cell is not contained in a living organism such as an animal or human. As described herein, the cell can be provided as cell culture, cell line, cell clone and the like. Examples are also described below. As is described above, the eukaryotic cell is altered to impair the effect of FAM60A in said cell, e.g. by reducing or eliminating the effect of FAM60A compared to a corresponding, unmodified eukaryotic cell which endogenously expresses FAM60A. Impairment is preferably achieved by reducing or eliminating functional expression of gene FAM60A in the cell. Non-limiting embodiments are described above. In order to provide production cell lines with uniform and thus predictable stability characteristics, the genome of the eukaryotic cell is altered to achieve that result. Suitable embodiments are described above. The respectively altered eukaryotic cell may then be stably transfected with an expression vector comprising a polynucleotide encoding a product of interest in order to provide eukaryotic cells according to the first aspect which comprises integrated into the genome a heterologous polynucleotide encoding a product of interest. The eukaryotic cell preferably is a vertebrate cell, more preferred a mammalian cell. Thus, all embodiments described herein for eukaryotic cells in general apply to the preferred embodiment wherein mammalian cells are used. The eukaryotic cell may be e.g. selected from the group consisting of rodent cells, human cells and monkey cells. Preferred mammalian cells are rodent cells such as e.g. cells derived from hamster or mouse. They can be selected from the group consisting of a Chinese hamster cell such as a CHO cell, a BHK cell, a NS0 cell, a C127 cell, a mouse 3T3 fibroblast cell, and a SP2/0 cell. Particularly preferred is a CHO cell, e.g. a CHO cell such as CHO-K1, CHO-S, CHO-K1SV, CHO-SSF3, CHO-DG44, CHO-DUXB11, or a cell line derived therefrom. As is shown in the examples, a knock-out of gene FAM60A in a CHO cell provides a population of CHO cells wherein the abundance of stably transfected cells with prolonged stability characteristics is increased. The FAM60A gene is also expressed in human cells. Thus, according to one embodiment, the mammalian cell is derived from a human cell, which may be e.g. selected from the group consisting of a HEK293 cell, a MCF-7 cell, a PerC6 cell, a CAP cell, hematopoietic cells and a HeLa cell. Another alternative are monkey cells, which, e.g. may be selected from the group consisting of a COS cells, COS-1, a COS-7 cell and a Vero cell. According to one embodiment, the eukaryotic cell, which preferably is a mammalian cell, is provided as cell clone or cell line.

A eukaryotic cell wherein the genome is altered so that the effect of FAM60A is impaired in said cell and which does not comprise a heterologous polynucleotide encoding a product of interest, a heterologous polynucleotide encoding a selectable marker and/or a heterologous polynucleotide encoding a reporter polypeptide that is/are expressed, in particular secreted from said cell, can be used as starting material for preparing the eukaryotic cells according to the present disclosure. A respective "empty" altered eukaryotic cell can be used e.g. as cloning cell line for recombinant production technologies. A respective cell can be stably transfected with a heterologous polynucleotide encoding a product of interest, e.g. using an appropriate expression vector. Such "empty" eukaryotic cells in which the effect of FAM60A is impaired and which do not yet express and in particular do not secrete a recombinant product, can thus be transfected with different expression vectors, depending on the desired product of interest that is supposed to be recombinantly produced. Thus, such eukaryotic cell line can be used for different projects, i.e. for the production of different products of interest, in particular different secreted polypeptides of interest.

The eukaryotic cell according to the first aspect comprises a heterologous polynucleotide encoding a product of interest stably integrated into its genome. The product of interest is the recombinant product that is supposed to be expressed by the eukaryotic cell in large quantity. Preferably, the product of interest is a polypeptide. According to a preferred embodiment, the polypeptide of interest is secreted by the cell. The eukaryotic cell may additionally comprise a heterologous polynucleotide encoding a selectable marker and/or a heterologous polynucleotide encoding a reporter. This simplifies the selection of host cells which are successfully transfected and thus express the product of interest. Furthermore, the eukaryotic cell may comprise several polynucleotides encoding different selectable markers and/or reporter polypeptides.

A "heterologous polynucleotide" or "heterologous nucleic acid" and likewise expressions used herein in particular refer to a polynucleotide sequence that has been introduced into the eukaryotic cell e.g. by the use of recombinant techniques such as transfection. A "polynucleotide" in particular refers to a polymer of nucleotides which are usually linked from one deoxyribose or ribose to another and refers to DNA as well as RNA, depending on the context. The term "polynucleotide" does not comprise any size restrictions.

An expression vector can be used to introduce heterologous polynucleotides. The polynucleotides can be comprised in an expression cassette. The polynucleotide(s) encoding the product of interest and the polynucleotide(s) encoding a selectable marker or reporter polypeptide may be located on the same or different expression vectors. Introduction into the eukaryotic cell may be achieved e.g. by transfecting a suitable expression vector comprising the polynucleotide encoding the product of interest into the host cells. The expression vector integrates into the genome of the host cell (stable transfection). As is shown by the examples, the novel eukaryotic cells described herein are advantageous for stable transfection as the number of clones with prolonged stability is increased. Stable transfection is also the standard for generating high expressing cell clones for producing a product of interest such as a polypeptide of interest on industrial scale. This is particularly important for therapeutic or diagnostic polypeptides of interest. Several appropriate methods are known in the prior art for introducing a heterologous nucleic acid such as an expression vector into eukaryotic such as mammalian host cells and thus, do not need any detailed description herein. Respective methods include but are not limited to calcium phosphate transfection, electroporation, lipofection, biolistic- and polymer-mediated genes transfer and the like. Besides traditional random integration based methods also recombination mediated approaches can be used to transfer the heterologous polynucleotide into the host cell genome. As respective methods are well known in the prior art, they do not need any detailed description here. Non-limiting embodiments of suitable vector designs are also described subsequently and it is referred to the respective disclosure.

Expression vectors used to achieve expression of a recombinant product of interest usually contain transcriptional control elements suitable to drive transcription such as e.g. promoters, enhancers, polyadenylation signals, transcription pausing or termination signals usually as element of an expression cassette. If the desired product is a polypeptide, suitable translational control elements are preferably included in the vector, such as e.g. 5' untranslated regions leading to 5' cap structures suitable for recruiting ribosomes and stop codons to terminate the translation process. The resultant transcripts harbour functional translation elements that facilitate protein expression (i.e. translation) and proper translation termination. A functional expression unit, capable of properly driving the expression of an incorporated polynucleotide is also referred to as an "expression cassette". It is well-known to the skilled person how an expression cassette shall be designed in order to allow the expression in a eukaryotic cell, such as preferably in a mammalian cell.

The polynucleotide(s) encoding the product of interest and the polynucleotides encoding the selectable marker(s) and/or reporter polypeptide(s) as described herein are preferably comprised in expression cassettes. Several embodiments are suitable. For example, each of said polynucleotide(s) can be comprised in a separate expression cassette. This is also referred to as monocistronic setting. It is also within the scope of the present invention that at least two of the respective polynucleotides are comprised in one expression cassette. According to one embodiment, at least one internal ribosomal entry site (IRES) element is functionally located between the polynucleotides that are expressed from the same expression cassette. Thereby, it is ensured that separate translation products are obtained from said transcript. Respective IRES based expression technologies and other bi- and polycistronic systems are well known and thus need no further description here.

As described, the expression vector may comprise at least one promoter and/or promoter/enhancer element as element of an expression cassette. Promoters can be divided in two classes, those that function constitutively and those that are regulated by induction or depression. Both are suitable. Strong constitutive promoters which drive expression in many cell types include but are not limited to the adenovirus major late promoter, the human cytomegalovirus immediate early promoter, the SV40 and Rous Sarcoma virus promoter, and the murine 3-phosphoglycerate kinase promoter, EF1a. According to one embodiment, the promoter and/or enhancer is either obtained from CMV and/or SV40. The transcription promoters can be selected from the group consisting of an SV40 promoter, a CMV promoter, an EF1alpha promoter, a RSV promoter, a BROAD3 promoter, a murine rosa 26 promoter, a pCEFL promoter and a β-actin promoter. Also other promoters can be used if they result in expression of the product of interest in the eukaryotic cell which preferably is a mammalian cell.

Furthermore, an expression cassette may comprise at least one intron. Usually, introns are placed at the 5' end of the open reading frame but may also be placed at the 3' end. Said intron may be located between the promoter and or promoter/enhancer element(s) and the 5' end of the open reading frame of the polynucleotide encoding the product of interest to be expressed. Several suitable introns are known in the state of the art that can be used in conjunction with the present disclosure.

The product of interest can be any biological product capable of being produced by transcription, translation or any other event of expression of the genetic information encoded by the polynucleotide encoding the product of interest. The product of interest may be selected from the group consisting of polypeptides and nucleic acids, in particular RNA. The product can be a pharmaceutically or therapeutically active compound, or a research tool to be utilized in assays and the like. Preferably, the product of interest is a polypeptide. Any polypeptide of interest can be expressed with the method of the present invention. The term "polypeptide" refers to a molecule comprising a polymer of amino acids linked together by a peptide bond(s). Polypeptides include polypeptides of any length, including proteins (e.g. having more than 50 amino acids) and peptides (e.g. 2-49 amino acids). Polypeptides include proteins and/or peptides of any activity, function or size, and may include e.g. enzymes (e.g. proteases, kinases, phosphatases), receptors, transporters, bactericidal and/or endotoxin-binding proteins, structural polypeptides, membrane-bound polypeptides, glycoproteins, globular proteins, immune polypeptides, toxins, antibiotics, hormones, growth factors, blood factors, vaccines or the like. The polypeptide may be selected from the group consisting of peptide hormones, interleukins, tissue plasminogen activators, cytokines, immunoglobulins, in particular antibodies or functional antibody fragments or variants thereof and Fc-fusion proteins. The polypeptide of interest that is expressed according to the teachings described herein may also be a subunit or domain of a polypeptide, such as e.g. a heavy chain or a light chain of an antibody or a functional fragment or derivative thereof. The terms "product of interest" or "polypeptide of interest" may refer to such individual subunit or domain or the final protein that is composed of the respective subunits or domains, depending on the context. In a preferred embodiment the polypeptide of interest is an immunoglobulin molecule, more preferably an antibody, or a subunit or domain thereof such as e.g. the heavy or light chain of an antibody. The term "antibody" as used herein particularly refers to a protein comprising at least two heavy chains and two light chains connected by disulfide bonds. The term "antibody" includes naturally occurring antibodies as well as all recombinant forms of antibodies, e.g., humanized antibodies, fully human antibodies and chimeric antibodies. Each heavy chain is usually comprised of a heavy chain variable region (VH) and a heavy chain constant region (CH). Each light chain is usually comprised of a light chain variable region (VL) and a light chain constant region (CL). The term "antibody", however, also includes other types of antibodies such as single domain antibodies, heavy chain antibodies, i.e. antibodies only composed of one or more, in particular two heavy chains, and nanobodies, i.e. antibodies only composed of a single monomeric variable domain. As discussed above, the polynucleotide encoding the polypeptide of interest may also encode one or more subunits or domains of an antibody, e.g. a heavy or a light chain or a functional fragment or derivative thereof, as polypeptide of interest. Said subunits or domains can be expressed either from the same or different expression cassettes. A "functional fragment or derivative" of an antibody in particular refers to a polypeptide which is derived from an antibody and is capable of binding to the same antigen, in particular to the same epitope as the antibody. It has been shown that the antigen-binding function of an antibody can be executed by fragments of a full-length antibody or derivatives thereof. Examples of fragments or derivatives of an antibody include (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. According to one embodiment, the eukaryotic cell secretes the polypeptide of interest into the cell culture medium. According to one embodiment, the polypeptide of interest is not or does not comprise SIN3A. According to one embodiment, the polypeptide of interest is not or does not comprise FAM60A.

The eukaryotic cell may or may not comprise an endogenous polynucleotide corresponding to, respectively being identical to the polynucleotide encoding the product of interest. According to one embodiment, the eukaryotic cell does not comprise an endogenous gene corresponding to the product of interest.

As described, in embodiments, the eukaryotic cell comprises at least one heterologous polynucleotide encoding a selectable marker and/or a heterologous polynucleotide encoding a reporter polypeptide in addition to the heterologous polynucleotide encoding the product of interest.

A "selectable marker" allows under appropriate selective culture conditions the selection of host cells expressing said selectable marker. A selectable marker provides the carrier of said marker under selective conditions with a survival and/or growth advantage. Thereby, host cells successfully transfected with the expression vector can be selected under appropriate selection conditions. Typically, a selectable marker gene will confer resistance to a selection agent such as a drug, e.g. an antibiotic or other toxic agent, or compensate for a metabolic or catabolic defect in the host cell. It may be a positive or negative selection marker. For selecting successfully transfected host cells a culture medium may be used for culturing the host cells comprises a selection agent that allows selection for the selectable marker used. In other embodiments, the selection marker enables the host cell to survive and proliferate in the absence or reduction of a compound which is essential for survival and/or proliferation of the host cells lacking the selection marker. By cultivating the host cells in a medium which does not comprise the essential compound in a concentration high enough for survival and/or proliferation of the host cell or comprises a reduced amount of said essential compound, only host cells expressing the selection marker can survive and/or proliferate. According to one embodiment, the selectable marker is a drug resistance marker encoding a protein that confers resistance to selection conditions involving said drug. A variety of selectable marker genes have been described (see, e.g., WO 92/08796, WO 94/28143, WO2004/081167, WO2009/080759, WO2010/097240). E.g. at least one selectable marker may be used which confers resistance against one or more antibiotic agents. The selectable marker may according to one embodiment be an amplifiable selectable marker. An amplifiable selectable marker allows the selection of vector containing host cells and may promote gene amplification of said vector in the host cells. Selectable marker genes commonly used with eukaryotic cells such as in particular mammalian cells include the genes for aminoglycoside phosphotransferase (APH), hygromycin phosphotransferase (hyg), dihydrofolate reductase (DHFR), thymidine kinase (tk), glutamine synthetase, asparagine synthetase, and genes encoding resistance to neomycin (G418), puromycin, hygromycin, zeocin, ouabain, blasticidin, histidinol D, bleomycin, phleomycin and mycophenolic acid. According to one embodiment, a folate receptor is used as selectable marker in conjunction with the novel eukaryotic cells described herein (see e.g. WO2009/080759), which preferably are mammalian cells. According to one embodiment, the eukaryotic cell which is dependent on folate uptake comprises a heterologous polynucleotide encoding a folate receptor as selectable marker and/or comprises a heterologous polynucleotide encoding a dihydrofolate reductase (DHFR) as selectable marker. This embodiment will also be described in detail below in conjunction with the selection method according to the second aspect. The eukaryotic cell may express endogenously DHFR and a folate receptor.

A "reporter polypeptide" allows the identification of a cell expressing said reporter polypeptide based on the reporting characteristics (e.g. fluorescence). Reporter genes usually do not provide the host cells with a survival advantage. However, the expression of the reporter polypeptide can be used to differentiate between cells expressing the reporter polypeptide and those cells which do not. Therefore, also a reporter gene enables the selection of successfully transfected host cells. Suitable reporter polypeptides include but are not limited to as e.g. green fluorescence protein (GFP), YFP, CFP and luciferase. According to one embodiment, the reporter polypeptide has characteristics that enable the selection by flow cytometry.

As described, the expression vector comprising the polynucleotide encoding the product of interest may also comprise more than one selectable marker and/or reporter gene. Furthermore, the one or more polynucleotides encoding the selectable marker(s) and/or the one or more polynucleotides encoding the reporter polypeptide(s) may also be provided on one or more different expression vectors which are co-transfected with the expression vector which comprises the polynucleotide encoding the product of interest. Such co-transfection strategies likewise enable selection as is well-known in the prior art.

The expression vector or the combination of at least two expression vectors comprised in the eukaryotic cell may additionally comprise further vector elements. E.g. at least one additional polynucleotide encoding a further product of interest can be comprised. As explained above and as becomes apparent from the above described examples of polypeptides that can be expressed according to the present teachings, the final polypeptide that is to be produced and preferably secreted by the host cell can also be a protein that is composed of several individual subunits or domains. A preferred example of a respective protein is an immunoglobulin molecule, in particular an antibody that comprises e.g. heavy and light chains. There are several options for producing a respective protein that is composed of different individual subunits or domains and appropriate vector designs are known in the art. According to one embodiment, two or more subunits or domains of said protein are expressed from one expression cassette. In this embodiment, one long transcript is obtained from the respective expression cassette that comprises the coding regions of the individual subunits or domains of the protein. According to one embodiment, at least one IRES element (internal ribosomal entry site) is functionally located between the coding regions of the individual subunits or domains and each coding region is preceded by a secretory leader sequence. Thereby, it is ensured that separate translation products are obtained from said transcript and that the final protein can be correctly assembled and secreted. Respective technologies are known in the prior art and thus, do not need any detailed description herein.

For some embodiments such as the expression of antibodies it is even preferred to express the individual subunits or domains from different expression cassettes. According to one embodiment, the expression cassette used for expressing the product of interest is a monocistronic expression cassette. All expression cassettes comprised in the expression vector or combination of expression vectors may be monocistronic. According to one embodiment, accordingly, each expression cassette designed for expressing a product of interest comprises a polynucleotide encoding one subunit or domain of the protein to be expressed as polypeptide of interest. E.g. in case of antibodies, one expression cassette may encode the light chain of an antibody and another expression cassette may encode the heavy chain of the antibody. After expression of the individual subunits or domains from the individual expression cassettes, the final protein such as an antibody is assembled from said subunits or domains and secreted by the host cell. This embodiment is particularly suitable for expressing immunoglobulin molecules such as antibodies. In this case, a first heterologous polynucleotide encoding a product of interest encodes e.g. the heavy or the light chain of an immunoglobulin molecule and a second heterologous polynucleotide encoding a product of interest encodes the other chain of the immunoglobulin molecule. According to one embodiment, the expression vector or combination of at least two expression vectors used for transfecting the mammalian host cell comprises at least one expression cassette comprising a polynucleotide encoding the heavy chain of an immunoglobulin molecule or a functional fragment thereof and at least one expression cassette comprising a polynucleotide encoding the light chain of an immunoglobulin molecule or a functional fragment thereof. Said polynucleotides may be located on the same or on different expression vectors in case a combination of at least two expression vectors is used. Upon expression of said polynucleotides in the transfected host cell, a functional immunoglobulin molecule is obtained and preferably is secreted from the host cell. As is shown by the examples, using the novel cells and cell lines described herein wherein the genome of the host cell is altered so that the effect of FAM60A is impaired in said cell, preferably by reducing or eliminating functional expression of said gene, are particularly suitable for expressing proteins due to their improved stability characteristics. Furthermore, in embodiments, in particular wherein the effect of the expression product of gene C12orf35 is additionally impaired, the expression yield also increases significantly. Therefore, the novel eukaryotic cell lines described herein have particular advantages when being used for recombinant expression of polypeptides, including proteins that are composed of several subunits of domains such as e.g. antibodies. Further advantages are also described in conjunction with the examples.

B. Selection Method

According to a second aspect, a method for selecting a host cell which recombinantly expresses a product of interest is provided, comprising (a) providing eukaryotic cells according to the first aspect as host cells; and (b) selecting one or more host cells expressing the product of interest.

The eukaryotic host cells according to the first aspect, including suitable and preferred embodiments, as well as their advantages are described in detail above and it is referred to the respective disclosure which also applies here. As described, vertebrate cells, in particular mammalian cells, are preferably used as host cells. The advantageous properties of said eukaryotic cells simplify e.g. the selection and thus identification of suitable production clones. Furthermore, as the proportion of cells with favourable stability characteristics in the transfected cell population is significantly increased when using the eukaryotic cells described herein, less clones need to be analysed and screened for their production characteristics in order to identify suitable stable production clones. This saves time and furthermore, allows handling more projects in parallel. Furthermore, as is demonstrated by the examples, in embodiments, the number respectively proportion of high expressing cells with favourable characteristics is increased after stable transfection and selection steps. Such expressing cells, also called cell pools, produce significant quantities of the product of interest. Thus, such cell pools comprising high expressing cells can be e.g. used in order to produce a polypeptide of interest within a short timeframe. Therefore, the product of interest can be produced rapidly in respective cells.

According to one embodiment, stage (a) of the selection method according to the second aspect comprises transfecting eukaryotic cells wherein the genome of said cells is altered so that the effect of protein FAM60A is impaired in said cells with a heterologous polynucleotide encoding the product of interest, thereby providing respective eukaryotic cells which comprise a heterologous polynucleotide encoding the product of interest stably integrated into the genome. As described, mammalian cells are preferably used as eukaryotic host cells. The polynucleotide encoding the product of interest may be comprised in an expression vector that is then transfected into the eukaryotic cell.

Selection stage (b) may be a multi-step selection process comprising several selection steps in order to select and thus identify host cells that express a product of interest with high yield. For example, stage (b) may include one or more selection steps to identify cells that were successfully transfected as well as one or more subsequent selection steps to select high expressing cells from the pool of successfully transfected cells. The appropriate selection strategy depends on the design of the expression vector that is used for introducing the polynucleotide encoding the product of interest and in particular depends on the used selection marker(s) and/or reporter(s). Non-limiting embodiments will be described in the following.

As described above, the eukaryotic host cells may comprise at least one heterologous polynucleotide encoding a selectable marker. The polynucleotide encoding the selectable marker can be introduced into the host cell together with the polynucleotide encoding the product of interest using either the same or a different co-transfected expression vector. Stage (b) then comprises culturing said plurality of host cells under conditions providing a selection pressure to the host cells to identify successfully transfected host cells, e.g. using an appropriate selection medium. As used herein, a "selection medium" in particular refers to a cell culture medium useful for the selection of host cells that express the selectable marker. It may include e.g. a selection agent such as a toxic drug which allows to identify successfully transfected host cells. Alternatively, an essential compound can be absent or its concentration can be reduced in the selection medium. According to one embodiment, host cells which were not successfully transfected and hence, do not express the selection marker(s) or wherein expression is low cannot proliferate or die under the selective cultivation conditions. In contrast, host cells which were successfully transfected with the expression vector(s) and which express the selection marker(s) (and accordingly the co-introduced product of interest) with sufficient yield are resistant to or are less affected by the selection pressure and therefore, can proliferate, thereby outgrowing the host cells which were not successfully transfected or wherein the integration site into the genome of the cell is not favourable. According to one embodiment, the selectable marker is selected from the group consisting of antibiotic resistance markers, drug resistance markers and metabolic markers. Suitable examples for selectable markers and selection principles are described above in conjunction with the first aspect and appropriate selection conditions for the individual selectable markers are also well-known to the skilled person. Non-limiting but advantageous embodiments will be described briefly subsequently.

As is shown by the examples, one advantage of the novel eukaryotic cells described herein, such as in particular a CHO cell line comprising a deletion in the telomeric region of chromosome 8 which includes gene FAM60A and therefore also gene C12orf35, is that already after one standard selection step, such as e.g. a G418/neo selection, the percentage of high-producing cells with stable characteristics is significantly increased. For example, when transfecting normal CHO cell lines, which are not respectively altered, often 60% or even up to 80% of the cells surviving G418/neo selection are non-producers. The number of non- or low producers is significantly reduced when using the novel cell lines according to the present disclosure. This allows to efficiently perform the selection in stage (b) by using only one selectable marker and thus only one selection step, such as for example a G418/neo selection, if desired. This increases the speed of selection and accordingly, reduces the time required for obtaining stably transfected cells that express the product of interest. Furthermore, because the number of high and stable producers is increased, it was found that even in the absence of a specific selection for high producing cells, cell populations can be generated with clone like performance and thus, within very short time. Therefore, the product of interest can even be manufactured from such pools. Thus, for applications wherein e.g. only certain amounts of protein are needed quickly, for example for research or testing purposes, such a rapid selection system which quickly renders good producing cells or producing cell pools is highly advantageous.

However, if it is desired to further increase the productivity, a multi-step selection in stage (b) is preferred. This is particularly the case when intending to establish a clonal cell line for producing the product of interest on large scale, in particular industrial scale.

As described above, the expression vector or expression vectors introduced into the cells described herein may comprise two or more selectable marker genes and selection for the different selectable markers may be done simultaneously or sequentially for selecting host cells which were successfully transfected with the expression vector(s) and express the product of interest with high yield. The selection medium used for cultivation may comprise selection agents for all selectable markers used. In another embodiment, cultivation can be performed first with a selection medium only comprising the selection agent(s) of one or a subset of the selectable marker genes used, followed by the addition of one or more of the selection agents for the remaining selectable marker genes. In another embodiment, the host cells are cultivated with a first selection medium only comprising the selection agent(s) of one or a subset of the selectable marker genes of the vector(s), followed by cultivation with a second selection medium comprising the selection agent(s) of one or more of the selection agents of the remaining selectable marker genes. According to one embodiment, the second selection medium does not comprise the selection agent(s) used in the first selection medium.

According to one embodiment, the eukaryotic cells provided in stage (a) comprise a heterologous polynucleotide encoding a dihydrofolate reductase (DHFR) as selectable marker and stage (b) comprises performing a selection step for DHFR. A respective selection step usually involves a selection medium comprising a DHFR inhibitor. Several suitable DHFR enzymes and accordingly DHFR genes are known in the prior art that can be used as selectable marker. The term DHFR refers to wild type DHFR as well as to DHFR enzymes having one or more amino acid sequence exchanges (e.g. deletions, substitutions or additions) with respect to the amino acid sequence of the corresponding wildtype DHFR enzyme, fusion proteins comprising a DHFR enzyme and DHFR enzymes which have been modified to provide an additional structure and/or function, as well as functional fragments of the foregoing, which still have at least one function of a DHFR enzyme. Such embodiments are well-known in the prior art and thus, do not need to be described in detail. For example, a DHFR enzyme may be used as selectable marker that is more or less sensitive to antifolates such as MTX than the wild type DHFR enzyme and/or the DHFR enzyme endogenously expressed by the host cell if expressed. Respective DHFR enzymes are well-known in the prior art and e.g. are described in EP 0 246 049 and other documents. The DHFR enzyme can be derived from any species as long as it will be functional within the present invention, i.e. compatible with the mammalian host cell utilised. E.g. a mutant mouse DHFR with a major resistance to MTX has been extensively used as a dominant selectable marker in eukaryotic cells. A DHFR enzyme may be used as selectable marker which is less susceptible to a DHFR inhibitor such as MTX than the DHFR enzyme endogenously expressed in a DHFR$^+$ (plus) host cell and thus a host cell which comprises a functional endogenous DHFR gene. According to one embodiment, an intron or a fragment thereof is placed at the 3' end of the open reading frame of the DHFR gene. The intron used in the DHFR expression cassette is leading to a smaller, non-functional variant of the DHFR gene (Grillari et al., 2001, J. Biotechnol. 87, 59-65). Thereby, the expression level of the DHFR gene is lowered which further increases the stringency of selection. Alternative methods making use of an intron to reduce the expression level of the DHFR gene are described in EP0 724 639 and could also be used.

A "DHFR inhibitor" in particular refers to a compound which inhibits the activity of dihydrofolate reductase (DHFR). A respective inhibitor may for example compete with the DHFR substrate for binding to DHFR. Suitable DHFR inhibitors are for example antifolates such as methotrexate (MTX). Thus, according to one embodiment, stage (b) comprises performing a selection step for DHFR by cultivating said plurality of host cells in a selective culture medium which comprises at least one DHFR inhibitor, such as preferably an antifolate. Respective selection conditions are known to the skilled person. According to one embodiment, a selective culture medium is used in stage (b) which comprises an antifolate in a concentration of 1500 nM or less, 1250 nM or less, 1000 nM or less, 750 nM or less, 500 nM or less, 250 nM or less, 200 nM or less, 150 nM or less, 125 nM or less, 100 nM or less or 75 nM or less. The used concentration of said inhibitor in the selective culture medium (which may also be increased gradually), determines the stringency of the selection conditions. Preferred concentration ranges for the antifolate may be selected from 500 nM-0.1 nM, 350 nM-1 nM, 200 nM-2.5 nM, 150 nM-5 nM, 100 nM-7.5 nM and 75 nM-10 nM. According to one embodiment, the selective culture medium comprises MTX as antifolate. Low MTX concentrations can be used in conjunction with the novel eukaryotic cells described herein for performing a DHFR selection, in particular if selection is performed in combination with a limiting concentration of folate.

According to one embodiment, the host cells according to the present disclosure provided in stage (a) comprise a heterologous polynucleotide encoding a folate transporter as selectable marker. A folate transporter based selection system has several advantages when being used in conjunction with eukaryotic cells that are dependent on folate uptake such as mammalian cells. A folate transporter allows to import at least one folate from the culture medium into the host cell which preferably is a mammalian cell. According to one embodiment, the folate transporter is or comprises the reduced folate carrier (RFC). RFC is a ubiquitously expressed membrane glycoprotein that serves as the major transporter for the uptake of reduced folates such as 5-methyl-THF and 5-formyl-THF into the cell. However, RFC displays a very poor affinity for the oxidized folate, folic acid. Hence, cells that lack the expression of RFC or have been deleted from the genomic RFC locus can serve as recipients for the transfection of the selectable marker gene RFC under conditions in which reduced folates such as 5-formyl-THF are gradually deprived from the growth medium, thereby allowing to identify cells that express increased levels of the this folate transporter and accordingly the product of interest. Suitable selection conditions when using RFC as selectable marker are known to the skilled person and are e.g. described in WO2006/059323.

According to one embodiment which is also described in detail below and in the example section, the folate transporter used as selectable marker is a folate receptor. A folate receptor based selection system has several advantages. For example for selection, no toxic substances are needed (even though they can be used) and furthermore, the endogenous folate receptor of the host cell does not need to be knocked out. Furthermore, this expression system works particularly well in conjunction with the novel cells described herein, which preferably are mammalian cells.

A "folate receptor" as used herein refers to a folate receptor that is functional and thus capable of import or uptake of a folate or derivative thereof into the eukaryotic cell. Preferably, the receptor is capable of unidirectional import or uptake of folate or a derivative of folate into the eukaryotic cell. Furthermore, a folate receptor as used herein is membrane-bound. Thus, the folate receptors described herein are functional membrane-bound folate receptors. Membrane anchorage can be achieved e.g. by a transmembrane anchor or by a GPI anchor. A GPI anchor is preferred as it corresponds to the natural setting of membrane-bound folate receptor. Folate receptors (FRs) are high-affinity folate-binding glycoproteins. They are encoded by three distinct genes FR alpha, FR beta and FR gamma. FR alpha and FR beta are glycosylphosphatidylinositol (GPI)-anchored, cell surface glycoproteins, whereas FR gamma is devoid of a GPI anchor and is a secreted protein. However, it can be genetically altered to include a transmembrane anchor or a GPI anchor. Such an altered form of a FR gamma that includes a membrane anchor is also considered a membrane-bound folate receptor if it is capable of import or uptake of a folate or derivative thereof into a eukaryotic cell. The term "folate receptor" also includes membrane-bound mutants of wildtype folate receptors that are capable of folate uptake and fusion proteins comprising a respective folate receptor.

The folate receptor utilized can be derived from a folate receptor of any species as long as it will be functional within the present invention, i.e. it is compatible with the host cell that is utilized and when being expressed in the transfected host cell, incorporates folate, in particular folic acid, from the culture medium into the host cell that is dependent on folate uptake. In general, the folate receptor that is introduced into the host cell as selectable marker can be homologous or heterologous to an endogenous folate receptor of the host cell (if an endogenous folate receptor is present what is preferred). If it is homologous, it will be derived from the same species as the host cell which preferably is a mammalian host cell. If it is heterologous, it will be derived from another species than the host cell. For example a human folate receptor may be used as selectable marker for a rodent host cell, e.g. a hamster cell such as a CHO cell. Preferably, a folate receptor derived from a mammalian species is used, for example derived from a rodent, such as mouse, rat or hamster, or, more preferred, derived from a human. The membrane-bound folate receptor used as selectable marker can be selected from the group consisting of a folate receptor alpha, a folate receptor beta and a folate receptor gamma. According to one embodiment, a human folate receptor alpha is used as selectable marker.

The use of a membrane-bound folate receptor as folate transporter is advantageous because cells can be used, which endogenously express their own folate receptors and folic acid can be processed by the folate receptor. Suitable membrane-bound folate receptors that can be used as selectable markers for eukaryotic cells that are dependent on folate uptake such as mammalian cells and suitable selection conditions are also described in WO 2009/080759, herein incorporated by reference. According to one embodiment, the mature wild type human folate receptor alpha is used which comprises the following amino acid sequence shown in SEQ ID NO: 20 (1-letter code, shown in direction from N-terminus to C-terminus).

Folate receptor alpha is naturally anchored to the cell membrane by a GPI anchor. The signal sequence for a GPI anchor is not shown in SEQ ID NO: 20. According to one embodiment, the folate receptor alpha which is derived from or comprises SEQ ID NO: 20 comprises a GPI anchor signal at the C-terminus. Any suitable GPI anchor signal may be used. The natural GPI anchor signal sequence of human folate receptor alpha is shown in SEQ ID NO: 21 (1-letter code, shown in direction from N-terminus to C-terminus).

Membrane anchorage may alternatively be achieved by using a membrane anchor, e.g. a transmembrane anchor. In this embodiment, the folate receptor comprises a membrane anchor at its C-terminus. Suitable anchors are known in the prior art. The folate receptor alpha which is derived from or comprises SEQ ID NO: 20 may comprise a leader sequence at the N-terminus. Any suitable leader sequence can be used which ensures functional expression of the folate receptor.

The full amino acid sequence including the natural leader sequence (at the N-terminus) and the natural GPI anchor signal sequence (at the C-terminus) of the wild type human folate receptor alpha is shown in SEQ ID NO: 22 (1-letter code, shown in direction from N-terminus to C-terminus).

According to one embodiment, the membrane-bound folate receptor has or comprises the amino acid sequence of SEQ ID NO: 20, or 22 or is a functional variant of the foregoing which has at least 80%, at least 85%, at least 90%, at least 95%, at least 98% or at least 99% homology or identity to SEQ ID NO: 20 or 22, is membrane-bound and is capable of folic acid uptake into the cell.

When using a eukaryotic cell that is dependent on folate uptake such as a mammalian host cell, which comprises a heterologous polynucleotide encoding a folate transporter, preferably a folate receptor, stage (b) comprises a selection step wherein said plurality of host cells are cultured in a selective culture medium comprising folate in a limiting concentration. A "limiting concentration of folate" as used herein in particular refers to a concentration of folate(s) in the selective culture medium which provides a selective pressure on the host cell. Under such selection conditions, only host cells grow and proliferate that have incorporated the expression vector and thus, express the folate transporter as selectable marker. Accordingly, folates are not comprised in the selective culture medium in affluence, and this limitation of folate(s) in the culture medium provides a selection pressure on the host cells. The folate comprised in the selective culture medium in a limiting concentration is capable of being taken up into and being processed by the host cell, in particular by host cells that have incorporated the folate transporter that is used as selectable marker. Folates and in particular derivatives of folate which would not or cannot be processed by the host cell do not contribute to the selection pressure that is exerted to select host cells that have incorporated the folate transporter as selectable marker and accordingly do not contribute to the limiting concentration of folate. However, respective folates, such as e.g. antifolates, may be present and even preferably are present, if a combined selection with DHFR is performed as will be described subsequently. The folate present in the selective culture medium in a limiting concentration can e.g. be an oxidized folate or a reduced folate or a derivative thereof. Oxidized folates, such as folic acid, as well as reduced derivatives of folic acid, known as reduced folates or tetrahydrofolates (THF), are a group of B-9 vitamins that are essential cofactors and/or coenzymes for the biosynthesis of purines, thymidylate and certain amino acids in eukaryotic cells that are dependent on folate uptake such as mammalian cells. THF cofactors are particularly crucial for DNA replication and hence cellular proliferation. Preferably, the folate that is comprised in a limiting concentration in the selective culture medium is folic acid. Suitable concentration ranges for providing a limiting concentration of folate are described below.

The folate transporter based selection system is based on the limited availability of folate, preferably folic acid, in the cell culture medium. Host cells that have not successfully incorporated the expression vector(s) and hence do not express sufficient quantities of the folate transporter, which preferably is a folate receptor, die or are impaired in growth under the selective culture conditions compared to host cells that have successfully incorporated the expression vector(s). As is shown by the examples, using a folate receptor based selection in combination with the novel cells described herein allows an accelerated selection, screening and establishment of cell clones that stably overexpress high levels of recombinant products of interest such as polypeptides.

The selective culture medium that is used in stage (b), respectively used in a sub-step of stage (b), for selection against a folate receptor as selectable marker may comprise folate and in particular folic acid in a concentration selected from:
  (a) about 5000 nM-0.1 nM;
  (b) about 2500 nM-0.1 nM;
  (c) about 1500 nM-0.1 nM;
  (d) about 1000 nM-0.1 nM;
  (e) about 750 nM-0.1 nM;
  (f) about 500 nM-0.1 nM;
  (g) about 250 nM-0.2 nM; preferably about 250 nM-1 nM or about 250 nM-2.5 nM;
  (h) about 150 nM-0.3 nM; preferably about 150 nM-1 nM or about 150 nM-2.5 nM;
  (i) about 100 nM-0.5 nM; preferably about 100 nM-1 nM or about 100 nM-2.5 nM;
  (j) about 75 nM-0.6 nM, preferably about 75 nM-1 nM or about 75 nM-2.5 nM;
  (k) about 50 nM-1 nM; preferably about 50 nM-2.5 nM or about 50 nM-5 nM;
  (l) about 35 nM-0.75 nM; and
  (m) about 25 nM-1 nM or about 25 nM-2.5 nM, about 20 nM-3 nM about 15 nM-4 nM or 10 nM-5 nM.

The concentrations and concentration ranges described above are particularly suitable for fast growing suspension mammalian cells, such as CHO cells, which is a preferred embodiment for commercial production cell lines. However, different cell lines may have different folic acid consumption properties. Suitable concentrations, however, can easily be determined experimentally by the skilled person. The folate comprised in the selective culture medium is preferably folic acid and according to one embodiment, folic acid is the only folate comprised in the selective culture medium that contributes to the limiting concentration of folate.

According to one embodiment, the host cells provided in stage (a) comprise a heterologous polynucleotide encoding a folate transporter as first selectable marker and a heterologous polynucleotide encoding a second selectable marker which processes a substrate which is a folate, a derivative of a folate and/or a product that can be obtained by the processing of folate. E.g. the second selectable marker may be a dihydrofolate reductase (DHFR) or an enzyme operating downstream or in conjunction with DHFR such as thymidylate synthase (TS) and serine hydroxymethyltransferase (SHMT). Preferably, a membrane-bound folate receptor is used as first selectable marker and the second selectable marker is a dihydrofolate reductase (DHFR). According to this embodiment, stage (b) comprises culturing the host cells in a selective culture medium which comprises folate, preferably folic acid, in a limiting concentration and comprises at least one DHFR inhibitor such as e.g. MTX. As is shown by the examples, when using the novel cell lines described herein the number of high and stable expressing cells in the pool is significantly increased, obtaining suitable cell clones for large scale production from said cell pool is simplified. Less cell clones need to be made what reduces the screening effort. Suitable embodiments of the folate receptor and DHFR as well as suitable selection conditions and concentrations are described above and it is referred to the above disclosure which also applies here. The described concentrations and concentration ranges for folate and antifolate described above can be combined with each other. In one embodiment, a folate concentration of about 0.1 nM -150 nM, 1 nM-125M, 5 nM-100 nM or 7.5 nM to 75 nM is used in combination with an antifolate concentration of 0.1 nM-150 nM, 1 nM to 125 nM, 2.5 nM to 100 nM, 5 nM to 75 nM or 7.5 nM to 50 nM in the selective culture medium. As described, folic acid is preferably used as folate and MTX as antifolate.

Using a respective combination of a folate receptor and DHFR as selectable marker and applying in stage (b) the selection conditions for both markers simultaneously by using an appropriate selective culture medium, results in a very stringent selection system allowing the efficient enrichment of high producing cells from the transfected host cell population. The host cell's viability is considerably increased under selective conditions, if both selectable markers are strongly expressed. Thereby, eukaryotic cells dependent on folate uptake such as mammalian cells can be selected which show an increased expression rate of the product of interest. This concept of using a folate receptor as selectable marker in combination with a further selectable marker involved in the folate metabolism such as preferably a DHFR is disclosed in WO 2010/097240, herein incorporated by reference. As is shown by the examples, the high stringency of the selection system according to this embodiment can be combined advantageously with the novel cells described herein, in particular when mammalian cells are used. This combination further lowers the number of low producers and a more homogenous population of high producing cells can be obtained after selection. This inter alia simplifies single cell cloning of stable producing cells. Furthermore, this combination allows to significantly reduce the MTX concentration necessary for DHFR selection.

According to one embodiment, two or more selection steps are performed in stage (b), wherein the two or more selection steps are based on the same or a different selection principle. For example, if an additional selectable marker is used in addition to the folate receptor and/or DHFR, the selective conditions for said additional selectable marker can be applied prior to (e.g. in a pre-selection step) or simultaneously with applying the selective conditions for the folate receptor and/or DHFR. For example, in case the neomycin phosphotransferase gene (neo) is used as additional selectable marker, stage (b) may comprise first growing cells in a medium e.g. containing G418 in order to select cells that have incorporated the expression vector or the combination of at least two expression vectors and then performing a selection step using a selective culture medium comprising a limiting concentration of folate and an inhibitor of the second selectable marker, such as e.g. MTX when using DHFR as second selectable marker.

According to one embodiment, a flow cytometry based selection is performed in stage (b). A selection step employing flow cytometry, in particular fluorescence activated cell sorting (FACS), has the advantage that large numbers of cells can be screened rapidly for the desired characteristic expression yield.

According to one embodiment, said flow cytometry based selection is performed in addition to, preferably after, one or more selection steps against one or more selectable marker gene(s) were performed. Thereby, high expressing cell clones can be identified in the population of successfully transfected cells and separated out.

According to one embodiment, high expressing cells are identified by detecting the expression of a co-expressed reporter polypeptide such as e.g. green fluorescence protein (GFP), CFP, YFP, luciferase or other common reporter polypeptide that can be detected by flow cytometry. According to this embodiment, stage (a) comprises providing a plurality of host cells comprising at least one heterologous polynucleotide encoding a reporter and stage (b) comprises identifying host cells expressing the reporter based on at least one characteristic of said reporter polypeptide using flow cytometry. In such reporter based selection, the expression of the reporter gene correlates with the expression of the product of interest. The reporter polypeptide may be intracellularly located, thereby marking the expressing cell. According to one embodiment, the expression of the reporter polypeptide is tightly linked to the expression of the product of interest which is a polypeptide. E.g. the reporter polypeptide and the polypeptide of interest may be expressed as separate polypeptides but from the same expression cassette, however, separated by an IRES element (internal ribosomal entry site). Furthermore, the reporter polypeptide and the polypeptide of interest may be expressed as fusion protein. According to one embodiment, in the expression cassette for expressing the polypeptide of interest, the polynucleotide encoding the polypeptide of interest is separated by at least one stop codon from the polynucleotide encoding the reporter. A fusion protein comprising the reporter polypeptide is only expressed if translation reads over the stop codon. As stop codon readthrough occurs only to a certain extent, which can be influenced by the number and design of the stop codon and the culture conditions, a certain proportion of the polypeptide of interest is produced as fusion protein comprising the reporter polypeptide which can be detected by flow cytometry. Using a respective strategy allows to tightly link the expression of the reporter polypeptide to the expression of the polypeptide of interest. The principle of obtaining fusion proteins by stop codon read through will also be explained subsequently in conjunction with an embodiment wherein a fusion protein (not necessarily comprising a reporter) is displayed on the cell surface and e.g. is stained by using a detection compound. For expressing a secreted polypeptide of interest one can additionally include a polynucleotide encoding a membrane anchor either between the stop codon and the polynucleotide encoding the reporter or downstream of the polynucleotide encoding the reporter. The membrane anchor ensures that the reporter polypeptide remains associated with the expressing cell. Thereby, the reporter polypeptide comprised in the fusion protein provides the expressing cells with a trait that is selectable by flow cytometry. The polypeptide of interest is expressed into the culture medium. The higher e.g. the fluorescence of the reporter polypeptide, the more fusion protein is produced and accordingly, the higher is the expression rate of the polypeptide of interest. A respective method is e.g. disclosed in WO 03/014361 to which it is referred.

According to one embodiment, stage (b) comprises:
(i) performing at least one selection under conditions selective for one or more selectable markers expressed by transfected host cells; and
(ii) performing a flow cytometry based selection.

Optionally, one or more further selection steps can be performed prior to or after step (i) and/or step (ii).

According to one embodiment, the flow cytometry based selection comprises selecting a plurality of host cells expressing the polypeptide of interest with a desired yield based upon to the presence or amount of the polypeptide of interest. Preferably, the polypeptide of interest is a secreted polypeptide. According to one embodiment, the polypeptide of interest is detected on the cell surface using a detection compound that binds to the polypeptide of interest. According to one embodiment, the secreted polypeptide of interest is detected while it passes the cell membrane and accordingly is transiently associated with the plasma membrane during polypeptide secretion. A respective flow cytometry based selection system is e.g. disclosed in WO03/099996 to which it is referred.

According to one embodiment, a portion of the polypeptide of interest is expressed fused to a membrane anchor and thus is expressed as membrane-bound fusion polypeptide. Thereby, a portion of the polypeptide is displayed as fusion polypeptide on the cell surface and can be stained using a detection compound. No reporter polypeptide is required for this type of selection even though it may be additionally used. Due to the presence of the membrane anchor, the polypeptide of interest is tightly anchored to the expressing cell. As the amount of produced fusion polypeptide correlates with the overall expression rate of the expressing cell, host cells can be selected via flow cytometry based upon the amount of fusion polypeptide displayed via the membrane anchor on the cell surface. This allows a rapid selection of high producing host cells. To allow efficient selection using flow cytometry, preferably by using FACS, it is advantageous to use special expression cassette designs for expressing the polypeptide of interest. Thus, according to one embodiment, the polynucleotide encoding the polypeptide of interest is comprised in an expression cassette that is designed such that a portion of the expressed polypeptide of interest comprises a membrane anchor. The polypeptide of interest which is fused to a membrane anchor is also referred to as a fusion polypeptide or fusion protein. Several options exist to achieve that result.

According to one embodiment, the host cells provided in stage (a) comprise
(i) a heterologous expression cassette comprising
  aa) the polynucleotide encoding a polypeptide of interest,
  bb) at least one stop codon downstream of the polynucleotide encoding the polypeptide of interest, and
  cc) a further polynucleotide downstream of the stop codon encoding a membrane anchor and/or a signal for a membrane anchor;
and
(ii) at least one heterologous expression cassette comprising a polynucleotide encoding a selectable marker;
and selection in stage (b) comprises
(i) culturing the host cells under conditions selective for the at least one selectable marker and allowing expression of the polypeptide of interest wherein at least a portion of the polypeptide of interest is expressed as fusion polypeptide comprising a membrane anchor, wherein said fusion polypeptide is displayed on the surface of said host cell;
(ii) performing a flow cytometry based selection, comprising selecting a plurality of host cells expressing the polypeptide of interest with a desired yield based upon the presence or amount of the fusion polypeptide displayed on the cell surface using flow cytometry.

Transcription of the polynucleotide encoding the polypeptide of interest comprised in the above described expression cassette results in a transcript comprising in consecutive order at least
aa) a polynucleotide, wherein translation of said polynucleotide results in the polypeptide of interest;
bb) at least one stop codon downstream of said polynucleotide;
cc) a polynucleotide downstream of said stop codon, encoding a membrane anchor and/or a signal for a membrane anchor.

At least a portion of the transcript is translated into a fusion polypeptide comprising the polypeptide of interest and the membrane anchor by translational read-through of the at least one stop codon. This design of the expression cassette that is used in this embodiment has the effect that through translational read-through processes (the stop codon is "leaky") a defined portion of the polypeptide of interest is produced as a fusion polypeptide comprising a membrane anchor. Thus, at least a portion of the transcript is translated into a fusion polypeptide comprising the polypeptide of interest and the membrane anchor by translational read-through of the at least one stop codon. Translational read-through may occur naturally due to the choice of the stop codon/design of the translation termination signal or can be induced by adapting the culturing conditions, e.g. by using a termination suppression agent. This read-through level results in a certain proportion of fusion polypeptides. These fusion polypeptides comprise a membrane anchor, which tightly anchors the fusion polypeptides to the cell surface. As a result, the fusion polypeptide is being displayed on the cell surface and cells displaying high levels of membrane-anchored fusion polypeptide can be selected by flow cytometry, preferably by FACS. Thereby, host cells are selected that express the polypeptide of interest with high yield. Details and preferred embodiments of this stop codon read-through based technology are described in WO2005/073375 and WO 2010/022961 and it is referred to this disclosure for details.

According to one embodiment, the expression cassette additionally comprises iv) a polynucleotide encoding a reporter polypeptide, such as e.g. GFP. Said polynucleotide encoding the reporter polypeptide is located downstream of the stop codon. Upon stop codon read-through a fusion polypeptide is obtained which comprises the reporter, thereby allowing selection by flow cytometry based on the characteristics of the reporter polypeptide such as e.g. its fluorescence. Details of said embodiment are already described above and it is referred to the above disclosure. Preferably, the polynucleotide encoding the reporter polypeptide is located downstream of the polynucleotide encoding a membrane anchor.

According to an alternative embodiment, a portion of the polypeptide of interest is expressed as cell surface displayed fusion polypeptide using the technology described in WO2007/131774. Here, through transcription and transcript processing at least two different mature mRNAs (mRNA-polypeptide of interest) and (mRNA-polypeptide of interest-anchor) are obtained from the expression cassette encoding the polypeptide of interest. Translation of the mRNA-polypeptide of interest results in the polypeptide of interest. Translation of the mRNA-polypeptide of interest-anchor results in a fusion polypeptide comprising the polypeptide of interest and a membrane anchor. As a result, this fusion polypeptide is again displayed on the cell surface and cells displaying high levels of membrane-anchored fusion polypeptide can be selected by flow cytometry, preferably FACS. Thereby, again host cells can be selected that have a high expression rate. According to one embodiment, the expression cassette additionally comprises a polynucleotide encoding a reporter polypeptide, such as e.g. GFP. Said polynucleotide encoding the reporter polypeptide is located downstream of the intron. Thereby, a fusion polypeptide is obtained which comprises the reporter polypeptide, thereby allowing selection by flow cytometry based on the characteristics of the reporter polypeptide such as e.g. its fluorescence. Preferably, the polynucleotide encoding the reporter polypeptide is located downstream of the polynucleotide encoding a membrane anchor. Thereby, the reporter is located inside the host cell.

Both exemplary embodiments described above result in that a portion of the polypeptide of interest is expressed as fusion polypeptide that is displayed at the surface of the host cells, and cells displaying high levels of membrane-anchored fusion polypeptides (indicating a high level of secreted polypeptide) can be selected e.g. by flow cytometry, in particular by fluorescence activated cell sorting (FACS). Here, different embodiments are available. E.g. if a reporter polypeptide is comprised in the fusion polypeptide, high expressing host cells can be selected based upon a characteristic of the reporter polypeptide, e.g. its fluorescence. Furthermore, appropriately labelled detection compounds can be used as will be described briefly in the following.

According to one embodiment, stage b) comprises selecting a plurality of eukaryotic host cells expressing the polypeptide of interest with a desired yield based upon the presence or amount of the fusion polypeptide displayed on the cell surface using flow cytometry by contacting the host cells with a detection compound binding the fusion polypeptide displayed on the cell surface and selecting a plurality of host cells expressing the polypeptide of interest with a desired yield based upon the presence or amount of the bound detection compound using flow cytometry. Thus, cells may be contacted with an appropriately labelled detection compound that binds the fusion protein, e.g. the portion corresponding to the polypeptide of interest. The detection compound used for binding to the fusion polypeptide may have at least one of the following characteristics: said compound may be labelled, in particular fluorescently labelled, it may be an antigen, it may be an immunoglobulin molecule or a binding fragment thereof or it may be protein-A, -G, or -L. The detection compound used for binding the fusion polypeptide at the cell surface can for example be an immunoglobulin molecule or a fragment thereof such as an antibody or antibody fragment, recognising the fusion polypeptide. Basically all accessible portions of the fusion polypeptide can be detected, thereunder also the portion corresponding to the polypeptide of interest which is secreted in parallel to the fusion polypeptide in soluble form. In order to allow detection and selection, said detection compound used for binding the fusion polypeptide may be labelled. The labelled detection compound that binds the fusion polypeptide displayed on the cell surface thereby labels, respectively stains the cell surface. The higher the amount of fusion polypeptide that is expressed by the host cell, the more labelled detection compound is bound and the more intensive is the staining. This has the advantage that the flow cytometry based selection of the host cells can be easily performed as not only the presence but also the amount of the bound detection compound can be determined. To select high producing host cells, those host cells can be selected from the population of host cell which are most effectively, respectively intensively labelled by the detection compound. The label is suitable for flow cytometry based selection, in particular FACS selection. A fluorescent label is preferred as this allows easy detection by flow cytometry.

According to one embodiment, the expression cassette is constructed such that approximately ≤50%, ≤25%, ≤15%, ≤10%, ≤5%, ≤2.5%, ≤1.5%, ≤1% or less than ≤0.5% fusion polypeptide is obtained. The remaining portion is produced as the secreted polypeptide form not comprising the membrane anchor.

The membrane anchor may be of any kind as long as it enables anchorage of the polypeptide of interest to the cell membrane and thus allows the display of the fusion polypeptide on the cell surface. Suitable embodiments include but are not limited to a GPI anchor or a transmembrane anchor. A transmembrane anchor is preferred to ensure tight binding of the fusion polypeptide to the cell surface and to avoid shedding of the fusion protein. Particularly preferred, in particular when expressing antibodies as polypeptide of interest, is the use of an immunoglobulin transmembrane anchor. Other membrane anchors and preferred embodiments of an immunoglobulin transmembrane anchor are described in WO2007/131774, WO2005/073375 and WO 2010/022961.

According to one embodiment, the host cells express an immunoglobulin molecule such as an antibody as polypeptide of interest. The polynucleotide encoding the heavy chain of an immunoglobulin molecule and the polynucleotide encoding the light chain of an immunoglobulin molecule may be comprised in the same expression cassette or preferably, are comprised in separate expression cassettes as is described above in conjunction with the first aspect. When using an expression cassette design as described above, wherein a portion of the polypeptide of interest is produced as membrane-anchored fusion polypeptide by translational readthrough or alternative splicing, such design is used for expressing the antibody heavy chain.

According to one embodiment, two or more flow cytometry based selection cycles may be performed in stage (b) to select and enrich high expressing host cells.

In one embodiment, host cells expressing a high amount of polypeptide of interest which accordingly depict a high signal are sorted using fluorescence-activated cell sorting (FACS). FACS sorting is advantageous, since it allows rapid screening of large numbers of host cells to identify and enrich those cells which express the polypeptide of interest with a high yield. This embodiment is particularly suitable if the cells are selected based upon the expression of a fusion protein as described above. Those cells, showing the highest fluorescence rate can be identified and isolated by FACS. A positive and statistically significant correlation between fluorescence, as determined by FACS, and the amount of produced polypeptide is found. Therefore, FACS sorting can be used not only for a qualitative analysis to identify cells expressing a polypeptide of interest in general, but can actually be used quantitatively to identify those host cells that express high levels of the polypeptide of interest. Thereby the best producing cells can be selected/enriched in stage (b).

According to one embodiment, cells which express the polypeptide of interest with the desired yield, e.g. above a certain threshold and/or the top 15%, top 10%, top 5% or the top 2% of the host cells, are selected as pool. E.g. several high expressing cells, e.g. at least 10, at least 20, at least 30, at least 50, at least 100, at least 200, at least 300, at least 500, at least 1000 or at least 5000 high expressing cells can be selected in stage (b) and sorted into a cell pool. This cell pool comprising a plurality of different high expressing cells is also referred to as high expressing cell pool. Said cell pool comprising different individual high expressing cells can then be used in order to obtain individual cell clones for large scale production of the polypeptide of interest.

According to one embodiment, the eukaryotic cells provided in stage (a) are mammalian cells, preferably rodent cells, more preferably hamster cells such as CHO cells. Suitable and preferred embodiments are described above in conjunction with the first aspect and it is referred to the above disclosure. As described above, according to one embodiment, said CHO cells have lost a portion of the telomeric region of chromosome 8 wherein said lost portion comprises gene FAM60A. Alternative embodiments are also described above. These cells have particularly favorable characteristics with respect to yield and stability. According to one embodiment, the method according to the second aspect comprises a step of analyzing whether expression of gene FAM60A is reduced or eliminated. Such analysis may be performed after selection, in particular DHFR selection. Details of such analytical method are already described above in conjunction with the first aspect of the present disclosure and are also described below in conjunction with the method according to the fifth aspect and it is referred to the respective disclosure.

Further preferred embodiments in particular with respect to the eukaryotic cells according to the first aspect which preferably are mammalian cells, the expression vector, or combination of expression vectors are described in detail above. It is referred to the above disclosure.

Cells obtained as a result of the selection method according to the second aspect can be isolated and cultured as individual cells. It is, however, also possible to use an enriched population of different host cells, i.e. a cell pool, in the downstream process. The obtained host cells can also be subjected to additional qualitative or quantitative analysis, or can be used e.g. in the development of a clonal cell line for protein production. A clonal cell line may be established from a selected host cell which stably expresses the product of interest with high yield.

Thus, according to one embodiment, selected cells are cultivated to provide cell clones, in particular in the form of clonal cell cultures. A clonal cell culture is a cell culture derived from one single ancestral cell. In a clonal cell culture, all cells are clones of each other. Preferably, all the cells in a cell culture contain the same or substantially the same genetic information. In certain embodiments, the amount or concentration of the polypeptide of interest in the cell culture is determined to determine the productivity. E.g. the titer can be measured by analysing the culture supernatant. According to one embodiment, after determining the productivity performance of each individual clone, a titer ranking is made to select the best producing clones as production clones. Furthermore, a stability study can be performed with the obtained cell clones. However, as is shown in the examples, using the novel cells described herein as host cells provide after selection recombinant cell clones showing a significantly improved stability. Thus, losses in expression stability are rarer with respective host cells and furthermore, if occurring, often only results in a less dramatic decrease in the productivity compared to when using cells wherein functional expression of gene FAM60A is not reduced or eliminated. Therefore, stability analyses may be shortened or even skipped which is an important advantage as it shortens the time that is required for obtaining stably expressing cell clones that can be used for large scale production of the product of interest.

C. Method for Producing a Product of Interest

According to a third aspect, a method is provided for producing a recombinant product of interest, comprising using a eukaryotic cell according to the first aspect as host cell for recombinant expression of the product of interest.

As described above, the novel eukaryotic cells provided herein are particularly suitable as production host cells for recombinantly producing a product of interest such as a polypeptide of interest. Suitable and preferred examples of said eukaryotic cell, wherein the effect of protein FAM60A in said cell is impaired, preferably by reducing or eliminating the functional expression of gene FAM60A, as well as suitable and preferred examples of the product of interest are described in detail above and it is referred to the above disclosure which also applies here. As described above, the eukaryotic cell preferably is a vertebrate cell, more preferably a mammalian cell. Particularly advantageous is the embodiment wherein in addition to FAM60A, the effect of the expression product of gene C12orf35 is impaired, for example by reducing or eliminating functional expression of gene C12orf35 as it was found that thereby, the production yield can be significantly improved. By impairing the effect of protein FAM60A as well as of protein C12orf35, mammalian host cells can be provided which show improved characteristics with respect to both features, long-term stability as well as production yield, and hence key features important for the large-scale production of a product of interest, in particular a polypeptide of interest.

The eukaryotic host cell which preferably is a mammalian cell comprises stably integrated into the genome a polynucleotide encoding a product of interest. Introduction of said polynucleotide can be achieved by stable transfection as described above. Selection of successfully transfected cells may occur using the method according to the second aspect.

According to one embodiment, the method comprises
(a) culturing host cells according to the first aspect under conditions that allow for the expression of the product of interest;
(b) isolating the product of interest from said cell culture medium and/or from said host cells; and
(c) optionally processing the isolated product of interest.

According to one embodiment, said host cells are cultured under serum-free conditions. The expressed product of interest may be obtained by disrupting the host cells. Preferably, the product of interest is a polypeptide. The polypeptide is preferably expressed, e.g. secreted, into the culture medium and can be obtained therefrom. For this purpose, an appropriate leader peptide is provided in the polypeptide of interest. Leader sequences and expression cassette designs to achieve secretion are well known in the prior art. Also a combination of the respective methods is possible. Thereby, polypeptides such as proteins can be produced and obtained/isolated efficiently with high yield.

The product of interest which preferably is a polypeptide that is produced may be recovered, further purified, isolated, processed and/or modified by methods known in the art. For example, the polypeptide may be recovered from the nutrient medium by conventional procedures including, but not limited to, centrifugation, filtration, ultra-filtration, extraction or precipitation. Further processing steps such as purification steps may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction. Furthermore, the isolated and purified product of interest may be further processed, such as e.g. formulated, into a composition, e.g. a pharmaceutical composition.

D. Method for Producing a Eukaryotic Cell

According to a fourth aspect, a method is provided for producing a eukaryotic cell suitable for recombinant production of a product of interest, comprising impairing the effect of protein FAM60A in an eukaryotic cell by altering the genome of said cell and stably transfecting into said cell at least one expression vector comprising a polynucleotide encoding a product of interest. Suitable and preferred embodiments to achieve that result are described above in conjunction with the eukaryotic cells according to the first aspect and it is referred to the above disclosure which also applies here. Non-limiting embodiments are again briefly described in the following.

According to one embodiment, the method comprises altering the genome of the eukaryotic cell to reduce or eliminate the functional expression of gene FAM60A in said cell, thereby impairing the effect of the protein FAM60A in said cell. Suitable ways are described above in conjunction with the eukaryotic cells according to the first aspect of the present disclosure and it is referred thereto.

For example, a gene knock-out may be introduced into the FAM60A gene. According to one embodiment, such gene knock-out is introduced in all copies of the FAM60A gene if more than one copy is present. According to one embodiment, the FAM60A gene is deleted. All copies of the FAM60A gene may be deleted in the genome if more than one copy is present. According to one embodiment, the method comprises deleting a portion of a chromosome, wherein the deleted portion comprises gene FAM60A. The deleted portion may correspond to a telomeric region. However, due to genetic rearrangements, said region may also be located in a different region of the chromosome. Such deletion can be induced e.g. by using an agent that induces chromosome breakages. Here, the cells can be repeatedly treated with such agent in order to obtain cells in which the functional expression of gene FAM60A is reduced or eliminated, e.g. because all copies of said gene are deleted because of induced chromosome breaks.

According to one embodiment, the eukaryotic cell is a metazoan cell, preferably a vertebrate cell, more preferred a mammalian cell. According to one embodiment, the mammalian cell is a rodent cell. Preferably, the rodent cell is a Chinese hamster cell such as a CHO cell, e.g. a CHO cell derived from CHO-K1. According to one embodiment, the method comprises deleting at least a portion of the telomeric region of chromosome 8 in a hamster cell, wherein said deleted portion comprises the FAM60A gene. As is shown by the examples, CHO cells comprising a respective deletion in the telomeric region of chromosome 8, here the q arm, have particularly favorable expression characteristics and thus are particularly suitable as host cells for recombinant production. According to one embodiment, the deleted telomeric region comprises the FAM60A gene and one or more or all genes selected from the group consisting of Caprin2, Ipo8 and RPS4Y2. According to one embodiment, the deleted region additionally comprises at least a portion of or all of the Tmtc1 gene. According to one embodiment, the method comprises deleting at least a respective portion of the telomeric region in both chromosomes of chromosome pair 8. Non-limiting alternative names of the aforementioned individual genes and/or the encoded proteins are also indicated in Table 1 above and the respective genes are, as well as homologs and orthologs, encompassed by the scope of the terms used above for the individual genes.

As described above, the telomeric region of chromosome 6 in mouse corresponds to the telomeric region of chromosome 8 in Chinese hamster. Thus, the above disclosure with respect to the telomeric region of chromosome 8 of hamster correspondingly applies to the telomeric region of chromosome 6 in mouse.

According to one embodiment, the method comprises causing a chromosome break in the telomeric region of chromosome 8 of the hamster genome (or chromosome 6 of the mouse genome), wherein the breakpoint on chromosome 8 (or chromosome 6 of the mouse genome) is located centromeric of the Fam60a gene, centromeric of the Caprin2 gene, centromeric of the Ipo8 gene or centromeric of the RPS4Y2gene. Thereby, all genes that are present telomeric thereof, i.e. which lie further to the direction of the telomeric end, are deleted. Non-limiting alternative names of the aforementioned individual genes as well as homologs and orthologs are also indicated in Table 1 above and the respective genes and encoded proteins are encompassed by the scope of the terms used above for the individual genes and/or proteins. According to one embodiment, the obtained cells comprising a chromosome break in the telomeric region have one or more of the following characteristics:

a) the breakpoint is located centromeric of the Ipo8 gene;

b) the breakpoint is located within the Tmtc1 gene.

As discussed above, all genes that are located telomeric of the breakpoint, i.e. further into the direction of the telomeric end, are comprised in the deleted region. This includes gene FAM60A. Methods for identifying respective mammalian cells having such breakpoint are described above are also described in the following in conjunction with the fifth aspect of the present disclosure. According to one embodiment, the Ergic2 gene is not deleted.

According to one embodiment, a CHO cell, preferably derived from the cell line K1, is used in order to produce an altered mammalian cell line wherein the effect of protein FAM60A is impaired, preferably by reducing or eliminating the functional expression of gene FAM60A. According to one embodiment, a telomeric region on the q arm of chromosome 8 comprising gene FAM60A is deleted. Details how to achieve that result are known to the skilled person and suitable embodiments are also described herein and it is referred to said disclosure. Particularly advantageous is the embodiment wherein additionally, the effect of the expression product of gene C12orf35 is impaired in said cell, for example by reducing or eliminating functional expression of gene C12orf35 as it was found that thereby, the production yield can be significantly improved. Therefore, according to one embodiment, the method according to the fourth aspect additionally comprises impairing the effect of the expression product of gene C12orf35 in said cell. Ways to achieve these results, preferably by reducing or eliminating functional expression of gene C12orf35 are described above and it is referred to the respective disclosure. Mammalian host cells that are altered so that the effect of both FAM60A and C12orf35 is impaired in said cells have particularly favorable expression characteristics. Thereby, mammalian host cells are provided which show improved characteristics with respect to both features, long-term stability as well as production yield, and hence key features important for the large-scale production of a product of interest, in particular a polypeptide of interest.

According to one embodiment, the method according to the fourth aspect comprises introducing into the eukaryotic cell in which the functional expression of gene FAM60A is reduced or eliminated at least one polynucleotide encoding a product of interest and preferably at least one polynucleotide encoding a selectable marker. According to one embodiment, the polynucleotide encoding a product of interest and the polynucleotide encoding a selectable marker are located on the same or on separate expression vectors. Suitable and preferred embodiments are described above and it is referred to the respective disclosure which also applies here. The expression vector(s) integrate into the genome of the host cells so that stably transfected cells are provided. Host cells that were successfully transfected and express the product of interest can be selected using the method according to the second aspect. It is referred to the above disclosure.

E. Method for Analysing Eukaryotic Cells

According to a fifth aspect, a method is provided for analyzing eukaryotic cells for their suitability as host cells for recombinant expression of a product of interest, comprising analyzing directly or indirectly whether the function of the expression product of gene FAM60A is impaired in said cells. As described above, the eukaryotic cell is preferably a mammalian cell.

This analytical method can be advantageously used e.g. in combination with the method according to the fourth aspect of the present disclosure in order to identify whether a eukaryotic cell was produced, wherein the effect of protein FAM60A was impaired. Furthermore, said method can be used in order to discriminate between stable or unstable clones during the selection/screening process. Furthermore, in embodiments, this method can additionally be used to discriminate between high and low producing clones. By using this analytical method, clones can be identified early in the selection process, which have favorable expression characteristics. This increases the probability to select stable and high producing clones resulting in a higher proportion of high and stable producing clones. Therefore, this analytical method has important applications and provides a further improvement of recombinant expression technologies as it shortens the time required to identify a suitable production clone.

According to a preferred embodiment, the method comprises analyzing whether the functional expression of gene FAM60A is reduced or eliminated in said cells. The analysis whether functional expression of gene FAM60A is reduced or eliminated can be performed directly or indirectly. Non-limiting embodiments are described in the following. Which analytical method is suitable also depends on how the cells are altered to achieve the reduction or elimination of functional expression of endogenous gene FAM60A.

For example, when introducing a knock-out into the FAM60A gene in order to reduce or eliminate expression of gene FAM60A, one can amplify the corresponding DNA section and sequence the amplified DNA in order to confirm that the gene knock-out was introduced in gene FAM60A. If functional expression of gene FAM60A is reduced or eliminated by completely or partly deleting said gene, one can detect the deletion on the DNA level, e.g. using suitable amplification based detection methods to detect the deletion (such methods are known to the skilled person).

According to one embodiment, the expression profile of the eukaryotic cells is analyzed to determine whether functional expression of gene FAM60A is reduced or eliminated. For example, the analysis may comprise performing a qualitative or quantitative RT (reverse transcription) PCR in order to detect the presence, absence, amount or length of FAM60A mRNA. This would be an example of a direct analysis, as the analysis directly involves the transcript of gene FAM60A. Indirect analyses, wherein the expression status of gene FAM60A is indirectly determined by analyzing the expression profile of genes different from gene FAM60A and wherein accordingly, the analysis does not directly involve the analysis of gene FAM60A or its transcript are also suitable and thus encompassed by the term "analyzing whether the functional expression of gene FAM60A is reduced or eliminated". Such indirect analysis are e.g. suitable if a chromosomal portion comprising gene FAM60A (and other genes) is deleted by chromosome breakage and will be described subsequently. For a quantitative analysis, a comparison with a reference (e.g. unaltered corresponding cell) can be performed.

According to one embodiment, it is additionally analyzed directly or indirectly whether the effect of the expression product of endogenous gene C12orf35 is impaired in said cells. This can be analyzed by determining whether the functional expression of gene C12orf35 is reduced or eliminated in said cells. This analysis can be performed mutatis mutandis as was described for gene FAM60A. It is referred to the above discussion.

According to one embodiment, prior to analysis, cells are treated with an agent that induces chromosome breaks in order to delete a portion of the chromosome which comprises the FAM60A gene. As described above, all copies of gene FAM60A could be deleted thereby. The analysis may then comprise analyzing whether treatment with said agent resulted in a deletion of a portion of a chromosome which includes gene FAM60A. The cells are treated with an agent that induces chromosome breakage in an appropriate concentration so that chromosome breakage occurs. Here, also several treatment rounds can be performed. Chromosome breakage may be induced during the selection process if selection involves the use of an agent that induces chromosome breakages in a sufficiently high concentration. A non-limiting example of a suitable agent is e.g. MTX. In this case the cells may comprise a heterologous polynucleotide encoding DHFR as selectable marker in order to be able to survive MTX treatment. However, as discussed above also other agents can be used such as e.g. hygromycine and this was confirmed by examples.

After treating the cells to induce chromosome breaks, the obtained cells can be analysed using the method according to the fifth aspect to determine whether treatment with said agent resulted in a deletion of a portion of a chromosome which includes gene FAM60A. Different embodiments are suitable for that purpose. According to one embodiment, the expression profile of the treated cells is analyzed. For example, it can be analysed whether gene FAM60A or one or more genes located centromeric of gene FAM60A (i.e. further away from the telomeric end into chromosome) are expressed. For example, in case of mouse or Chinese hamster cells, it can be analysed whether gene FAM60A is expressed and accordingly, if its mRNA can be detected (example of a direct analysis) and alternatively or in addition thereto, it can be analyzed whether one or more genes selected from the group consisting of Caprin2, Ipo8, Tmtc1 or genes that are located telomeric of the aforementioned genes are expressed by the cell (example of indirect analysis). Non-limiting alternative names of the aforementioned individual genes are also indicated in Table 1 above and the respective genes are encompassed by the scope of the terms used above for the individual genes and encoded products. If the induced breakpoint is located centromeric of the respective gene(s), said genes are deleted which eliminates or reduces (if other copies of the gene existed elsewhere that are expressed) their expression. As is evident from FIG. 1, gene FAM60A is located telomeric of the aforementioned genes. Thus, if the aforementioned genes are deleted, the deleted region also includes gene FAM60A. Thus, the above genes can be validly used as markers in order to basically indirectly determine whether the induced chromosome breakage resulted in a deletion of gene FAM60A and thus resulted in a reduction or elimination of expression of gene FAM60A. Thus, the analysis of whether expression of gene FAM60A was reduced or eliminated does not necessarily have to be based on a direct analysis of e.g. the FAM60A mRNA and such indirect methods are also encompassed by the method of the fifth aspect. Furthermore, it was found that even though located telomeric of gene FAM60A (i.e. further down into the direction of the telomeric end), also genes such as C12orf35 and Bicd1 can be used as marker to determine whether a chromosome breakage was induced which resulted in a deletion of gene FAM60A. It was found in conjunction with the analysis of Chinese hamster cells such as CHO cells that if gene Bicd1 or C12orf35 is deleted because of a chromosome breakage, the deleted telomeric region usually also includes FAM60A. It was confirmed by analyzing the expression characteristics of several hundred clones that the aforementioned genes can be validly used as markers in order to discriminate cell clones with high and stable expression characteristics from cell clones having low and unstable expression characteristics. The relative expression of the aforementioned genes in CHO cells is shown in FIG. 2.

According to one embodiment, the method according to the fifth aspect is for analyzing hamster cells, preferably CHO cells, and the method comprises analyzing whether expression of gene FAM60A is reduced in said cells by analyzing whether the expression of one or more genes located in the telomeric region of chromosome 8 and being selected from the group consisting of the Tmtc1 gene and genes located telomeric of the Tmtc1 gene is reduced or eliminated in said cells. As described above, respective cells which after treatment with the agent that introduces chromosome breakage do no longer express the Tmtc1 gene and/or genes located telomeric of the Tmtc1 gene usually comprise a deletion in the telomeric region of chromosome 8 which comprises said genes and in particular comprises the FAM60A gene. Genetic material telomeric of the breakpoint is lost.

According to one embodiment, the selected host cells having the above described characteristics are transfected with an expression vector comprising at least one polynucleotide encoding a product of interest and preferably comprising at least one selectable marker. Suitable embodiments are described above in conjunction with the other aspects and it is referred to the above disclosure.

According to one embodiment, prior to performing the analysis using the method according to the fifth aspect, the eukaryotic cells are transfected with at least one heterologous polynucleotide encoding a product of interest and at least one heterologous polynucleotide encoding a selectable marker, and prior to analysis at least one selection step is performed to identify successfully transfected host cells. Suitable embodiments are described in detail above. According to one embodiment, selection involves the use of a selection agent that induces chromosome breakages. In this embodiment, the selectable marker may be DHFR and the selection agent may be MTX. Alternatively, the selection agent may be hygromycin and the selectable marker may be a gene that confers resistance against hygromycin such as e.g. the hph gene. In such applications, wherein the method is performed during or after the selection process, the method according to the fifth aspect can be used as analytical tool in order to identify within the selected cell population such cells, wherein the functional expression of gene FAM60A is reduced or eliminated. As described, such reduction or elimination may be caused or supported by the selection conditions, if e.g. a chromosome breakage is induced thereby which results in a deletion of gene FAM60A and the method according to the fifth aspect allows to identify such cells e.g. based on their expression profile. This allows the identification of such cells or cell clones which because of their expression profile, in particular due to the reduced or eliminated functional expression of gene FAM60A, are particularly suitable for establishing a recombinant production cell line as it can be expected that the high expression of the product of interest remains stable. This particularly, because if gene FAM60A is lost, gene C12orf35 is likewise lost and this significantly increases the expression yield as is described herein. As described, in case of hamster cells such as CHO cells wherein gene FAM60A is located in the telomeric region of chromosome 8 it is preferred that the cells have lost the telomeric region of chromosome 8, preferably the q arm, thereby reducing or eliminating expression of gene FAM60A. The analytical method can be performed after generating cell clones from cells comprised in the population of high expressing cells. According to one embodiment, a plurality of cell clones is analysed for discriminating between stable and unstable and/or between high and low producing cell clones.

According to one embodiment, the method according to the fifth aspect comprises selecting at least one cell wherein the function of the expression product of gene FAM60A is impaired, preferably by reduction or elimination of functional expression of gene FAM60A, for recombinant expression of a product of interest, preferably a polypeptide of interest. Cells having the respective characteristics are particularly suitable for recombinant expression as is shown by the examples. Further embodiments of respective cells are also described in detail above. As described, preferably vertebrate cells such as most preferably mammalian cells are used as eukaryotic host cells.

F. Use of Altered Eukaryotic Cells for Recombinant Production of a Product of Interest According to a sixth aspect, the present disclosure pertains to the use of an isolated eukaryotic cell for recombinantly expressing a product of interest, wherein the genome of the eukaryotic cell is altered so that the effect of protein FAM60A is impaired in said cell. Details with respect to the respectively altered eukaryotic host cells and embodiments suitable for achieving impairment of the effect of protein FAM60A in said cells, preferably by reducing or eliminating functional expression of gene FAM60A were described in detail above and it is referred to the above disclosure which also applies here. Non-limiting embodiments are described briefly below.

The eukaryotic cell may be selected from a metazoan, a vertebrate or mammalian cell. Preferably, the eukaryotic cell is a mammalian cell such as a rodent cell. Preferred are CHO cells. The genome of the eukaryotic cell may be altered as described in detail above. According to one embodiment, additionally the effect of the expression product of gene C12orf35 is impaired in said cell, preferably by reducing or eliminating functional expression of endogenous gene C12orf35. Details with respect to this embodiment and the associated advantages were described in detail above and it is referred to the above disclosure.

According to one embodiment, the product of interest is a polypeptide. Preferably, the polypeptide of interest is upon expression in the eukaryotic cell secreted into the cell culture medium. Details with respect to the polypeptide of interest were described above and it is referred to the respective disclosure. To allow expression of the product of interest, the eukaryotic host cell may be stably transfected with an expression vector comprising a polynucleotide encoding the polypeptide of interest. Details are described above and it is referred to the above disclosure. Preferably, a eukaryotic host cell according to the first aspect is used as eukaryotic host cells. Said cells are described in detail above and it is referred to the above disclosure.

Numeric ranges described herein are inclusive of the numbers defining the range. The headings provided herein are not limitations of the various aspects or embodiments of this disclosure which can be read by reference to the specification as a whole. According to one embodiment, subject-matter described herein as comprising certain elements also refers to subject-matter consisting of the respective elements. In particular, the polynucleotides described herein as comprising certain sequences may also consist of the respective sequences. It is preferred to select and combine preferred embodiments described herein and the specific subject-matter arising from a respective combination of preferred embodiments also belongs to the present disclosure.

The present application claims priority of prior US provisional application no. U.S. 61/919,340 filed on 20 Dec. 2013, the entire disclosure of which is incorporated herein by reference.

EXAMPLES

The following examples serve to illustrate the present invention without in any way limiting the scope thereof. In particular, the examples relate to preferred embodiments of the present invention.

Example 1

Knock-Out of FAM60A in CHO Cells Using TALEN Technology

Two cell clones on the basis of CHO cells derived from the cell line CHO-K1 were made that comprise a knock-out mutation in the FAM60A gene. For creating the FAM60A mutant cells, TALEN (Transcription Activator-Like Effector Nucleases) technology was used. For the knock-out of FAM60A, a coding region (presumed exon 1) of the gene FAM60A was targeted. The CHO-K1 cells used as parental cell only contain one copy of FAM60A. Thus, a single knock-out per cell is sufficient to impair the effect of FAM60A in said cell.

1. Design/Production and Use of TALENs which are Specific for FAM60A

The following genomic DNA exon sequence of gene FAM60A of the CHO parental cell line was targeted:

(SEQ ID NO: 23)
atgtttggttttcacaagccaaagatgtaccgaagtatagagggctgctg tatctgcagagccaagtcctccagctctcggttcacggacagtaaacgtt atgaaaaggacttccagagctgttttgg The nucleotides of the TALEN binding sites are marked in bold. Two TAL Fok I targeting the coding sequence of FAM60 shown above (SEQ ID NO: 23) were designed. TALEN TAL-L targets and binds the marked 25 nucleotides on the 5' (forward) DNA strand and TALEN TAL-R targets and binds to the marked 25 nucleotides on the 3' (reverse) DNA strand of gene FAM60A as is shown above for SEQ ID NO: 23 (see also Table 2, which additionally shows primer sequences that were subsequently used for identifying knock-outs). The two binding sites are separated by the sixteen nucleotides of the cutting site. Plasmids coding for the two TALENS TAL-L and TAL-R were obtained.

TABLE 2

| TALEN target sequences for FAM60A gene knockout and primer sequences | |
|---|---|
| TAL-L | TGTACCGAAGTATAGAGGGCTGCTG (SEQ ID NO: 24) |
| TAL-R | TGTCCGTGAACCGAGAGCTGGAGGA (SEQ ID NO: 25) |
| Primer 1: | GTCCCAGCACTCATGAGGAT (SEQ ID NO: 26) |
| Primer 2: | CCTCCTAGCTCCAGGTATTT (SEQ ID NO: 27) |
| Primer 3: | GAGGACTTGGCTCTGCAGAT (SEQ ID NO: 28) |
| Primer 4: | TTCCACAGAGCACAGCCGAT (SEQ ID NO: 29) |

A portion of the genomic DNA sequence of gene FAM60A which encompasses the targeted coding sequence shown in SEQ ID NO: 23 and which also extends over the primer binding sites for primers 1, 2 and 4 which are located in intron sections is shown as SEQ ID NO: 30.

2. Transfection of the TALEN Plasmid

Transfection was carried out the using a standard transfection protocol involving electroporation using the parental CHO cells in exponential growth phase with viability over 95% and 5 μg of the each of the TALEN plasmids.

3. Cel-I-Assay and Cell Sorting

The Cel-I-assay was performed according to the manual of SAFC Biosciences. The Cel-I-assay is a standard assay in order to determine the cutting efficiency. In brief, after several days of cultivation, genomic DNA was isolated from the cells and a PCR was performed using primers 1 and 2 (see Table 2). The amplification product was denatured and allowed to renature. Then, nuclease S and nuclease S enhancer were added and incubated. The digested product was analyzed. If TALEN activity occurred, two smaller bands are present indicating TALEN activity within that region of the genome and therefore, supporting that cells wherein the FAM60A gene is knocked-out are present in the analysed cell pool. From the positive cell pools, single cells were sorted in 96 well plates by limiting dilution.

4. Screening Strategy

Genomic DNA (gDNA) was extracted from each clone in 96 well plates. The gDNA was analyzed by standard procedure to identify knock-out clones by PCR analysis. For this purpose, primers 3 and 4 (see Table 2) were used. In case of a mutation in the cutting region, primer 3 will not bind so that no PCR product is generated. The PCR products resulting from PCR with primers 1 and 2 of gDNA (see above) of positive clones were sequenced in order to analyze the introduced mutation.

Two cell clones with a knock-out mutation were obtained: FAM60A_ko_s16 (s16), with a deletion of 14 nucleotides and FAM60A-ko_s23 (s23) with a deletion of 5 nucleotides. The mutated sequences of the cell clones are shown in Table 3. Each of the deletions results in a frame-shift. Due to the frame-shift within the targeted sequence of FAM60A, stop codons are provided within the reading frame (highlighted in Table 3 by nucleotides in italic letters and underlining). Thus, it is expected that an abnormally short and less- or non-functional FAM60A expression product is expressed by the obtained FAM60A knock-out clones.

TABLE 3

DNA sequence of presumed exon 1 of FAM60A in CHO wildtype (WT - derived from CHO-K1) and two knock-out cell clones (s16 and s23) derived from said WT. Nucleotides of TALEN binding sites are highlighted in bold and nucleotides of premature stop codons in italic letters and underlining.

| | |
|---|---|
| WT | atgtttggttttcacaagccaaagagtaccgaagt atagagggctgctgtatctgcagagccaagtcctcc agctctcggttcacggacagtaaacgttatgaaaag gacttccagagctgttttgg (SEQ ID NO: 23) |
| s16 (del14) | atgtttggttttcacaagccaaaga*gtaccga agtatagagggctgctg*atcctccagctctcggt tcacggacag*taa*acgtta*tga*aaaggacttccag agctgttttgg (SEQ ID NO: 31) |
| s23: (del5) | atgtttggttttcacaagccaaaga*gtaccga agtatagagggctgctg*tatctgccaag*tcctccag ctct*cggttcacggaca*g*taa*acgttatgaaaagga cttccagagctgttttgg (SEQ ID NO: 32) |

5. Stability Analysis

The parental WT cell line from which the FAM60A knock-out clones were obtained and the obtained FAM60A knock-out cells were stably transfected with an expression vector encoding an antibody as polypeptide of interest. The transfected expression vector comprised an expression cassette comprising a polynucleotide encoding a neomycin phosphotransferase as selectable marker, an expression cassette encoding DHFR as selectable marker, an expression cassette comprising a polynucleotide encoding the light chain of an antibody and an expression cassette comprising a polynucleotide encoding the heavy chain of an antibody so that a complete antibody was expressed from said expression vector. All expression cassettes in the expression vectors were oriented in the same direction. The expression cassette used for the heavy chain was designed such that a portion of the heavy chain was expressed due to stop codon read through as fusion polypeptide comprising a membrane anchor. The fusion protein was displayed on the cell surface, thereby simplifying FACS analysis (see description). The transfected cells were selected for recombinant expression using G418 and MTX (1 μM) selection. From the selected pools of each stably transfected cell line (CHO WT, s16 and s23), cell clones that expressed the product of interest with good yields were obtained and were cultured for several weeks (7 weeks for WT CHO parental cell line (45 clones) and 8 weeks for the FAM60A knock-out cells (13 clones for s16 and 18 clones for s23)) in order to analyse their expression stability during prolonged culturing. To ensure that production cell lines can be upscaled to high volume bioreactors, stability studies of 12 weeks, in particular additional analysis of the expression stability during 12 week culturing, were also performed. Clones were classified as unstable if they lost more than 25% of their initial volumetric expression titer over the stability period analyzed. Within the usual level of variation some clones are just above or under the border line of 25%. The higher proportion of unstable cones in week 7/8 compared to week 12 for parental cell line can be explained with the variation in the productivity assay for clones which are close to the 25% threshold.

Table 4 compares the stability results that were obtained with the cell lines. As can be seen, the percentage of clones with stable volumetric titer is considerably higher in the clones derived from either FAM60A knock-out cell line compared to the clones that are derived from the wildtype cell line. This demonstrates that impairing the effect of endogenous FAM60A in the cell, here by introducing a gene knock-out, significantly improves the stability results during prolonged culturing. The ratio of stable versus unstable clones is significantly increased when using the cells of the invention so that more stable clones are obtained that maintain their favorable high expression characteristics during prolonged culturing. The antibody that was recombinantly expressed in this example was not codon-optimized and showed in the parental cell line a very high degree of instability. Because of this significant instability, this project was chosen as example for comparison because it demonstrates the significant benefits that are achieved with the present invention even when being confronted with difficult projects wherein instability rates are with the wildtype unmodified cell line high. However, as discussed above, with other projects, the instability rates are with the parental CHO wildtype cell line less high. However, in all cases analysed, the host cells according to the present disclosure, wherein the effect of FAM60A is impaired in said cells, achieve in comparison with the unmodified wildtype a significant increase in the amount of stable cells. The stability rates can reach up to 60% or more, 70% or more, 80% or more, 85% or more, or even 90% or more, depending on the project. With the cells according to the present disclosure, which e.g. comprise a gene knock-out in the FAM60A gene or wherein a portion of the telomeric region comprising gene FAM60A is lost due to chromosome breakage, instable clones appeared irrespective of the project analysed significantly less frequently and even if appearing, the loss in volumetric productivity was less pronounced compared to corresponding cells wherein the effect of FAM60A is not impaired in the cell. Therefore, due to the increased percentage of stable clones that are obtained after transfection and selection, the cells according to the present disclosure allow to significantly shorten or even skip long-term stability studies. The stability studies of the FAM60A knock-out clones confirm the beneficial results that are achieved with the technology of the present disclosure.

TABLE 4

Results of stability studies

| Cell line | Stable clones 7/8 weeks | Unstable clones 7/8 weeks | Stable clones 12 weeks | Unstable clones 12 weeks |
|---|---|---|---|---|
| Parent cell line (7 and 12 weeks) | 13.3% | 86.7% | 24.3% | 75.7% |
| FAM60A knock-out cell line s16 (8 and 12 weeks) | 61.5% | 38.5% | 61.5% | 38.5% |
| FAM60A knock-out cell line s23 (8 and 12 weeks) | 44.4% | 55.6% | 47.1% | 52.9% |

The results are also shown in FIG. 3 and demonstrate the important advantages that are achieved when impairing the effect of FAM60A in the cells, here by gene knock-out.

Example 2

Reducing C12orf35 Gene Expression by RNA Interference (RNAi) Increases Expression Yield As described above, it is particularly preferred to additionally impair the effect of the expression product of gene C12orf35 in the eukaryotic cell wherein the effect of the FAM60A protein is impaired. Suitable methods for achieving impairment are described above and include, but are not limited to, reducing or eliminating functional expression of the endogenous C12orf35 gene. It was found that impairing the effect of the expression product of gene C12orf35 in a eukaryotic cell, such as preferably in a mammalian cell, surprisingly significantly increases the expression yield of a recombinant polypeptide of interest that is expressed from the respective cells. This beneficial effect with respect to expression yield that is obtained when reducing functional expression of gene C12orf35 is demonstrated in this example 2.

In order to demonstrate that reducing expression of gene C12orf35 results in an increase in volumetric and specific productivity, siRNAs were designed against different target genes located in the telomeric region of chromosome 8 of the Chinese hamster genome analysed (CHO-K1). siRNAs were designed against the following target genes listed in Table 5:

TABLE 5 siRNAs against different target genes

| Target gene | Sense | Antisense |
|---|---|---|
| METTL20_1 (4833442J19Rik) | CCCUGAUGUUGUUAG AGGATT (SEQ ID NO: 33) | UCCUCUAACAACAUC AGGGTT (SEQ ID NO: 34) |
| C12orf35_1 | CAUCCAGACAAAUCU UACATT (SEQ ID NO: 35) | UGUAAGAUUUGUCUG GAUGTG (SEQ ID NO: 36) |
| C12orf35_2 | CCAGAAAGAUAAAUC UACATT (SEQ ID NO: 37) | UGUAGAUUUAUCUUU CUGGTA (SEQ ID NO: 38) |

TABLE 5-continued siRNAs against different target genes

| Target gene | Sense | Antisense |
|---|---|---|
| Caprin2_6 | UGACCUGCCCUGAAA GAAATT (SEQ ID NO: 39) | UUUCUUUCAGGGCAG GUCAGT (SEQ ID NO: 40) |
| FAM60A | GCUUCCAGCUCUAAC AGAATT (SEQ ID NO: 41) | UUCUGUUAGAGCUGG AAGCCA (SEQ ID NO: 42) |
| IPO8_1 | GACCCGAACUUUGAC CCUAUU (SEQ ID NO: 43) | UAGGGUCAAAGUUCG GGUCUG (SEQ ID NO: 44) |
| IPO8_2 | CGGAGACUCUUCAAA UUGAUU (SEQ ID NO: 45) | UCAAUUUGAAGAGUC UCCGGA (SEQ ID NO: 46) |
| IPO8_3 | GCCUGAUUGAAGACG AGGAUU (SEQ ID NO: 47) | UCCUCGUCUUCAAUC AGGCUU (SEQ ID NO: 48) |
| Dennd5b_2 | GGGUCUCCCUUAUUC AAGAUU (SEQ ID NO: 49) | UCUUGAAUAAGGGAG ACCCUG (SEQ ID NO: 50) |
| Amn1_4 | GCUGCUUAAGUAUUA CUGAUU (SEQ ID NO: 51) | UCAGUAAUACUUAAG CAGCCA (SEQ ID NO: 52) |
| TMTC1_1 | GUAUACCUGUGAUAA AACAUU (SEQ ID NO: 53) | UGUUUUAUCACAGGU AUACAT (SEQ ID NO: 54) |
| TMTC1_2 | CGGUGAAUGUCAUUC UACAUU (SEQ ID NO: 55) | UGUAGAAUGACAUUC ACCGCA (SEQ ID NO: 56) |
| siRNA negative control (no effect on expression - referred to as siRNA control) | Silencer Negative Control siRNA #5 (50 uM) (Ambion, Cat#AM4642) | |

The used siRNAs were validated using real-time RT-PCR to confirm that they reduce the expression of the target genes by gene silencing. Gene expression was normalized to 18S RNA. The gene expression observed when transfecting the siRNA negative control was set as 100%. The relative reduction of expression of the target gene is shown in the subsequent Table 6 for the two different siRNAs against target gene C12orf35:

TABLE 6

| Concentration | Gene expression (siRNA 1) | Gene expression (siRNA 2) |
|---|---|---|
| 100 pmol | Approx. 28% | Approx. 37% |
| 125 pmol | Approx. 25% | Approx. 38% |
| 150 pmol | Approx. 35% | Approx. 30% |

Furthermore, it was confirmed that the target siRNAs used in this experiment does not inhibit growth of the transfected cells. Furthermore BLAST (Basic Local Alignment Search Tool) analysis based on the available Chinese hamster genome data does not indicate any off-target effects.

The following cell lines were transfected: A CHO cell line derived from CHO-K1 was used as parental cell line. Said cell line expresses the above genes as is shown in FIG. 2. This parental cell line was not transfected with an expression vector and served as control. CHO cells (clones and pools)

derived from said parental cell line which comprised an expression vector encoding an antibody as protein of interest stably integrated into the genome was used to determine the effect of the siRNAs. The expression vector comprised in said cell clone comprised selectable marker genes and the antibody heavy chain and the antibody light chain were expressed from different expression cassettes. The expression cassette used for the heavy chain was designed such that a portion of the heavy chain was expressed due to stop codon read through as fusion polypeptide comprising a membrane anchor. The fusion protein was displayed on the cell surface, thereby simplifying FACS analysis (see description). Said CHO cells expressed the above-mentioned siRNA target genes similar to the parental cell line which was determined by microarrays for hundreds of clones and pools. A CHO clone which recombinantly expressed the antibody was used in order to determine whether a downregulation of one or more of the above target genes results in an increase of the expression of the polypeptide of interest. If this was the case, an increase of the volumetric antibody productivity of said cell clone would be seen which is detectable using FACS analysis.

The CHO clone comprising the expression vector stably integrated into the genome was transfected either with a siRNA control (not having an effect on gene expression) or with one of the above-mentioned siRNAs against the target genes. After transfection of the siRNAs it was analyzed whether the reduction of the expression of the target gene results in an increase of the expression of the antibody. Inter alia, the transfected cells were stained by using a fluorescent detection compound and analysed by FACS in order to determine the expression rate of the antibody. The more antibody is produced, the more displayed fusion protein can be stained using a labeled compound and accordingly, the higher is the fluorescence signal detected by FACS. Therefore, the higher the intensities in the FACS profiles, the more antibody is expressed.

The results are shown in FIG. 4A to L for the different siRNAs tested. The left peak in the profiles corresponds to the signal obtained for the parental cell line, which does not express the antibody. The two other curves represent the results obtained with the antibody expressing cell clone which was transfected with either the siRNA-negative control (no effect on expression) or with the tested siRNA which reduces the expression of its target gene. If the tested siRNA and accordingly, the downregulation of the target gene does not have an effect on the expression of the antibody (i.e. no upregulation of volumetric productivity), the obtained fluorescence curve for the siRNA-negative control and the fluorescence curve obtained for the target siRNA overlap and thus are basically identical. This was in essence the case for all tested target genes on clone level, except for gene C12orf35. For FAM60A, however, a slight shift was seen on pool level which is assumed to be attributable to the increased expression stability (data not shown).

As can be seen from the results obtained with the siRNAs against C12orf35 (see FIGS. 4B and C), the fluorescence peaks obtained for the siRNA-negative control and the siRNA against gene C12orf35 clearly separate upon silencing gene C12orf35 using RNAi. The fluorescence peak obtained for the cell clone transfected with the siRNA against gene C12orf35 clearly shifts to the right (marked by arrows), which means that the fluorescence is significantly increased. This observed increase in fluorescence is attributable to a higher expression of the antibody as more fusion protein is present and thus is stained on the cell surface. Therefore, this experiment clearly shows that a downregulation of the functional expression of gene C12orf35 directly results in a significant upregulation of the recombinant expression of the antibody (yield of antibody). The same remarkable shift in the FACS profiles was observed when using said siRNAs against C12orf35 in all three concentrations. A prolonged reduction of the expression of gene C12orf35 by RNA interference can be achieved if for example stably integrated in an expression vector which expresses an RNAi inducing transcript, as is for example described in the description. Furthermore, a reduction or elimination of the expression of gene C12orf35 can be achieved by gene knockout or gene deletion/mutation, according to one embodiment by deleting a portion of the telomeric region of chromosome 8 in case of hamster cells such as CHO cells, as described in the description. Furthermore, as is described therein, it is also feasible to reduce or eliminate the effect of the expression product e.g. by introducing one or more mutations which result in a non-functional or less functional protein.

The achieved increase in the expression of the recombinant polypeptide of interest was also confirmed by analysis of the mRNA expression level of the heavy and the light chain (which were expressed from separate expression cassettes, see above). The results are shown for two different polypeptides of interest (antibody 1 and 2) in FIGS. 5 and 6. The data shown is normalized to the siRNA negative control (125 pmol). It was found that reduction of expression of gene C12orf35 leads to significantly higher mRNA levels of the heavy chain and the light chain of the expressed antibody. In comparison, reduction of expression of other tested target genes did not have an impact on the mRNA expression level of the heavy and the light chain. Thus, reduction of the expression of gene C12orf35 results in a significant increase in the mRNA level of the recombinant polypeptide of interest. Furthermore, it was observed that also other introduced genes such as selection markers are upregulated if gene C12orf35 is silenced. An experiment, in which the gene silencing effect was measured over time starting on day 3, showed that siRNA1 (see siRNA C12orf35_1 in Table 7) had a longer effect compared to siRNA2 (see siRNA C12orf35_2 in Table 7). In addition, cell numbers and titer were determined throughout the time course experiment and revealed that downregulation of C12orf35 leads to significantly higher specific productivities (see FIG. 7).

Furthermore, expression of the C12orf35 gene relative to 18S RNA was analysed in an antibody expressing clone upon repression with siRNA 1 and 2 and compared to different controls. The results are shown in the subsequent Table 7:

TABLE 7

|  | 18S | C12orf35 | Heavy Chain | Light Chain |
| --- | --- | --- | --- | --- |
| siRNA C12orf35_1 | 97% | 0.0129% | 0.8517% | 3.4639% |
| siRNA C12orf35_2 | 91% | 0.0186% | 1.0643% | 2.9623% |
| siRNA control | 93% | 0.0617% | 0.3098% | 0.9195% |
| cells untreated | 100% | 0.0782% | 0.2713% | 0.7840% |
| cells lipofectamin | 114% | 0.0648% | 0.2633% | 0.8019% |

Example 3

Generation of a CHO Cell Line which Comprises a Deletion in the Telomeric Region of Chromosome 8 which Deletes Gene FAM60A and Gene C12orf35

A novel CHO cell line (C8DEL) was generated, which comprises a deletion in the telomeric region of the q arm of chromosome 8. The deletion was induced by chromosome breakage. The deleted portion comprised gene FAM60A as well as among others gene C12orf35 which is located telomeric from gene FAM60A (see FIG. 1). Said novel cell line was obtained from a parental cell line derived from CHO-K1. Said cell line with a chromosome break in chromosome 8 was prepared as follows. The parental CHO cells were split at 2E5 cells/ml in culture medium comprising 0.5 µM, 1 µM or 2 µM MTX. After six days the cell viabilities were around 30-40%. Cells were centrifuged at 180×g for 5 min and cultivated in culture medium without MTX to allow the cells to recover until viabilities were above 95% (after ca. 21 days). This procedure was repeated two more times. Single cell clones were obtained from cell pools. Overall 561 cell clones were grown and DNA was isolated using the "Extract-N-Amp Blood PCR Kit". PCR screening using primers detecting the gene Ipo8 was performed. Three out of the 561 clones were "IPO8 negative" indicating the loss of telomeric region of chromosome 8 which includes the Ipo8 gene. The Ipo8 gene is located centromeric of the FAM60A gene (see FIG. 1). Thus, if the Ipo8 gene is deleted due to chromosome breakage, all genes located telomeric of the Ipo8 gene (and accordingly also the FAM60A gene and gene C12orf35) are deleted as well. These three clones were expanded and further evaluated. One of these clones is referred to as "C8DEL" cell line. Using PCR technique the breakpoint of the telomeric region of chromosome 8 from the C8DEL cell line could be determined. The breakpoint was determined between two PCRs, called PCR20 and 28:

```
PCR20:
                                              (SEQ ID NO: 57)
fwd         5'-ACC AGT GAA TAA TCG TGT TT-3', (SEQ ID NO: 58)
rev         5'-CTA TGA GTC AAT GTC CCA AG-3';

PCR28:
                                              (SEQ ID NO: 59)
fwd         5'-CAC ACA CAA CCT CCT AAC AAC CC-3', (SEQ ID NO: 60)
rev         5'-TTC CGC ACC GAC TCA GTT CT-3'
```

The breakpoint lies within the Tmtc1 gene. Additionally it could be demonstrated that the identified breakpoint of C8DEL cell line is stable over several weeks of cultivation (determined via PCR). Transfecting this novel cell line with an expression vector encoding a product of interest increases the chances of selecting stable producing clones with high expression capacity as is shown in the following. Transfection and MTX treatment of C8DEL cell line apparently has no effect on the breakpoint (no further genetic material is lost) as was determined based on the analysis of transfected clones.

Example 4

Analysis of the Characteristics of the Cell Line C8DEL

The cell line C8DEL was analyzed for its performance when recombinantly expressing a polypeptide of interest and compared to the parental cell line from which the cell line C8DEL was derived. As described above, said parental cell line does not comprise a corresponding deletion in the telomeric region of chromosome 8.

4.1. Analysis of Productivity

The volumetric productivity of C8DEL was evaluated in comparison to the parental cell line from which it was derived. Stable as well as transient transfections were performed.

Stable Transfection

Cell cultivation, transfection and screening were carried out in shake flasks using suspension growing CHO cells in a chemically defined culture medium. Cells were transfected by electroporation with different expression vectors encoding a variety of antibodies and therapeutic proteins. Expression vectors used comprised an expression cassette comprising a polynucleotide encoding a neomycin phosphotransferase as selectable marker and an expression cassette encoding a DHFR as selectable marker. The expression vectors used for expressing antibodies additionally comprised an expression cassette comprising a polynucleotide encoding the light chain of an antibody and an expression cassette comprising a polynucleotide encoding the heavy chain of an antibody so that a complete antibody was expressed from said expression vector. The expression vectors used for expressing a polypeptide which was not an antibody, comprised an expression cassette comprising a polynucleotide encoding the polypeptide in addition to the selection markers. All expression cassettes in the expression vectors were oriented in the same direction. The vector was suitable for FACS selection and details of such vector are described above.

Depending on the cell viability, the first selection step was started 24-48 h after transfection by adding G418 selective medium to the cells. As soon as cells recovered to a viability of above 80%, a second selection step was applied by passaging the cells to 500 nM MTX or 1 µM MTX.

Volumetric productivity of the selected cell populations was analyzed after G418 and MTX selection steps via overgrown shake flask batch cultures in medium with G418 or MTX. The G418 batch was done in 30 ml (125 ml flask) and MTX fed-batch in 100 ml (500 flask). G418 batch cultures were seeded at 1E5 vc/ml in shake flask and cultivated in a shaker cabinet (not humidified) at 150 rpm and 10% CO2. Fed-batches were seeded at 4E5 vc/ml. Viability of cells had to be >90% when starting the assay. Titer determination took place at day 14. Antibody titers in the cell culture supernatant were determined by protein-A HPLC 14 days after starting the culture.

After the first selection step (G418 selection) a massive volumetric titer increase (12-35 fold) could be detected for the stably transfected C8DEL pools in comparison to the stably transfected parental pools. After the second selection step (MTX selection) the C8DEL pools were expressing 4-7 fold more polypeptide of interest in comparison to the transfected parental cells, as exemplified by 2 antibodies (antibody 1 and antibody 2). Volumetric G418 and MTX (fed-batch) titers of C8DEL in comparison to the parental CHO cell line not comprising the deletion in the telomeric region of chromosome 8 are exemplarily displayed for two antibody projects in the following Tables 8.a and 8.b. Tables 8.a and 8.b show the volumetric G418 and MTX fed-batch pool titer (antibody) produced in C8DEL in comparison to the parental pools (average of 4 pools/condition are shown).

TABLE 8a

Pool titers of example antibody 1

| Cell line | Pool titer after G418 selection | Pool titer after G418 and MTX selection |
|---|---|---|
| Parental cell line derived from CHO-K1 | 0.02 g/L | 0.62 g/L |
| C8DEL | 0.78 g/L | 4.41 g/L |

TABLE 8.b

Pool titers of example antibody 2

| Cell line | Pool titer after G418 selection | Pool titer after G418 and MTX selection |
|---|---|---|
| Parental cell line derived from CHO-K1 | 0.02 g/L | 0.32 g/L |
| C8DEL | 0.2 g/L | 1.21 g/L |

The results support the conclusion that a deletion in the telomeric region of chromosome 8 which includes the FAM60A gene and the C12orf35 gene is correlated with higher volumetric productivity. Already with respect to volumetric pool titer, the C8DEL cell line is outperforming the parental cell line that does not comprise a respective deletion in the telomeric region of chromosome 8. Considering the siRNA results from example 2, it is believed that the volumetric titer increase is due to the loss of gene C12orf35 located on the telomeric part that was lost.

Transient Transfection

C8DEL cells and parental cell line cells grown in culture medium were transiently transfected in triplicates with expression plasmids encoding either eGFP or an Fc fusion protein as model protein of interest. Polyethylenimine (PEI) was used as transfection reagent. The titer of the model protein in the medium supernatant was measured by Protein A HPLC on day 3 and day 6 after transfection. The expression of the model protein was approx. 3 fold higher in C8DEL. The percentage of eGFP-expressing cells was measured 48 h after transfection by flow cytometry with non-transfected cells acting as negative control. Cells exhibiting a fluorescence level greater than 99% of the negative control cells were regarded as "transfected". Cells exhibiting fluorescence level of more than 1000-fold the intensity of the negative control cells were regarded as "highly fluorescent". The number of high fluorescent cells was 2-3 fold higher using the C8DEL cell line compared to the parental cell line from which C8DEL was derived.

This example shows that the advantages of increased volumetric productivity are also achieved when performing a transient transfection with the C8DEL cell line wherein a portion of the telomeric region of chromosome 8 is lost due to chromosome breakage.

4.2. Stability Analysis

The stability characteristics of 46 C8DEL derived clones and 37 clones derived from the parental cell line (which were tested to be IPO8 positive and hence did not lose the telomeric region of chromosome 8) was analysed after stable transfection. All clones recombinantly expressed the same antibody as product of interest and were classified as stable if they were not losing more than 25% antibody titer (volumetric) in 12 weeks. 76% of the analyzed clones from the parental cell line lost more than 25% of titer (volumetric) within 12 weeks of cultivation. Only 24% of the analysed clones were classified as stable. Thus, instability rates were high. In comparison, 67% of the C8DEL clones could be classified as stable and only 33% went instable as is shown in Table 9:

TABLE 9

Results of stability studies

| Cell line | Stable clones | Unstable clones |
|---|---|---|
| Parent cell line (12 weeks) | 24% | 76% |
| C8DEL (deletion of gene FAM60A due to chromosome breakage) (12 weeks) | 67% | 33% |

Using a $\chi 2$-test with a Yates-correction a p-value of 0.0002 could be calculated which supports that C8DEL derived clones have a significant higher tendency to be stable producers. Thus, a significant higher number of stable producing clones for the C8DEL cell line were found. This further supports in particular in conjunction with the knock-out experiments of example 1 that hamster cells such as CHO cells, wherein a portion of the telomeric region of chromosome 8 comprising gene FAM60A is deleted, show superior stability characteristics. Thus, using such cell line for recombinant expression increases the chance that high and stable producing recombinant cells are identified. Furthermore, the volumetric productivity of said clones was analysed (see 4.3.).

4.3. Further Analyses of the Characteristics of C8DEL

The characteristics of the CHO cell line comprising a deletion in the telomeric region of chromosome 8 wherein said deletion comprises gene FAM60A as well as gene C12orf35 were analysed in additional experiments which demonstrate further advantages of said cell line.

Less Single Cell Cloning Required for Selecting High Producers

An advantageous characteristic of the C8DEL cell line is the greater proportion of high producing clones after single cell cloning. It was found that the C8DEL pools contain an enlarged proportion of high producing cells (resulting in an increased volumetric pool titer) compared to the parental cell line derived from CHO-K1. After single cell cloning of C8DEL pools using FACS technology, a significantly greater proportion of clones expressing high quantities of antibody were selected compared to pools derived from the parental WT cell line. Table 10 shows that most clones derived from the parental cell line had a "volumetric 96 well titer" of 0-20 mg/L. In contrast, the majority of clones derived from C8DEL cell line had an average volumetric titer of 80-100 mg/L what is a significant improvement. One advantage of using C8DEL pools is the reduced number of clones which have to be generated to obtain a comparable amount of high and stable producing clones. This significantly reduces the screening effort.

TABLE 10

| 96 well titer (mg/L) | Parental cell line | C8DEL |
|---|---|---|
| 0-20 | 80.3% | 0.8% |
| 20-40 | 6.1% | 3.1% |
| 40-60 | 5.4% | 5.3% |
| 60-80 | 6.1% | 28.2% |
| 80-100 | 1.4% | 32.1% |
| 100-120 | 0.0% | 17.6% |
| 120-140 | 0.7% | 7.6% |
| 140-160 | 0.0% | 3.1% |
| 160-180 | 0.0% | 1.5% |
| 180-200 | 0.0% | 0.8% |

Using the C8DEL cell line as production cell line results not only in an enlarged proportion of high producing clones, also the volumetric titer of the individual C8DEL clones is higher. Considering the results of example 2, it is believed that this increase in yield is attributable to the deletion of gene C12orf35. FIG. 8 shows the volumetric titer of the 45 highest producing clones from the parental cell line derived from CHO-K1 (all Ipo8 positive) and C8DEL from an antibody project (results of the stability analysis of said clones is shown in 4.2). As can be seen, the average volumetric titer for the clones derived from C8DEL is higher compared to the parental cell line, and additionally, also the highest antibody producer clones are originated from C8DEL cell line.

Bioreactor Suitability

Additional tests to evaluate C8DEL cell line in comparison to the parental cell line derived from CHO-K1 were performed inter alia to determine their suitability for upscaling. Bioreactor runs have shown that C8DEL cell line is suitable for upscaling. C8DEL cell line cultivated in bioreactors had a viable cell density that is suitable for large scale production. Furthermore, it was found that the viability was better than that for the parental cell line. Overall, the C8DEL cell line is suitable for upscaling and is outperforming the parental cell line from which it is derived regarding viability. The viability of the C8DEL cell line stays longer at a higher level.

Improved Time Lines from Transfection to Stable Pool Production

Another advantage of the C8DEL cell line is the faster recovery from MTX selection. The recovery of pools after MTX incubation was accomplished 7-8 days faster compared to the parental cell line wherein no portion of the telomeric region of chromosome 8 comprising gene FAM60A is deleted. Overall, it was found that the cell crisis is significant lower with the cells according to the present disclosure.

Example 5

Selection Using a Folate Receptor as Selectable Marker

The C8DEL cell line was used in different settings in conjunction with the folic acid receptor as selectable marker and shows particular advantages in conjunction with said selection system. In particular, a combined selection against the folate receptor and DHFR as selectable markers is beneficial. Here, the transfected cells comprised a human folate receptor alpha and DHFR as selectable markers and expressed an antibody. Whereas selection of the parental cell line with very low amounts of folic acid (50 nM folic acid (FA)/50 nM MTX) encountered difficulties due to the selection stringency (cells did not always recover), the combination of C8DEL and the folate receptor as selectable marker is very powerful under such stringent conditions and resulted in a significant volumetric titer increase. Table 11 highlights the volumetric titer differences between the parental cell line and C8DEL as well as the additional volumetric titer increase that is achieved when using the folate receptor as a selection marker in combination with low amounts of folic acid instead of 500 nM MTX selection step. Thus, the use of the mammalian cells described herein wherein the expression of gene FAM60A and gene C12orf35 is reduced or eliminated allows in combination with the folate receptor/DHFR selection system to use very stringent selection conditions that do not require the use of high amounts of toxic agents.

TABLE 11

| Cell line | Selection conditions | Pool titer (mAb g/L) - shake flask batch culture |
|---|---|---|
| Parental cell line derived from CHO-K1 | 0.8 g/L G418/500 nM MTX | Approx. 0.07 |
| C8DEL | 0.8 g/L G418/500 nM MTX | Approx. 0.83 |
| C8DEL | 50 nM FA/50 nM MTX | Approx. 1.61 |

Furthermore, C8DEL cells were transfected (nucleofection) with an expression vector which comprised an expression cassette comprising a polynucleotide encoding a human folate receptor alpha and an expression cassette comprising a polynucleotide encoding DHFR. Thus, both selectable markers FRalpha and DHFR were on the same expression vector. Furthermore, the expression vector comprised an expression cassette comprising a polynucleotide encoding the light chain of an antibody and an expression cassette comprising a polynucleotide encoding the heavy chain of an antibody. The expression cassette for the antibody heavy chain was designed such that a portion of the heavy chain was due to stop codon readthrough produced as membrane-anchored fusion, thereby facilitating FACS selection (see above). Five different selection conditions using 100 nM folic acid (FA) and different concentrations of MTX were tested. The selection media are summarized in subsequent Table 12. After selection, the selected cell pools were transferred to complete medium and grown in shake flask batch cultures. At day 13 of the culture, samples of the culture medium were taken and analyzed for antibody content by Protein-A HPLC. The results are also shown in Table 12.

TABLE 12

| Selection condition | Approx. antibody concentration [g/L] |
|---|---|
| 100 nM FA/no MTX | 0.13 |
| 100 nM FA/1 nM MTX | 0.12 |
| 100 nM FA/5 nM MTX | 0.46 |
| 100 nM FA/10 nM MTX | 1.44 |
| 100 nM FA/50 nM MTX | 1.57 |

As can be seen, a MTX concentration already as low as 5 nM provided a selection advantage. Increasing the selection stringency also increases the volumetric pool titer. Thus, the volumetric antibody productivities are significantly increased. Furthermore, compared to standard MTX selections, significantly lower concentrations of MTX can be used during selection. This is an important advantage considering that MTX is a toxic agent. Furthermore, it was analyzed how the selection stringency influences the volumetric pool titers and the time for selection. It was found that increasing the selection stringency by increasing the concentration of MTX prolongs the recovery time. Thus, the selection stringency can be adjusted according to the needs of different applications (time versus titer).

Furthermore, analysis of the pools obtained after folic acid/MTX selection for surface expression of the antibody by FACS show that using this selection system in combination with the novel cell line significantly increases the abundance of high producers in the cell pool as is apparent from the obtained fluorescent profiles shown as FIG. 9A to E. The concentration of MTX was increased from A to E (A: no MTX; B: 1 nM MTX; C: 5 nM MTX; D: 10 nM MTX; E: 50 nM MTX). When increasing the MTX concentration, the number of high expressing cell clones in the cell pool was increased as can be derived from the increase of the peak size on the right hand side (higher fluorescence correlating with a higher antibody expression rate). Using 50 nM folic acid in combination with 10 nM MTX (see FIG. 9D) already resulted in a cell pool predominantly comprising high producing cell clones (one dominant peak on the right hand side). Furthermore, when increasing the MTX concentration to 50 nM (see FIG. 9E), basically exclusively high-producing cells were comprised in the obtained pool. These results are remarkable, because when using the C8DEL cell line in combination with the folate receptor/DHFR selection system, one obtains a pool profile after FACS analysis, which closely resembles more that of a cell clone (comprising genetically identical cells) than that of a cell pool (comprising genetically different cells). It appears that the deletion of the C12orf35 gene comprised in the lost telomeric region of cell line C8DEL results in a significant increase of the volumetric productivity, so that basically the majority of the cells in the cell pools obtained after folic acid/MTX selection under appropriate conditions were high producers according to the FACS profiles.

Furthermore, it was found that when cultivating stably transfected clones obtained from the C8DEL cell line (gene FAM60A is lost, see above) in selective medium (50 nM folic acid, 10 nM MTX) stability rates of up to 80% and up to almost 100% could be obtained in projects. Significant high stability results were also achieved in a semi-selective medium, which only comprised a limited concentration of folic acid (50 nM), however, no MTX. Here, stability rates up to 87% were achieved with this cell line. In certain projects, stability rates of up to almost 100% were obtained.

Example 6

Validation Tool to Identify High and Stable Producers Based on the Expression Profile A real-time RT-PCR analytical tool was developed to predict clone productivity and stability at an early stage of development pipeline process. Real-time RT-PCR was implemented for four genes: C12orf35, Dennd5b, Fam60a and Ipo8 (all localized at telomeric region on the q arm of chromosome 8). After selection and clone generation, several hundred clones stably expressing an antibody as polypeptide of interest were analyzed with respect to the presence and expression level of these four genes at telomeric region of chromosome 8 and the expression yield. A clear correlation was found between stability, volumetric productivity and a loss in the telomeric region of chromosome 8. A study was conducted to determine if there is a correlation between stability and presence of telomeric region of chromosome 8. Clones were classified as stable if they were not losing more than 25% titer (volumetric) in 12 weeks. A significant correlation between loss of telomeric region of chromosome 8 and clone stability is existent (p-value: 4.67E-06 based on $\chi^2$-test). Consequently, the loss of telomeric region on chromosome 8 which includes gene FAM60A can be used as a prediction tool for stability. Analysing the presence or absence of telomeric region of chromosome 8 via real-time RT-PCR increases the probability to select a higher proportion of stable clones in pipeline projects.

Furthermore, it was found by analyzing several hundred clones that have lost a portion of the telomeric region of chromosome 8, that there appear to be several breakpoints in the telomeric region of chromosome 8 existent that can be induced. In most analysed cases, the breakpoint was located centromeric of the Ipo8 gene. Breakpoints were also detected between FAM60A and Ipo8. The deleted region comprised in all cases gene C12orf35 (which is located telomeric of gene encoding methyltransferase-like protein 20) what is associated with an increase in volumetric productivity.

The invention claimed is:

1. An isolated mammalian host cell for recombinant production of a product of interest, wherein the genome of the mammalian cell is altered so that functional expression of a FAM60A gene is eliminated wherein said cell comprises integrated into its genome at least one heterologous polynucleotide encoding the product of interest comprised in an expression cassette, wherein the product of interest is a polypeptide, and wherein the elimination of the functional expression of the FAM60A gene in the cell increases the expression stability of the product of interest in said cell compared to a control mammalian cell in which expression of the FAM60A gene is not eliminated.

2. The isolated mammalian host cell according to claim 1, wherein the FAM60A gene encodes a protein comprising the amino acid sequence shown in SEQ ID NO: 1, 2, 3, 4, 6, 7, or 8, and/or wherein the mammalian cell has one or more of the following characteristics:
   a) the FAM60A gene comprises one or more mutations which provide a non-functional FAM60A expression product so that the expression stability of the product of interest is increased;
   b) at least one copy of the FAM60A gene is deleted or functionally inactivated in the genome of the mammalian cell;
   c) a portion of a chromosome is deleted, wherein the deleted portion comprises FAM60A gene.

3. The isolated mammalian host cell according to claim 1, wherein the mammalian cell has one or more of the following characteristics:
   a) the mammalian cell is a rodent cell;
   b) the mammalian cell is a hamster cell;
   c) the mammalian cell is a CHO cell;
   d) the mammalian cell is provided as cell clone or cell line;
   e) the mammalian cell expresses endogenously DHFR and a folate receptor.

4. The isolated mammalian host cell according to claim 1, wherein a portion of a chromosome is deleted, wherein the deleted portion comprises the FAM60A gene and wherein:
   a) the mammalian cell is a hamster cell and at least a portion of the telomeric region of chromosome 8 is deleted, wherein said deleted portion comprises the FAM60A gene; or
   b) the mammalian cell is a mouse cell and at least a portion of the telomeric region of chromosome 6 is deleted, wherein said deleted portion comprises the FAM60A gene.

5. The isolated mammalian host cell according to claim 4, wherein the isolated mammalian host cell has one or more of the following characteristics:
   i) the deleted telomeric region comprises the FAM60A gene and comprises one or more genes selected from Caprin2 and Ipo8;
   ii) the deletion is induced by chromosome breakage and the breakpoint is located centromeric of the Ipo8 gene;
   iii) the deletion is induced by chromosome breakage and the breakpoint is located centromeric of the Ipo8 gene, within the Tmtc1 gene;
   iv) at least a portion of the telomeric region is deleted in both chromosomes of the respective chromosome pair, wherein the deleted portions comprise the FAM60A gene.

6. The isolated mammalian host cell according to claim 1, wherein the FAM60A gene encodes a protein comprising the amino acid sequence shown in SEQ ID NO: 1, 2, 3, 4, 6, 7, or 8.

7. The isolated mammalian host cell according to claim 1, wherein the mammalian cell comprises stably integrated into its genome at least one heterologous polynucleotide encoding the product of interest and at least one heterologous polynucleotide encoding a selectable marker or reporter polypeptide and wherein said heterologous polynucleotides are located on the same or different expression vectors.

8. The isolated mammalian host cell according to claim 1, having one or more of the following characteristics:
   a) the mammalian cell secretes said polypeptide of interest into the cell culture medium; and/or
   b) the product of interest is a polypeptide selected from a therapeutic polypeptide and a diagnostic polypeptide.

9. A method for selecting a mammalian host cell which recombinantly expresses a product of interest, wherein the product of interest is a polypeptide, comprising:
   (a) providing mammalian cells according to claim 1 as host cells; and
   (b) selecting one or more host cells expressing the product of interest.

10. The method according to claim 9, having one or more of the following characteristics:
   1) said host cells provided in (a) additionally comprise at least one heterologous polynucleotide encoding a selectable marker and stage (b) comprises culturing said plurality of host cells under conditions selective for the selectable marker;
   2) said host cells provided in (a) comprise at least two heterologous polynucleotides each encoding a selectable marker wherein the first selectable marker is a folate receptor and wherein the second selectable marker is a DHFR and wherein (b) comprises culturing said plurality of host cells in a selective culture medium which comprises folate in a limiting concentration and a DHFR inhibitor;
   3) transfecting one or more expression vectors into the mammalian cells;
   4) (b) comprises multiple selection steps;
   5) (b) comprises performing a flow cytometry based selection; and/or
   6) the product of interest is an immunoglobulin molecule.

11. A method for recombinantly producing a product of interest, wherein the product of interest is a polypeptide, comprising utilizing a mammalian host cell according to claim 1 as host cell for recombinant expression of the product of interest and comprising:
   (a) culturing the host cells according to claim 1 under conditions that allow for the expression of the product of interest; and
   (b) isolating the product of interest from the cell culture medium and/or from said host cells.

12. The method according to claim 11, further comprising:
   (c) processing the isolated product of interest.

13. The method according to claim 11, having one or more of the following characteristics:
   a) the mammalian cell is a rodent cell;
   b) the mammalian cell is a hamster cell;
   c) the mammalian cell is a CHO cell;
   d) the mammalian cell is provided as cell clone or cell line;
   e) the mammalian cell expresses endogenously DHFR and a folate receptor;
   f) the product of interest is a polypeptide selected from a therapeutic polypeptide and a diagnostic polypeptide; and
   g) the product of interest is a polypeptide and the host cell secretes the polypeptide of interest into the cell culture medium.

14. A method for producing a mammalian host cell according to claim 1, comprising altering the genome of an mammalian cell to impair the effect of protein FAM60A in said cell and stably transfecting into said cell at least one expression vector comprising a polynucleotide encoding a product of interest comprised in an expression cassette, wherein the product of interest is a polypeptide.

15. The isolated mammalian host cell of claim 1, wherein functional expression of the FAM60A gene is eliminated by (i) gene knock-out, (ii) gene mutation, and/or (iii) gene deletion.

16. The method according to claim 9, wherein the FAM60A protein comprises the amino acid sequence shown in SEQ ID NO: 1, 2, 3, 4, 6, 7, or 8.

17. The method according to claim 11, wherein the FAM60A protein comprises the amino acid sequence shown in SEQ ID NO: 1, 2, 3, 4, 6, 7, or 8, and/or wherein the mammalian host cell has one or more of the following characteristics:
   a) the FAM60A gene comprises one or more mutations which provide a non-functional FAM60A expression product so that the expression stability of the product of interest is increased;
   b) at least one copy of gene FAM60A is deleted or functionally inactivated in the genome of the mammalian cell;
   c) a portion of a chromosome is deleted, wherein the deleted portion comprises the FAM60A gene.

18. The method according to claim 11, wherein a portion of a chromosome of the mammalian host cell is deleted, wherein the deleted portion comprises the FAM60A gene and wherein:
   a) the mammalian cell is a hamster cell and at least a portion of the telomeric region of chromosome 8 is deleted, wherein said deleted portion comprises the FAM60A gene; or
   b) the mammalian cell is a mouse cell and at least a portion of the telomeric region of chromosome 6 is deleted, wherein said deleted portion comprises the FAM60A gene.

19. The method according to claim 18, wherein the mammalian host cell has one or more of the following characteristics:
   i) the deleted telomeric region further comprises one or more genes selected from Caprin2 and Ipo8;
   ii) the deletion is induced by chromosome breakage and the breakpoint is located centromeric of the Ipo8 gene;
   iii) the deletion is induced by chromosome breakage and the breakpoint is located centromeric of the Ipo8 gene, within the Tmtc1 gene;
   iv) at least a portion of the telomeric region is deleted in both chromosomes of the respective chromosome pair, wherein the deleted portions comprise the FAM60A gene.

20. The method according to claim 11, wherein the FAM60A gene encodes a protein comprising the amino acid sequence shown in SEQ ID NO: 1, 2, 3, 4, 6, 7, or 8.

21. The method according to claim 11, wherein the mammalian host cell comprises stably integrated into its genome at least one heterologous polynucleotide encoding the product of interest and at least one heterologous polynucleotide encoding a selectable marker or reporter polypeptide and wherein said heterologous polynucleotides are located on the same or different expression vectors.

22. The method according to claim 14, wherein the FAM60A gene encodes a protein comprising the amino acid sequence shown in SEQ ID NO: 1, 2, 3, 4, 6, 7, or 8.

* * * * *